United States Patent
Becker et al.

(10) Patent No.: US 12,071,392 B2
(45) Date of Patent: *Aug. 27, 2024

(54) AMINOADAMANTYL NITRATE COMPOUNDS AND THEIR USE TO TREAT CNS DISORDERS

(71) Applicant: Panorama Research, Inc., Sunnyvale, CA (US)

(72) Inventors: Cyrus K. Becker, Pleasanton, CA (US); Meenakshi S. Venkatraman, Fremont, CA (US); Xiaoming Zhang, Sunnyvale, CA (US); James W. Larrick, Sunnyvale, CA (US); Stuart Arthur Lipton, Rancho Santa Fe, CA (US)

(73) Assignee: Panorama Research, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,817

(22) Filed: Sep. 19, 2022

(65) Prior Publication Data
US 2023/0130425 A1    Apr. 27, 2023

Related U.S. Application Data

(63) Continuation of application No. 16/766,357, filed as application No. PCT/US2018/061981 on Nov. 20, 2018, now Pat. No. 11,447,442.
(Continued)

(51) Int. Cl.
*C07C 219/24* (2006.01)
*A61K 31/16* (2006.01)
(Continued)

(52) U.S. Cl.
CPC ............ *C07C 219/24* (2013.01); *A61K 31/16* (2013.01); *A61P 11/00* (2018.01); *A61P 25/00* (2018.01);
(Continued)

(58) Field of Classification Search
None
See application file for complete search history.

(56) References Cited

U.S. PATENT DOCUMENTS 6,444,702 B1   9/2002  Wang et al.
11,447,442 B2  9/2022  Becker et al.
(Continued)

FOREIGN PATENT DOCUMENTS

EP   1852113 A2   11/2007
EP   3150574 A1    4/2017
(Continued)

OTHER PUBLICATIONS

Kesselheim ("Two decades of new drug development for central nervous system disorders" Nature Reviews, 2015(14), p. 815-816) (Year: 2015).*
(Continued)

*Primary Examiner* — Amy C Bonaparte
(74) *Attorney, Agent, or Firm* — Clark & Elbing LLP

(57) ABSTRACT

The present disclosure provides adamantyl compounds having one or more amine groups and one or more nitrate groups. The aminoadamantyl nitrate compounds can be used to treat disorders of the central nervous system, including neurodegenerative and non-neurodegenerative diseases.

17 Claims, 1 Drawing Sheet

Related U.S. Application Data

(60) Provisional application No. 62/590,179, filed on Nov. 22, 2017.

(51) Int. Cl.
  A61P 11/00 (2006.01)
  A61P 25/00 (2006.01)
  C07C 211/19 (2006.01)
  C07C 211/27 (2006.01)
  C07C 217/60 (2006.01)
  C07C 219/32 (2006.01)

(52) U.S. Cl.
  CPC .......... C07C 211/19 (2013.01); C07C 211/27 (2013.01); C07C 217/60 (2013.01); C07C 219/32 (2013.01); C07C 2603/74 (2017.05)

(56) References Cited

U.S. PATENT DOCUMENTS

| | | |
|---|---|---|
| 11,529,319 B2 | 12/2022 | Lipton |
| 2003/0008889 A1 | 1/2003 | Wang et al. |
| 2004/0122090 A1 | 6/2004 | Lipton |
| 2005/0049312 A1 | 3/2005 | Makovec et al. |
| 2014/0088083 A1 | 3/2014 | Hollander |
| 2018/0148404 A1 | 5/2018 | Wang et al. |
| 2023/0346713 A1 | 11/2023 | Lipton |

FOREIGN PATENT DOCUMENTS

| | | |
|---|---|---|
| JP | H08-501297 A | 2/1996 |
| JP | 2005-075832 A | 3/2005 |
| JP | 2008-535867 A | 9/2008 |
| JP | 2017-521482 A | 8/2017 |
| WO | WO-94/05275 A1 | 3/1994 |
| WO | WO-02/045710 A1 | 6/2002 |
| WO | WO-2006/034465 A1 | 3/2006 |
| WO | WO-2006/121560 A2 | 11/2006 |
| WO | WO-2007/065036 A2 | 6/2007 |
| WO | WO-2015/180485 A1 | 12/2015 |

OTHER PUBLICATIONS

Morofuji ("Drug Development for Central Nervous System Diseases Using in vitro Blood-brain Barrier Models and Drug Repositioning" Current Pharmaceutical Design, 2020(26), p. 1466-1485) (Year: 2020).*

Van der Brink ("Access to the CNS: Biomarker Strategies for Dopaminergic Treatments" Pharm Res. 2018, 35, p. 64) (Year: 2018).*

Lim ("Chemical Modulators for Targeting Autism Spectrum Disorders: From Bench to Clinic" Molecules, 2022(27), p. 5088) (Year: 2022).*

Altinoz et al., "Targeting nitric oxide and NMDA receptor-associated pathways in treatment of high grade glial tumors. Hypotheses for nitro-memantine and nitrones," Nitric Oxide. 79:68-83 (Sep. 1, 2018) (17 pages).

Extended European Search Report for European Application No. 18882117.7, dated Sep. 9, 2021 (8 pages).

International Search Report for International Application No. PCT/US18/61981, dated Mar. 14, 2019 (4 pages).

Kelly et al., "In vitro and in vivo activities of aminoadamantane and aminoalkylcyclohexane derivatives against Trypanosoma brucei," Antimicrob Agents Chemother. 45(5):1360-6 (2001).

Takahashi et al., "Pharmacologically targeted NMDA receptor antagonism by NitroMemantine for cerebrovascular disease," Sci Rep. 5:14781 (Oct. 19, 2015) (15 pages).

Written Opinion for International Application No. PCT/US18/61981, dated Mar. 14, 2019 (4 pages).

Yoshiyama et al., "Alzheimer's disease and N-Methyl-D-aspartate (NMDA) receptors: extrasynaptic NMDA receptor hypothesis," Dementia Japan 31(1):94-116 (Jan. 2017). English abstract included.

Lipton, "Application of FDA-approved memantine and newer nitromemantine derivatives to treat neurological manifestations in rodent models of tuberous sclerosis complex," CDRMP Research award, May 2014, available <https://apps.dtic.mil/dtic/tr/fulltext/u2/a604193.pdf> (7 pages).

Zweier et al., "Mutations in MEF2C from the 5q14.3q15 microdeletion syndrome region are a frequent cause of severe mental retardation and diminish MECP2 and CDKL5 expression," Hum Mutat. 31(6):722-33 (2010).

* cited by examiner

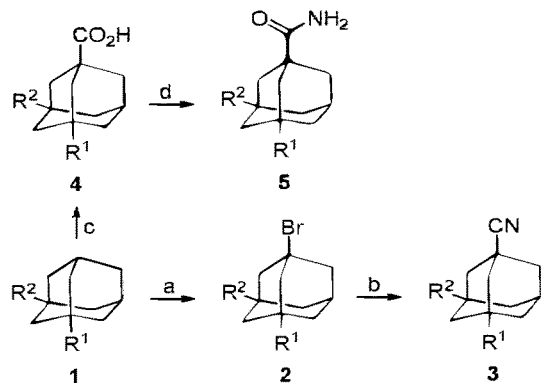

Compounds 1-16:
a: R¹ = Me, R² = H
b: R¹ = Et, R² = H
c: R¹ = Et, R² = Et
d: R¹ = n-Pr, R² = H
e: R¹ = n-Pr, R² = n-Pr Reagents and conditions: (a) Br$_2$, heat; (b) KCN, heat; (c) H$_2$SO$_4$, then HCO$_2$H; (d) oxalyl chloride, then NH$_4$OH

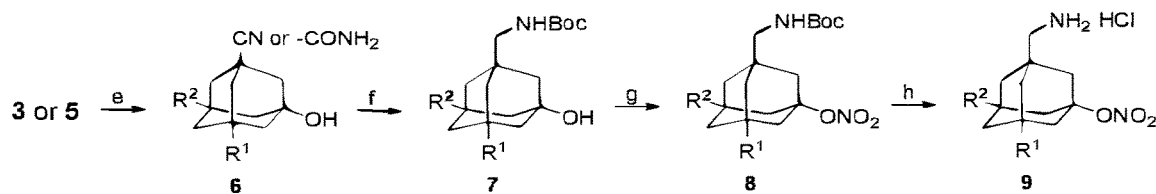

Reagents and conditions: (e) H$_2$SO$_4$, then H$_2$O; (f) LiAlH$_4$, then Boc$_2$O; (g) HNO$_3$/Ac$_2$O; (h) HCl

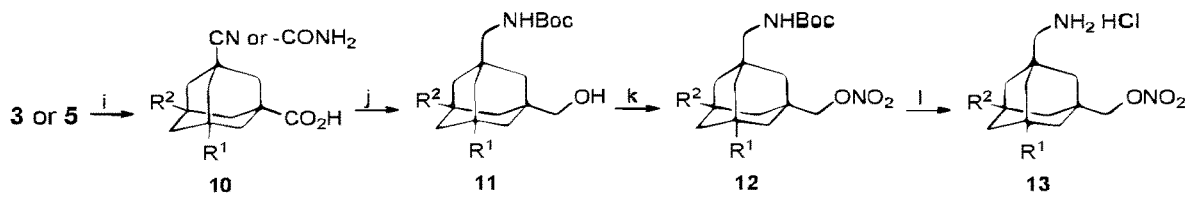

Reagents and conditions: (i) H$_2$SO$_4$, then HCO$_2$H; (j) LiAlH$_4$, then Boc$_2$O; (k) HNO$_3$/Ac$_2$O; (l) HCl

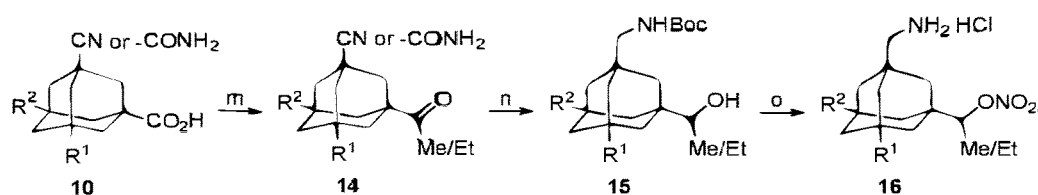

Reagents and conditions: (m) MeLi or EtLi; (n) LiAlH$_4$, then Boc$_2$O; (o) HNO$_3$/Ac$_2$O, then HCl

AMINOADAMANTYL NITRATE COMPOUNDS AND THEIR USE TO TREAT CNS DISORDERS

BACKGROUND OF THE DISCLOSURE

The N-methyl-D-aspartate receptor (also known as the NMDA receptor or NMDAR) is an excitatory glutamate receptor and ion-channel protein found in neurons in the central nervous system (CNS). Activation of the NMDA receptor requires the binding of glutamate (or aspartate or NMDA, both weaker stimulants), which is released following depolarization of the presynaptic neuron, and the binding of glycine (or D-serine, a stronger co-agonist) for efficient opening of the ion-channel part of the receptor. Activation of the NMDAR produces an excitatory postsynaptic potential that results in the opening of a transmembrane ion channel and flow of non-selective cations through it. While the opening and closing of the ion channel is primarily gated by ligand binding, the current flow through the ion channel is voltage-dependent. Extracellular magnesium ($Mg^{2+}$) ions can bind to an allosteric site in the NMDAR channel at resting membrane potential, thereby blocking the passage of other cations through the open ion channel. Depolarization of the postsynaptic membrane in the scale of milliseconds mediated by another type of ionotropic glutamate receptor, the AMPA receptor, dislodges and repels the $Mg^{2+}$ ions from the pore, thereby allowing a voltage-dependent flow of sodium ($Na^+$) ions and calcium ($Ca^{2+}$) ions into the cell and potassium ($K^+$) ions out of the cell. The influx of $Ca^{2+}$ triggers intracellular signaling pathways with $Ca^{2+}$ acting as a second messenger.

The ion channel of an NMDA receptor opens and remains open only when the co-agonists glutamate and glycine are bound to the receptor and the postsynaptic membrane is depolarized to remove the voltage-dependent channel block by $Mg^{2+}$. This property of the NMDA receptor is an important cellular mechanism for synaptic plasticity and long-term potentiation underpinning it. NMDAR-mediated neurotransmission is the primary interneuronal communication underlying synaptic plasticity.

NMDA receptors are located synaptically and extrasynaptically. The proportion of synaptic NMDARs increases with development, although a significant number of extrasynaptic NMDARs remains in adulthood. $Ca^{2+}$ influx through activated synaptic NMDARs is important for controlling synaptic plasticity and synapse formation underlying memory, learning and formation of neural networks during development of the CNS. Under pathological conditions, however, excessive extracellular levels of glutamate cause overstimulation of extrasynaptic NMDARs and continuous depolarization of neurons, resulting in excessive $Ca^{2+}$ influx into neurons. Excessive intracellular $Ca^{2+}$ concentration disrupts calcium homeostasis and initiates a cascade of signaling pathways, leading to upregulation of neuronal nitric oxide synthase, dysfunction of mitochondria, production of reactive oxygen species, deregulation of oxidative phosphorylation, endoplasmic reticulum stress, release of lysosomal enzymes, and ultimately neuronal death. Overactivation of extrasynaptic NMDARs causing excessive influx of $Ca^{2+}$ can lead to excitotoxicity implicated in neurodegenerative disorders such as Alzheimer's disease, Huntington's disease and Parkinson's disease. Alzheimer's disease is the most common neurodegenerative disorder and the most common form of dementia, afflicts at least 18 million people worldwide, and will become more prevalent as the number of elderly people grows.

SUMMARY OF THE DISCLOSURE

The disclosure provides aminoadamantyl nitrate compounds that are selective uncompetitive antagonists of activated extrasynaptic NMDA receptors. In some embodiments, the aminoadamantyl nitrate compounds are of Formula I:

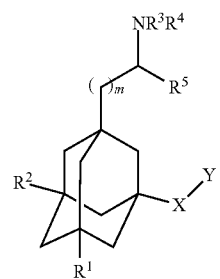

I and pharmaceutically acceptable salts, solvates, hydrates, clathrates, polymorphs and stereoisomers thereof, wherein Y is a nitrate-containing group and $R^1$, $R^2$, $R^3$, $R^4$, $R^5$, X and m are as defined elsewhere herein.

In other embodiments, the aminoadamantyl nitrates are of Formulas II and III:

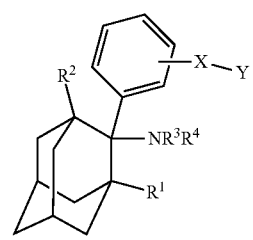

II and

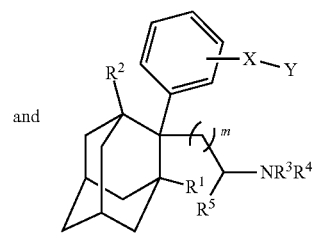

III and pharmaceutically acceptable salts, solvates, hydrates, clathrates, polymorphs and stereoisomers thereof, wherein Y is a nitrate-containing group and $R^1$, $R^2$, $R^3$, $R^4$, $R^5$, X and m are as defined elsewhere herein.

The aminoadamantyl nitrate compounds can be used to treat a broad range of neurodegenerative and other CNS disorders, including Alzheimer's disease, vascular dementia, Huntington's disease, Parkinson's disease, cerebral ischemia, traumatic brain injury, epilepsy and autism spectrum disorder.

BRIEF DESCRIPTION OF THE DRAWINGS

A better understanding of features and advantages of the present disclosure will be obtained by reference to the following detailed description, which sets forth illustrative embodiments of the disclosure, and the accompanying drawings.

FIG. 1 describes the synthesis of various aminoadamantyl nitrate compounds.

DETAILED DESCRIPTION OF THE DISCLOSURE

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein can be employed in practicing the disclosure. It is also understood that every embodiment of the disclosure can optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act or step, the order of the acts or steps of the method is not necessarily limited to the order in which the acts or steps of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

I. Definitions

As used in the specification and the appended claims, the indefinite articles "a" and "an" and the definite article "the" can include plural referents as well as singular referents unless specifically stated otherwise or the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within 20%, 15%, 10% or 5% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" excipient or carrier of a pharmaceutical composition is also compatible with the other ingredients of the composition.

The term "therapeutically effective amount" refers to an amount of a compound that, when administered to a subject, is sufficient to prevent development of, or to alleviate to some extent, the medical condition being treated or one or more symptoms associated with the condition. The term "therapeutically effective amount" also refers to an amount of a compound that is sufficient to elicit the biological or medical response of a cell, tissue, organ, system, animal or human which is sought by a researcher, veterinarian, medical doctor or clinician.

The terms "treat", "treating", and "treatment" include alleviating or abrogating a medical condition or one or more symptoms associated with the condition, and alleviating or eradicating one or more causes of the condition. Reference to "treatment" of a condition is intended to include prevention of the condition. The terms "prevent", "preventing", and "prevention" include precluding or delaying the onset of a medical condition or one or more symptoms associated with the condition, precluding a subject from acquiring a condition, and reducing a subject's risk of acquiring a condition.

The term "medical conditions" includes diseases and disorders.

The terms "diseases" and "disorders" are used interchangeably herein.

The term "subject" refers to an animal, including but not limited to a mammal, such as a primate (e.g., a human, a chimpanzee or a monkey), a rodent (e.g., a rat, a mouse, a guinea pig, a gerbil or a hamster), a lagomorph (e.g., a rabbit), a swine (e.g., a pig), an equine (e.g., a horse), a canine (e.g., a dog) or a feline (e.g., a cat). The terms "subject" and "patient" are used interchangeably herein in reference, e.g., to a mammalian subject, such as a human subject.

The term "compound" encompasses salts, solvates, hydrates, clathrates and polymorphs of that compound. A "solvate" of a compound includes a stoichiometric or non-stoichiometric amount of a solvent (e.g., water, acetone or an alcohol [e.g., ethanol]) bound non-covalently to the compound. A "hydrate" of a compound includes a stoichiometric or non-stoichiometric amount of water bound non-covalently to the compound. A "clathrate" of a compound contains molecules of a substance (e.g., a solvent) enclosed in the crystal structure of the compound. A "polymorph" of a compound is a crystalline form of the compound. The specific recitation of "salt", "solvate", "hydrate", "clathrate" or "polymorph" with respect to a compound in certain instances of the disclosure shall not be interpreted as an intended omission of any of these forms in other instances of the disclosure where the term "compound" is used without recitation of any of these forms, unless the context clearly indicates otherwise.

The terms "halogen", "halide" and "halo" refer to fluorine/fluoride, chlorine/chloride, bromine/bromide and iodine/iodide.

The term "alkyl" refers to a linear or branched, saturated monovalent hydrocarbon radical, wherein the alkyl group can optionally be substituted with one or more substituents as described herein. In certain embodiments, an alkyl group is a linear saturated monovalent hydrocarbon radical that has 1 to 10 ($C_{1-10}$) or 1 to 6 ($C_{1-6}$) carbon atoms, or is a branched saturated monovalent hydrocarbon radical that has 3 to 10 ($C_{3-10}$) or 3 to 6 ($C_{3-6}$) carbon atoms. As an example, the term "$C_{1-6}$ alkyl" refers to a linear saturated monovalent hydrocarbon radical of 1 to 6 carbon atoms or a branched saturated monovalent hydrocarbon radical of 3 to 6 carbon atoms. Linear $C_{1-6}$ and branched $C_{3-6}$ alkyl groups may also be referred to as "lower alkyl". Non-limiting examples of alkyl groups include methyl, ethyl, propyl (including n-propyl and isopropyl), butyl (including all isomeric forms, such as n-butyl, isobutyl, sec-butyl and tert-butyl), pentyl (including all isomeric forms, such as n-pentyl), and hexyl (including all isomeric forms, such as n-hexyl).

The terms "alkylene" and "-alkyl-" refer to a divalent alkyl group, which can optionally be substituted with one or more substituents as described herein.

The term "heteroalkyl" refers to a linear or branched, saturated monovalent hydrocarbon group containing one or more heteroatoms independently selected from O, N and S. In some embodiments, one or more heteroatoms are in the main chain of the linear or branched hydrocarbon group. The terms "heteroalkylene" and "-heteroalkyl-" refer to a divalent heteroalkyl group. A heteroalkyl group and a-heteroalkyl- group can optionally be substituted with one or more substituents as described herein. Examples of heteroalkyl and -heteroalkyl-groups include without limitation —$(CH_2)_m$ —(O or S)—$(CH_2)_n CH_3$ and —$(CH_2)_m$—(O or S)—$(CH_2)_p$—, wherein m is 1, 2, or 3, n is 0, 1 or 2, and p is 1, 2 or 3.

The term "alkoxy" refers to an —O-alkyl group, which can optionally be substituted with one or more substituents as described herein.

Examples of —O-heteroalkyl and —O-heteroalkyl- groups include without limitation ethylene glycol groups and polyethylene glycol (PEG) groups, including but not limited to —$(OCH_2CH_2)_n$—OR and —$(OCH_2CH_2)_nO$— wherein R is hydrogen or alkyl and in is 1, 2 or 3. It is understood that for a —O-heteroalkyl-$ONO$ group, when the —O-heteroalkyl- group is an ethylene glycol or PEG group, the terminal oxygen atom of the ethylene glycol or PEG group is part of the nitrate (—$ONO_2$) group. An —O-heteroalkyl group and an —O-heteroalkyl- group can optionally be substituted with one or more substituents as described herein.

The term "haloalkyl" refers to an alkyl group that is substituted with one or more halogen/halide atoms. A haloalkyl group can optionally be substituted with one or more additional substituents as described herein. Examples of haloalkyl groups include without limitation fluoroalkyl groups, such as —$CH_2F$, —$CHF_2$, and —$(CH_2)_nCF_3$, and perfluoroalkyl groups such as —$CF_3$ and —$(CF_2)_nCF$— wherein n is 1, 2, 3, 4 or 5.

The term "-alkylaryl" refers to an alkyl group that is substituted with one or more aryl groups. An -alkylaryl group can optionally be substituted with one or more additional substituents as described herein.

The term "cycloalkyl" refers to a cyclic saturated, bridged or non-bridged monovalent hydrocarbon radical, which can optionally be substituted with one or more substituents as described herein. In certain embodiments, a cycloalkyl group has from 3 to 10 ($C_{3-10}$), or from 3 to 8 ($C_{3-8}$), or from 3 to 6 ($C_{3-6}$) carbon atoms. Non-limiting examples of cycloalkyl groups include cyclopropyl, cyclobutyl, cyclopentyl, cyclohexyl, cycloheptyl, cyclooctyl, norbornyl, decalinyl and adamantyl. The term "-cycloalkyl-" refers to a divalent cycloalkyl group, which can optionally be substituted with one or more substituents as described herein.

The terms "heterocyclyl" and "heterocyclic" refer to a monocyclic non-aromatic group or a multicyclic group that contains at least one non-aromatic ring, wherein at least one non-aromatic ring contains one or more heteroatoms independently selected from O, N and S. The non-aromatic ring containing one or more heteroatoms may be attached or fused to one or more saturated, partially unsaturated or aromatic rings. In certain embodiments, a heterocyclyl or heterocyclic group has from 3 to 10, or 3 to 8, or 3 to 6 ring atoms. In some embodiments, a heterocyclyl or heterocyclic group is a monocyclic, bicyclic or tricyclic ring system, which may include a fused or bridged ring system, and in which nitrogen or sulfur atoms can optionally be oxidized, nitrogen atoms can optionally be quaternized, and one or more rings may be fully or partially saturated, or aromatic. A heterocyclyl or heterocyclic group may be attached to the main structure at any heteroatom or carbon atom which results in the creation of a stable compound. Examples of heterocyclyl or heterocyclic groups include without limitation azepinyl, azetidinyl, aziridinyl, benzodioxanyl, benzodioxolyl, benzofuranonyl, benzopyranonyl, benzopyranyl, benzotetrahydrofuranyl, benzotetrahydrothienyl, benzothiopyranyl, β-carbolinyl, chromanyl, decahydroisoquinolinyl, dihydrobenzisothiazinyl, dihydrobenzisoxazinyl, dihydrofuryl, dihydropyranyl, dihydropyrazinyl, dihydropyridinyl, dihydropyrazolyl, dihydropyrimidinyl, dihydropyrrolyl, dioxolanyl, dithianyl, furanonyl, imidazolidinyl, imidazolinyl, indolinyl, indolizinyl, isobenzotetrahydrofuranyl, isobenzotetrahydrothienyl, isochromanyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrrolidinyl, pyrrolinyl, quinuclidinyl, tetrahydrofuryl, tetrahydrofuranyl (oxolanyl), tetrahydroisoquinolinyl, tetrahydropyranyl, tetrahydrothienyl (tetrahydrothiophenyl, thiolanyl), thiamorpholinyl (thiomorpholinyl), thiazolidinyl and 1,3,5-trithianyl. The term "-heterocyclyl-" refers to a divalent heterocyclyl group. A heterocyclyl or heterocyclic group, and a-heterocyclyl- group, can optionally be substituted with one or more substituents as described herein.

The term "aryl" refers to a monocyclic aromatic hydrocarbon group or a multicyclic group that contains at least one aromatic hydrocarbon ring. In certain embodiments, an aryl group has from 6 to 10 ring atoms. Non-limiting examples of aryl groups include phenyl, naphthyl, fluorenyl, azulenyl, anthryl, phenanthryl, biphenyl and terphenyl. The aromatic hydrocarbon ring of an aryl group may be attached or fused to one or more saturated, partially unsaturated or aromatic rings—e.g., dihydronaphthyl, indenyl, indanyl and tetrahydronaphthyl (tetralinyl). The term "-aryl-" refers to a divalent aryl group. An aryl group and an -aryl- group can optionally be substituted with one or more substituents as described herein.

The term "heteroaryl" refers to a monocyclic aromatic group or a multicyclic group that contains at least one aromatic ring, wherein at least one aromatic ring contains one or more heteroatoms independently selected from O, N and S. The heteroaromatic ring may be attached or fused to one or more saturated, partially unsaturated or aromatic rings that may contain only carbon atoms or that may contain one or more heteroatoms. A heteroaryl group may be attached to the main structure at any heteroatom or carbon atom which results in the creation of a stable compound. In certain embodiments, a heteroaryl group has from 5 to 10 ring atoms. Examples of monocyclic heteroaryl groups include without limitation pyrrolyl, pyrazolyl, pyrazolinyl, imidazolyl, oxazolyl, isoxazolyl, thiazolyl, thiadiazolyl, isothiazolyl, furanyl, thienyl (thiophenyl), oxadiazolyl, triazolyl, tetrazolyl, pyridyl, pyridonyl, pyrazinyl, pyrimidinyl, pyridazinyl, pyridazinonyl and triazinyl. Non-limiting examples of bicyclic heteroaryl groups include indolyl, benzothiazolyl, benzothiadiazolyl, benzoxazolyl, benzisoxazolyl, benzothienyl (benzothiophenyl), quinolinyl, tetrahydroisoquinolinyl, isoquinolinyl, benzimidazolyl, benzotriazolyl, indolizinyl, benzofuranyl, isobenzofuranyl, chromonyl, coumarinyl, cinnolinyl, quinazolinyl, quinoxalinyl, indazolyl, naphthyridinyl, phthalazinyl, quinazolinyl, purinyl, pyrrolopyridinyl, furopyridinyl, thienopyridinyl, dihydroisoindolyl and tetrahydroquinolinyl. Examples of tricyclic heteroaryl groups include without limitation carbazolyl, benzindolyl, dibenzofuranyl, phenanthrollinyl, acridinyl, phenanthridinyl, xanthenyl and phenothiazinyl. The term "-heteroaryl-" refers to a divalent heteroaryl group. A heteroaryl group and a -heteroaryl- group can optionally be substituted with one or more substituents as described herein.

Each group described herein (including without limitation monovalent and divalent alkyl, heteroalkyl, —O-alkyl, —O-heteroalkyl, alkylaryl, cycloalkyl, heterocyclyl, aryl and heteroaryl), whether as a primary group or as a substituent group, can optionally be substituted with one or more substituents. In certain embodiments, each group described herein can optionally be substituted with 1, 2, 3, 4, 5 or 6 substituents independently selected from halide, cyano, nitro, nitrate, hydroxyl, sulfhydryl (—SH), —NH$_2$, —OR$^{11}$, —SR$^{11}$, —NR$^{12}$R$^{13}$, —C(=O)R$^{11}$, —C(=O)OR$^{11}$, —OC(=O)R$^{11}$, —C(=O)NR$^{12}$R$^{13}$, —NR$^{12}$C(=O)R$^{13}$, —OC(=O)OR$^{11}$, —OC(=O)NR$^{12}$R$^{13}$, —NR$^{12}$C(=O)OR$^{11}$, —NR$^{11}$C(=O)NR$^{12}$R$^{13}$, alkyl, haloalkyl, cycloalkyl, heterocyclyl, aryl and heteroaryl, wherein:
  R$^{11}$ in each occurrence independently is hydrogen, alkyl, cycloalkyl, heterocyclyl, aryl or heteroaryl; and
  R$^{12}$ and R$^{13}$ in each occurrence independently are hydrogen, alkyl, cycloalkyl, heterocyclyl, aryl or heteroaryl, or R$^{12}$ and R$^{13}$ and the nitrogen atom to which they are connected form a heterocyclic or heteroaryl ring.

II. Stereoisomers

It is understood that the present disclosure encompasses all possible stereoisomers, including both enantiomers and all possible diastereomers in substantially pure form and mixtures of both enantiomers in any ratio (including a racemic mixture of enantiomers) and mixtures of two or more diastereomers in any ratio, of the adamantyl compounds described herein having one or more stereocenters, and not only the specific stereoisomers as indicated by drawn structure or nomenclature, Some embodiments of the disclosure relate to the specific stereoisomers indicated by drawn structure or nomenclature. The specific recitation of the phrase "or stereoisomers thereof" or the like with respect to a compound in certain instances of the disclosure shall not be interpreted as an intended omission of any of the other possible stereoisomers of the compound in other instances of the disclosure where the term "compound" is used without recitation of the phrase "or stereoisomers thereof" or the like, unless the context clearly indicates otherwise.

III. Aminoadamantyl Nitrate Compounds

The present disclosure provides novel aminoadamantyl nitrate compounds. In some embodiments, the compounds are of Formula I:

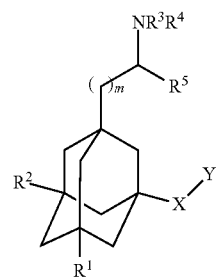

wherein:
  R$^1$ and R$^2$ independently are hydrogen, halide, linear or branched alkyl, linear or branched heteroalkyl, linear or branched alkoxy, linear or branched —O-heteroalkyl, cycloalkyl, heterocyclyl, aryl or heteroaryl, each of which can optionally be substituted;
  R$^3$ and R$^4$ independently are hydrogen or linear or branched C$_1$-C$_6$ alkyl, or R$^3$, R$^4$ and the nitrogen atom to which they are attached form a 3-8-membered heterocyclic ring;
  R$^5$ is hydrogen or linear or branched C$_1$-C$_6$ alkyl;
  X is bond, linear or branched -alkyl-, linear or branched -heteroalkyl-, linear or branched —O-alkyl-, linear or branched —O-heteroalkyl-, —(CH$_2$)$_j$-cycloalkyl-(CH$_2$)$_k$—, —(CH$_2$)$_j$-heterocyclyl-(CH$_2$)$_k$—, —(CH$_2$)$_j$-aryl-(O)$_h$—(CH$_2$)$_k$— or —(CH$_2$)$_j$-heteroaryl-(O)$_h$—(CH$_2$)$_k$—, each of which can optionally be substituted;
  Y is —ONO$_2$ or

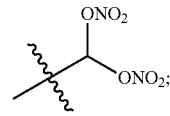

m is 0, 1, 2, 3, 4 or 5;
  j is 0, 1, 2 or 3;
  k is 0, 1, 2 or 3; and
  h is 0 or 1;
and pharmaceutically acceptable salts, solvates, hydrates, clathrates, polymorphs and stereoisomers thereof.

In certain embodiments, the compounds are of Formula Ia:

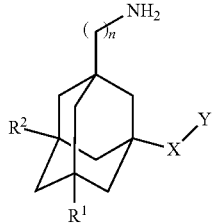

Ia wherein:
R$^1$, R$^2$, X and Y are as defined for Formula I; and
n is 1, 2, 3, 4, 5 or 6;
and pharmaceutically acceptable salts, solvates, hydrates, clathrates, polymorphs and stereoisomers thereof.

In some embodiments, the compounds are of Formula IA:

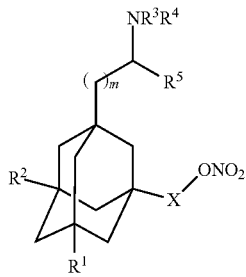

IA wherein R$^1$, R$^2$, R$^3$, R$^4$, R$^5$, X and m are as defined for Formula I;
and pharmaceutically acceptable salts, solvates, hydrates, clathrates, polymorphs and stereoisomers thereof.

In certain embodiments, the compounds are of Formula IAa:

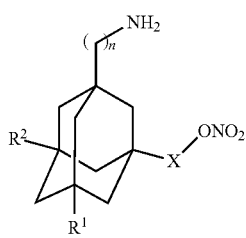

IAa wherein:
R$^1$, R$^2$ and X are as defined for Formula I; and
n is 1, 2, 3, 4, 5 or 6;
and pharmaceutically acceptable salts, solvates, hydrates, clathrates, polymorphs and stereoisomers thereof.

In further embodiments, the compounds are of Formula IB:

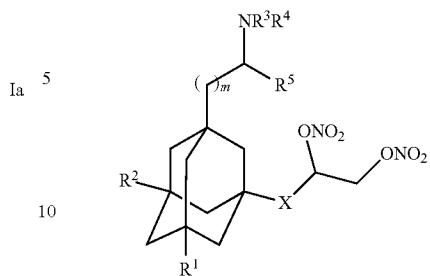

IB wherein R$^1$, R$^2$, R$^3$, R$^4$, R$^5$, X and m are as defined for Formula I;
and pharmaceutically acceptable salts, solvates, hydrates, clathrates, polymorphs and stereoisomers thereof. The stereocenter of the vicinal dinitrate moiety can have the R- or S-stereochemistry or can be racemic.

In certain embodiments, the compounds are of Formula IBa:

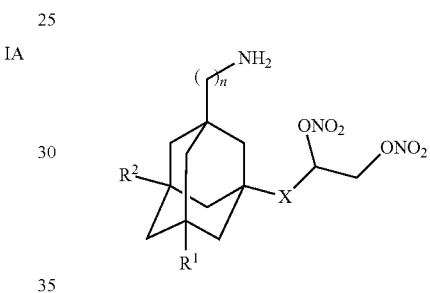

IBa wherein:
R$^1$, R$^2$ and X are as defined for Formula I; and
n is 1, 2, 3, 4, 5 or 6;
and pharmaceutically acceptable salts, solvates, hydrates, clathrates, polymorphs and stereoisomers thereof. The stereocenter of the vicinal dinitrate moiety can have the R- or S-stereochemistry or can be racemic.

In some embodiments, X of the compounds of Formula I and subgenuses thereof is bond, linear or branched C$_1$-C$_6$ or C$_1$-C$_3$-alkyl-, or linear or branched C$_1$-C$_6$ or C$_1$-C$_3$—O-alkyl-. In certain embodiments, X of the compounds of Formula I and subgenuses thereof is bond or linear or branched C$_1$-C$_3$-alkyl- [e.g., —CH$_2$—, —(CH$_2$)$_2$—, —CHCH$_3$, —(CH$_2$)$_3$—, —CHCH$_2$CH$_3$, —CH$_2$CHCH$_3$ or —CH(CH$_3$)CH$_2$—].

In other embodiments, aminoadamantyl nitrate compounds are of Formula II and Formula III:

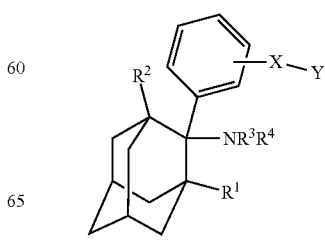

II

-continued and 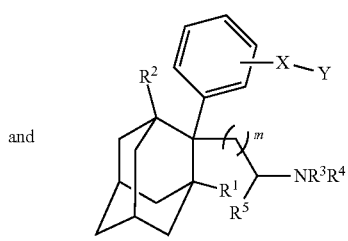

III wherein:
- $R^1$ and $R^2$ independently are hydrogen, halide, linear or branched alkyl, linear or branched heteroalkyl, linear or branched alkoxy, linear or branched —O-heteroalkyl, cycloalkyl, heterocyclyl, aryl or heteroaryl, each of which can optionally be substituted;
- $R^3$ and $R^4$ independently are hydrogen or linear or branched $C_1$-$C_6$ alkyl, or $R^3$, $R^4$ and the nitrogen atom to which they are attached form a 3-8-membered heterocyclic ring;
- $R^5$ is hydrogen or linear or branched $C_1$-$C_6$ alkyl;
- X is bond, linear or branched -alkyl-, linear or branched -heteroalkyl-, linear or branched —O-alkyl-, linear or branched —O-heteroalkyl-, —($CH_2$)$_j$-cycloalkyl-($CH_2$)$_k$—, —($CH_2$)$_j$-heterocyclyl-($CH_2$)$_k$—, —($CH_2$)$_j$-aryl-(O)$_h$—($CH_2$)$_k$— or —($CH_2$)$_j$-heteroaryl-(O)$_h$—($CH_2$)$_k$—, each of which can optionally be substituted;
- Y is —$ONO_2$ or

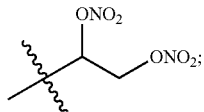

- m is 0, 1, 2, 3, 4 or 5;
- j is 0, 1, 2 or 3;
- k is 0, 1, 2 or 3; and
- h is 0 or 1;

and pharmaceutically acceptable salts, solvates, hydrates, clathrates, polymorphs and stereoisomers thereof.

In some embodiments, the compounds are of Formula IV:

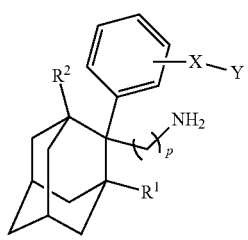

IV wherein:
- $R^1$, $R^2$, X and Y are as defined for Formulas II and III; and
- p is 0, 1, 2, 3, 4, 5 or 6;

and pharmaceutically acceptable salts, solvates, hydrates, clathrates, polymorphs and stereoisomers thereof.

In certain embodiments, the compounds are of Formula IVa:

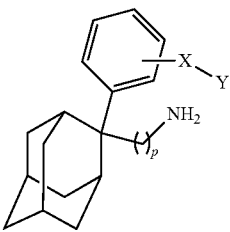

IVa wherein:
- X and Y are as defined for Formulas II and III; and
- p is 0, 1, 2, 3, 4, 5 or 6;

and pharmaceutically acceptable salts, solvates, hydrates, clathrates, polymorphs and stereoisomers thereof.

In further embodiments, the compounds are of Formula IIA and Formula IIIA:

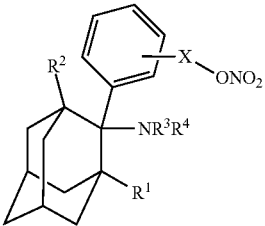

IIA

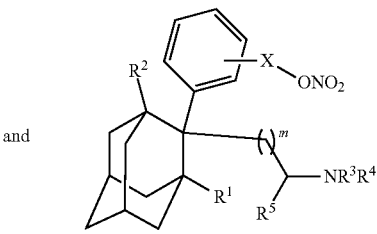

IIIA and wherein $R^1$, $R^2$, $R^3$, $R^4$, $R^5$, X and m are as defined for Formulas TT and 111;
and pharmaceutically acceptable salts, solvates, hydrates, clathrates, polymorphs and stereoisomers thereof.

In some embodiments, the compounds are of Formula IVA:

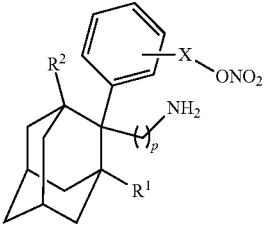

IVa wherein:
- $R^1$, $R^2$ and X are as defined for Formulas II and III; and
- p is 0, 1, 2, 3, 4, 5 or 6;

and pharmaceutically acceptable salts, solvates, hydrates, clathrates, polymorphs and stereoisomers thereof.

In certain embodiments, the compounds are of Formula IVAa:

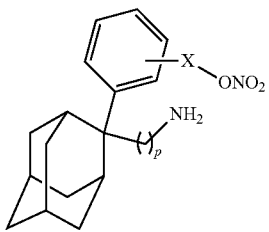

IVAa wherein:
X is as defined for Formulas II and III; and
p is 0, 1, 2, 3, 4, 5 or 6;
and pharmaceutically acceptable salts, solvates, hydrates, clathrates, polymorphs and stereoisomers thereof.

In additional embodiments, the compounds are of Formula IIB and Formula IIIB:

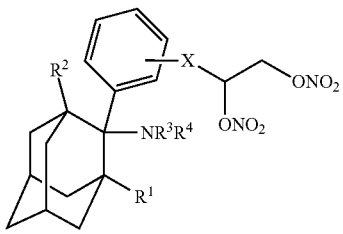

IIB

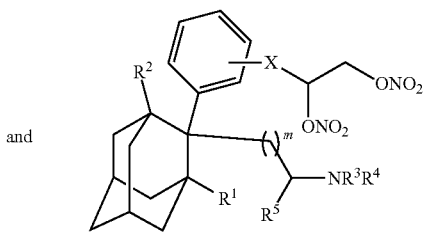

IIIB and wherein $R^1$, $R^2$, $R^3$, $R^4$, $R^5$, X and m are as defined for Formulas II and III;
and pharmaceutically acceptable salts, solvates, hydrates, clathrates, polymorphs and stereoisomers thereof. The stereocenter of the vicinal dinitrate moiety can have the R- or S-stereochemistry or can be racemic.

In some embodiments, the compounds are of Formula IVB:

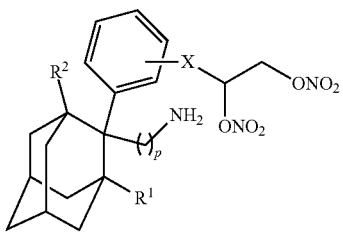

IVB wherein:
$R^1$, $R^2$ and X are as defined for Formulas II and III; and
p is 0, 1, 2, 3, 4, 5 or 6;
and pharmaceutically acceptable salts, solvates, hydrates, clathrates, polymorphs and stereoisomers thereof. The stereocenter of the vicinal dinitrate moiety can have the R- or S-stereochemistry or can be racemic.

In certain embodiments, the compounds are of Formula IVBa:

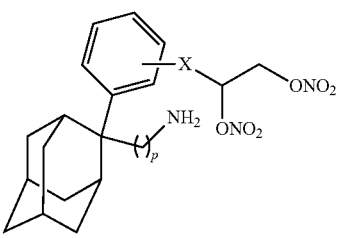

IVBa wherein:
X is as defined for Formulas II and III; and
p is 0, 1, 2, 3, 4, 5 or 6;
and pharmaceutically acceptable salts, solvates, hydrates, clathrates, polymorphs and stereoisomers thereof. The stereocenter of the vicinal dinitrate moiety can have the R- or S-stereochemistry or can be racemic.

For the compounds of Formula II and subgenuses thereof, the compounds of Formula III and subgenuses thereof, and the compounds of Formula IV and subgenuses thereof, the X—Y, X—$ONO_2$ or —X—CH($ONO_2$)$CH_2$—$ONO_2$ moiety can be attached to an ortho position, a meta position or the para position of the phenyl ring. In certain embodiments, the —X—Y, —X—$ONO_2$ or —X—CH($ONO_2$)$CH_2$—$ONO_2$ moiety is attached to a meta position of the phenyl ring.

For the compounds of Formula II and subgenuses thereof, the compounds of Formula III and subgenuses thereof, and the compounds of Formula IV and subgenuses thereof, in some embodiments X is bond, linear or branched $C_1$-$C_6$ or $C_1$-$C_3$-alkyl-, or linear or branched $C_1$-$C_6$ or $C_1$-$C_3$—O-alkyl-. In certain embodiments, X is bond or linear or branched $C_1$-$C_3$—O-alkyl- [e.g., —O—$CH_2$—, —O—$(CH_2)_2$—, —O—$CHCH_3$, —O—$(CH_2)_3$—, —O—$CHCH_2CH_3$, —O—$CH_2CHCH_3$ or —O—$CH(CH_3)CH_2$—].

Regarding the compounds of Formula I and subgenuses thereof, the compounds of Formula II and subgenuses thereof, and the compounds of Formula III and subgenuses thereof, examples of 3-8-membered, nitrogen-containing heterocyclic rings include without limitation aziridinyl, azetidinyl, pyrrolidinyl, piperidinyl, azepanyl and azocanyl. In certain embodiments, $R^3$, $R^4$ and the nitrogen atom to which they are attached form a 3-6-membered heterocyclic ring.

For the compounds of Formula I and subgenuses thereof, the compounds of Formula III and subgenuses thereof, and the compounds of Formula IV and subgenuses thereof, in certain embodiments m is 0, 1 or 2; n is 1, 2 or 3; and p is 0, 1, 2 or 3.

There may be a steric effect in the (electrostatic) interaction of the amine group of the aminoadamantyl nitrate compounds (which is protonated at physiological pH) at or near the N+1 site of the GluN2 (or NR2) subunit in the channel selectivity filter region of the NMDAR channel. For the compounds of Formula I and subgenuses thereof, the compounds of Formula II and subgenuses thereof, and the compounds of Formula III and subgenuses thereof, in some embodiments both $R^3$ and $R^4$ are hydrogen. In other embodiments, one of $R^3$ and $R^4$ is hydrogen, and the other is linear or branched $C_1$-$C_3$ alkyl. In certain embodiments, one of $R^3$ and R[4] is hydrogen, and the other is methyl or ethyl. In yet other embodiments, R[3] and R[4] independently are linear $C_1$-$C_3$ alkyl (e.g., methyl or ethyl), optionally the same alkyl group.

For the compounds of Formula I and subgenuses thereof and the compounds of Formula III and subgenuses thereof, in some embodiments R[5] is hydrogen. In other embodiments, R[5] is linear or branched $C_1$-$C_3$ alkyl. In certain embodiments, R[5] is methyl or ethyl. If the carbon atom connected to the amine group is a stereocenter, the stereocenter can have the R- or S-stereochemistry or can be racemic.

For the compounds of Formula I and subgenuses thereof, the compounds of Formula II and subgenuses thereof, the compounds of Formula III and subgenuses thereof, and the compounds of Formula IV and subgenuses thereof, in some embodiments R[1] and R[2] independently are hydrogen or linear or branched $C_1$-$C_6$ or $C_1$-$C_3$ alkyl. In certain embodiments, both R[1] and R[2] are hydrogen. In other embodiments, R[1] is hydrogen and R[2] is linear or branched $C_1$-$C_6$ or $C_1$-$C_3$ alkyl, or R[2] is hydrogen and R[1] is linear or branched $C_1$-$C_6$ or $C_1$-$C_3$ alkyl. In certain embodiments, R[1] is hydrogen and R[2] is methyl, ethyl or n-propyl, or R[2] is hydrogen and R[1] is methyl, ethyl or n-propyl. In yet other embodiments, R[1] and R[2] independently are linear or branched $C_1$-$C_6$ or $C_1$-$C_3$ alkyl, optionally the same alkyl group. In certain embodiments, R[1] and R[2] independently are methyl, ethyl or n-propyl, optionally the same alkyl group. In some embodiments, R[1] is hydrogen and R[2] is ethyl, or R[2] is hydrogen and R[1] is ethyl. In other embodiments, both R[1] and R[2] are ethyl.

A non-hydrogen group (e.g., an alkyl group) for R[1] or/and R[2] can increase a compound's binding affinity for and dwell time in, and slow its off rate from, the open ion channel of activated NMDA receptors. Furthermore, a more hydrophobic group (e.g., a longer alkyl group) for R[1], R[2] or/and X can increase binding affinity, can compensate for lower affinity that may be associated with the presence of a non-hydrogen group at C-3, C-5 and C-7 of the adamantane scaffold, and can increase a compound's affinity and selectivity for extrasynaptic NMDARs over synaptic NMDARs, although the degree of hydrophobicity of a compound or group(s) thereof may need to be balanced with its solubility in aqueous solution.

For the compounds of Formula I and subgenuses thereof, the compounds of Formula II and subgenuses thereof, the compounds of Formula III and subgenuses thereof, and the compounds of Formula IV and subgenuses thereof, in some embodiments the R[1] group, the R[2] group or the X group, or any combination or all thereof, independently are substituted with 1, 2 or 3 substituents selected from linear or branched $C_1$-$C_6$ or $C_1$-$C_3$ alkyl, haloalkyl, —OR[6], —NR[7]R[8], —ONO$_2$, —CN, —C(=O)R[6], —C(=O)OR[6], —OC(=O)R[6], —C(=O)NR[7]R[8], —NR[7]C(=O)R[6], —OC(=O)OR[6], —OC(=O)NR[7]R[8], —NR[7]C(=O)OR[6], —NR[6]C(=O)NR[7]R[8], aryl and heteroaryl, or/and are substituted with 1 to 6 halogen (e.g., fluorine) or deuterium atoms or have all available hydrogen atoms replaced with halogen (e.g., fluorine) or deuterium atoms, wherein:
R[6] in each occurrence independently is hydrogen or linear or branched $C_1$-$C_6$ or $C_1$-$C_3$ alkyl; and
R[7] and R[8] in each occurrence independently are hydrogen or linear or branched $C_1$-$C_6$ or $C_1$-$C_3$ alkyl, or R[7], R[8] and the nitrogen atom to which they are attached form a 3-6-membered ring.

In certain embodiments, the R[1] group, the R[2] group or the X group, or any combination or all thereof, independently are monovalent or divalent deuteroalkyl, fluoroalkyl or alkyl-ONO$_2$.

Regarding the compounds of Formula I and subgenuses thereof, the compounds of Formula II and subgenuses thereof, the compounds of Formula III and subgenuses thereof, and the compounds of Formula IV and subgenuses thereof, non-limiting examples of linear or branched $C_1$-$C_6$ alkyl groups include methyl, ethyl, n-propyl, isopropyl, n-butyl, isobutyl, sec-butyl, tert-butyl, n-pentyl and n-hexyl. Examples of linear or branched $C_1$-$C_3$ alkyl groups include methyl, ethyl, n-propyl and isopropyl.

For the compounds of Formula I and subgenuses thereof, the compounds of Formula II and subgenuses thereof, the compounds of Formula III and subgenuses thereof, and the compounds of Formula IV and subgenuses thereof, in some embodiments X has 0, 1, 2, 3, 4, 5 or 6 carbon atoms. In certain embodiments, X has 0, 1, 2 or 3 carbon atoms.

Table 1 shows representative compounds of Formula IAa:

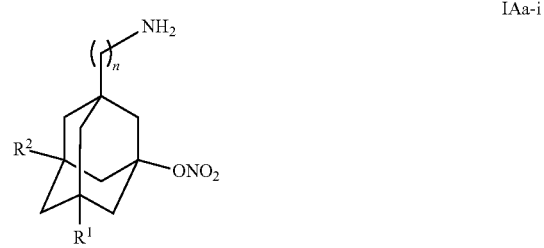

IAa-i

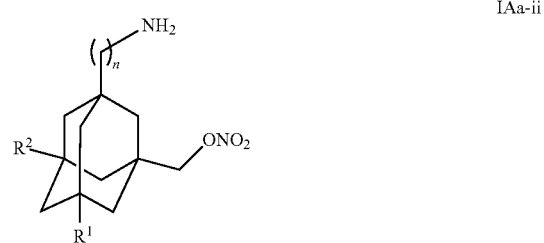

IAa-ii

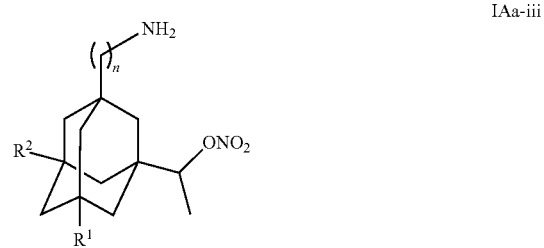

IAa-iii

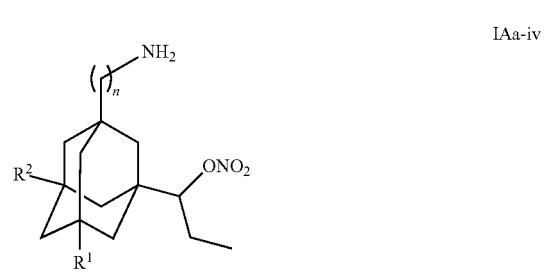

IAa-iv

IAa-v
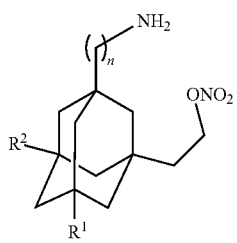
IAa-vi
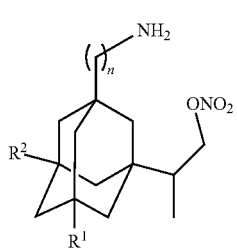
IAa-vii
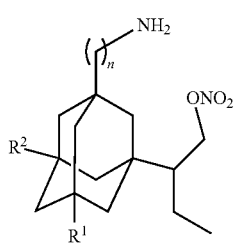
IAa-viii
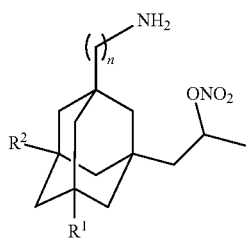
IAa-ix
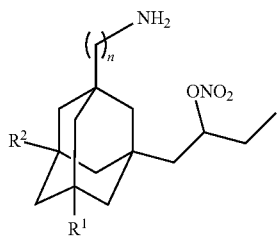
IAa-x
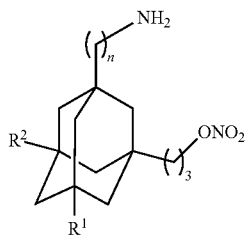
IAa-xi
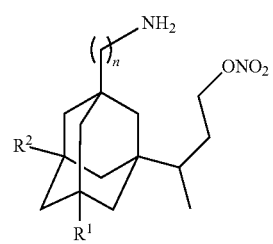
IAa-xii
IAa-xiii
IAa-xiv
IAa-xv
IAa-xvi

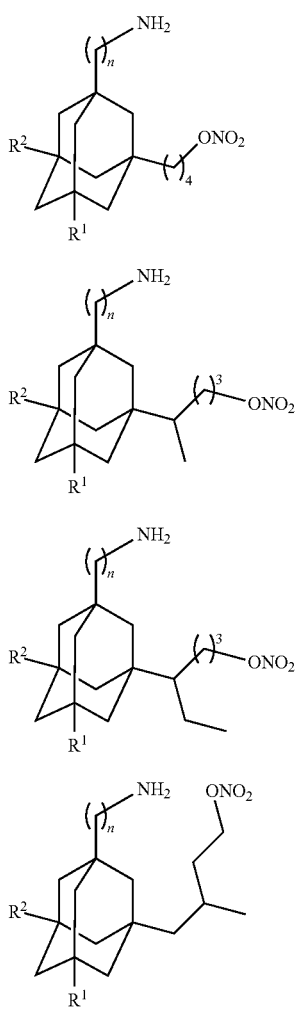

IAa-xvii

IAa-xviii

IAa-xix

IAa-xx

TABLE 1

For each subgenus IAa-i, IAa-ii, IAa-iii, IAa-iv, IAa-v, IAa-vi, IAa-vii, IAa-viii, IAa-ix, IAa-x, IAa-xi, IAa-xii, IAa-xiii, IAa-xiv, IAa-xv, IAa-xvi, IAa-xvii, IAa-viii, IAa-xix and IAa-xx

| n | $R^1$ | $R^2$ |
|---|---|---|
| 1, 2 and 3 | methyl | methyl |
| 1, 2 and 3 | hydrogen | methyl |
| 1, 2 and 3 | methyl | hydrogen |
| 1, 2 and 3 | ethyl | ethyl |
| 1, 2 and 3 | hydrogen | ethyl |
| 1, 2 and 3 | ethyl | hydrogen |
| 1, 2 and 3 | n-propyl | n-propyl |
| 1, 2 and 3 | hydrogen | n-propyl |
| 1, 2 and 3 | n-propyl | hydrogen |
| 1, 2 and 3 | isopropyl | isopropyl |
| 1, 2 and 3 | hydrogen | isopropyl |
| 1, 2 and 3 | isopropyl | hydrogen |
| 1, 2 and 3 | n-butyl | n-butyl |
| 1, 2 and 3 | hydrogen | n-butyl |
| 1, 2 and 3 | n-butyl | hydrogen |
| 1, 2 and 3 | isobutyl | isobutyl |
| 1, 2 and 3 | hydrogen | isobutyl |
| 1, 2 and 3 | isobutyl | hydrogen |
| 1, 2 and 3 | sec-butyl | sec-butyl |
| 1, 2 and 3 | hydrogen | sec-butyl |
| 1, 2 and 3 | sec-butyl | hydrogen |
| 1, 2 and 3 | —$CH_2$—$ONO_2$ | —$CH_2$—$ONO_2$ |

TABLE 1-continued

For each subgenus IAa-i, IAa-ii, IAa-iii, IAa-iv, IAa-v, IAa-vi, IAa-vii, IAa-viii, IAa-ix, IAa-x, IAa-xi, IAa-xii, IAa-xiii, IAa-xiv, IAa-xv, IAa-xvi, IAa-xvii, IAa-viii, IAa-xix and IAa-xx

| n | $R^1$ | $R^2$ |
|---|---|---|
| 1, 2 and 3 | hydrogen | —$CH_2$—$ONO_2$ |
| 1, 2 and 3 | —$CH_2$—$ONO_2$ | hydrogen |
| 1, 2 and 3 | —$(CH_2)_2$—$ONO_2$ | —$(CH_2)_2$—$ONO_2$ |
| 1, 2 and 3 | hydrogen | —$(CH_2)_2$—$ONO_2$ |
| 1, 2 and 3 | —$(CH_2)_2$—$ONO_2$ | hydrogen |
| 1, 2 and 3 | —$(CH_2)_3$—$ONO_2$ | —$(CH_2)_3$—$ONO_2$ |
| 1, 2 and 3 | hydrogen | —$(CH_2)_3$—$ONO_2$ |
| 1, 2 and 3 | —$(CH_2)_3$—$ONO_2$ | hydrogen |
| 1, 2 and 3 | —$CH_2CH(ONO_2)CH_3$ | —$CH_2CH(ONO_2)CH_3$ |
| 1, 2 and 3 | hydrogen | —$CH_2CH(ONO_2)CH_3$ |
| 1, 2 and 3 | —$CH_2CH(ONO_2)CH_3$ | hydrogen |
| 1, 2 and 3 | —$CH_2CH(CH_3)CH_2$—$ONO_2$ | —$CH_2CH(CH_3)CH_2$—$ONO_2$ |
| 1, 2 and 3 | hydrogen | —$CH_2CH(CH_3)CH_2$—$ONO_2$ |
| 1, 2 and 3 | —$CH_2CH(CH_3)CH_2$—$ONO_2$ | hydrogen | and pharmaceutically acceptable salts, solvates, hydrates, clathrates, polymorphs and stereoisomers thereof. The present disclosure specifically discloses each of the 2160 compounds shown in Table 1 and each of the possible stereoisomers thereof. An alkyl-$ONO_2$ group with a stereocenter can have the R- or S-stereochemistry or can be racemic at that stereocenter. Likewise, an $R^1$ or $R^2$ group with a stereocenter can have the R- or S-stereochemistry or can be racemic at that stereocenter.

In certain embodiments, the compounds of Formula IAa are selected from:

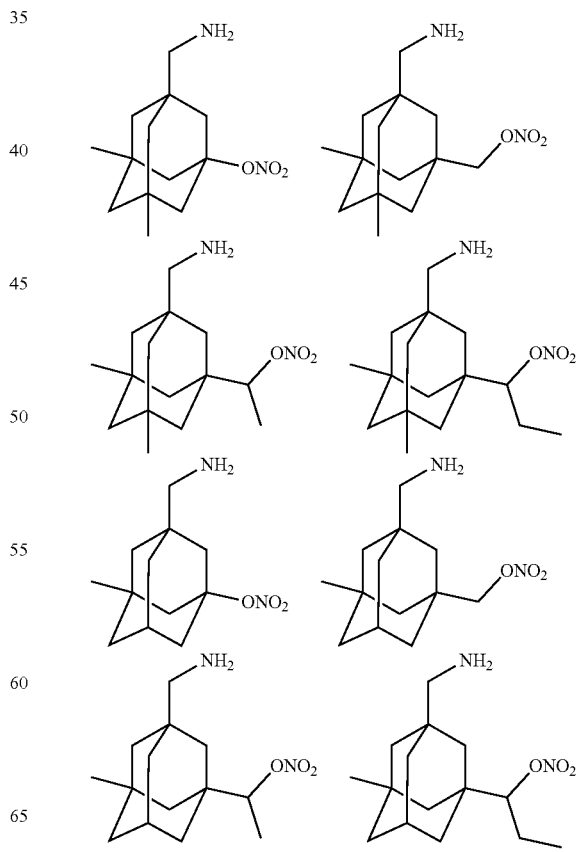

-continued
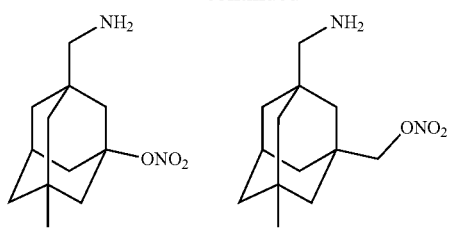
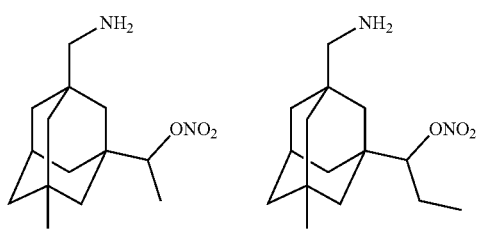
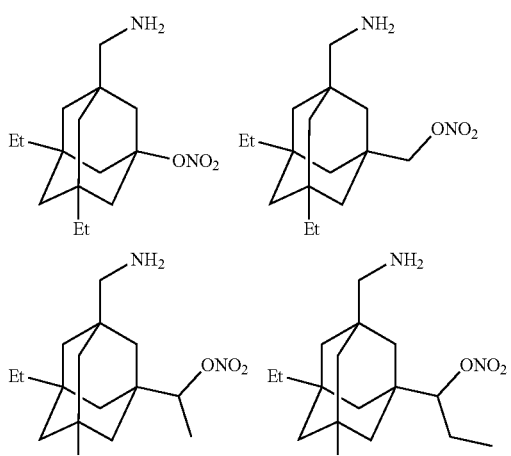
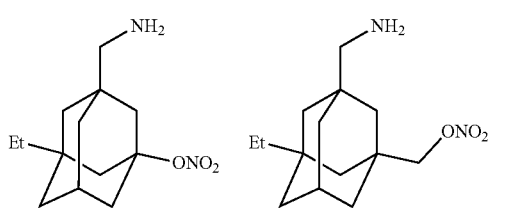
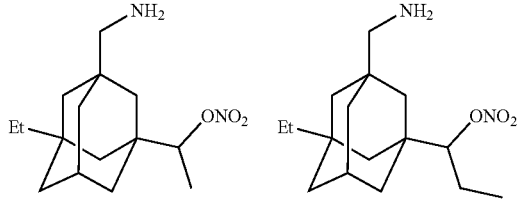
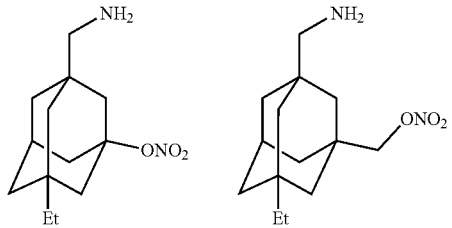
-continued
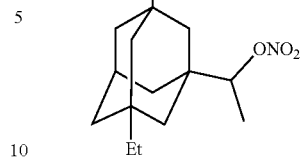
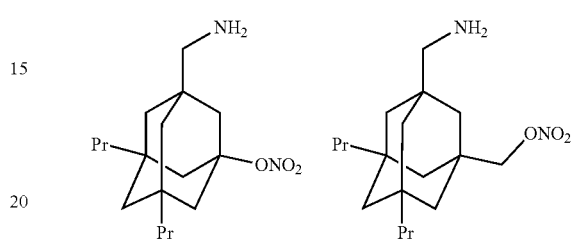
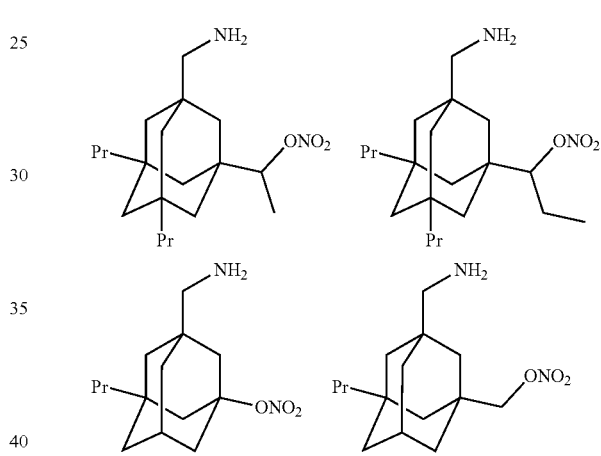
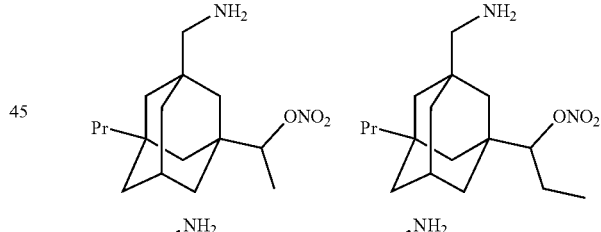
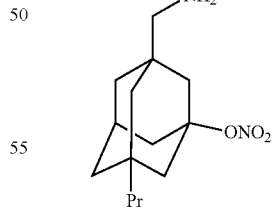
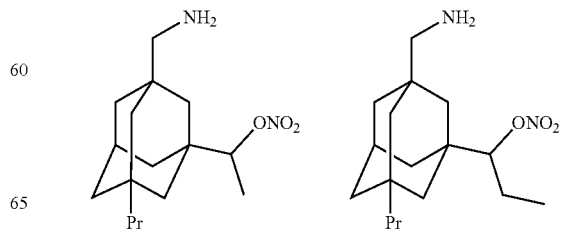

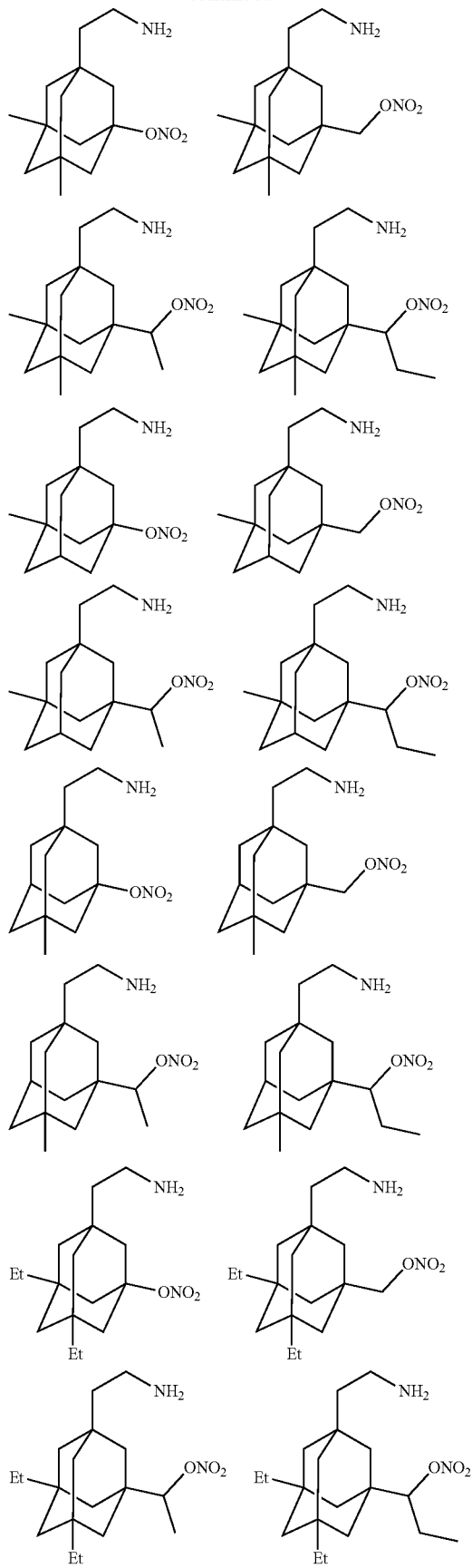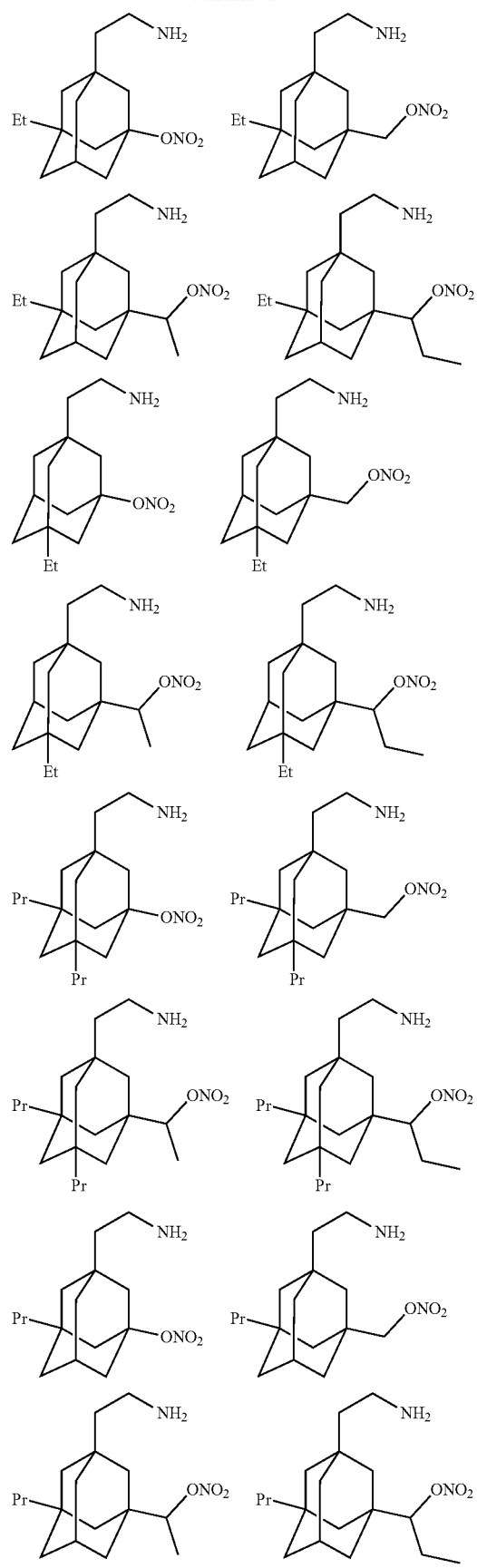

-continued

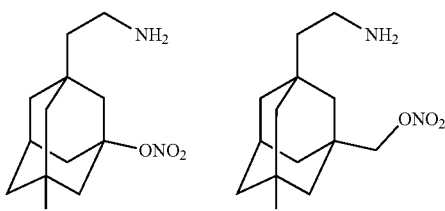

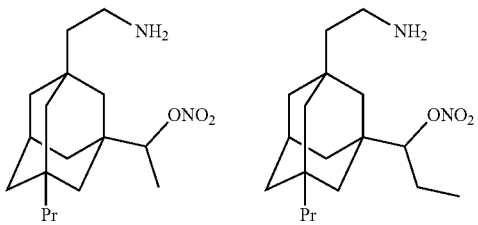

and pharmaceutically acceptable salts, solvates, hydrates, clathrates, polymorphs and stereoisomers thereof, wherein Et=ethyl and Pr=n-propyl. An alkyl-ONO$_2$ group with a stereocenter can have the R- or S-stereochemistry or can be racemic at that stereocenter.

Table 2 shows representative compounds of Formula IBa:

IBa-i
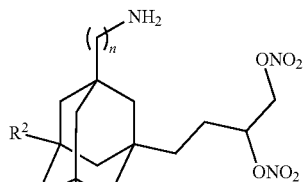

IBa-ii
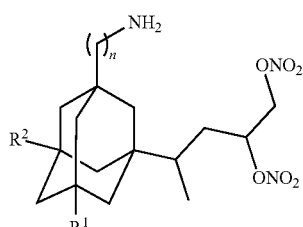

IBa-iii
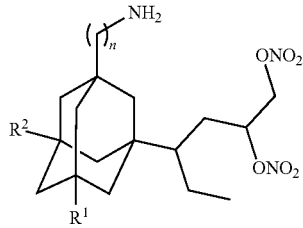

IBa-iv
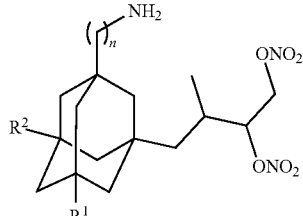

IBa-v
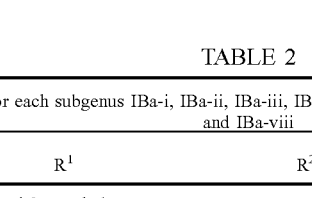

IBa-vi
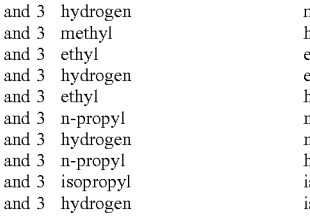

IBa-vii
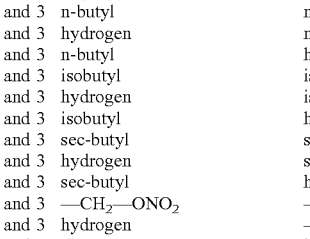

IBa-viii

TABLE 2

| For each subgenus IBa-i, IBa-ii, IBa-iii, IBa-iv, IBa-v, IBa-vi, IBa-vii and IBa-viii | | |
|---|---|---|
| n | R$^1$ | R$^2$ |
| 1, 2 and 3 | methyl | methyl |
| 1, 2 and 3 | hydrogen | methyl |
| 1, 2 and 3 | methyl | hydrogen |
| 1, 2 and 3 | ethyl | ethyl |
| 1, 2 and 3 | hydrogen | ethyl |
| 1, 2 and 3 | ethyl | hydrogen |
| 1, 2 and 3 | n-propyl | n-propyl |
| 1, 2 and 3 | hydrogen | n-propyl |
| 1, 2 and 3 | n-propyl | hydrogen |
| 1, 2 and 3 | isopropyl | isopropyl |
| 1, 2 and 3 | hydrogen | isopropyl |
| 1, 2 and 3 | isopropyl | hydrogen |
| 1, 2 and 3 | n-butyl | n-butyl |
| 1, 2 and 3 | hydrogen | n-butyl |
| 1, 2 and 3 | n-butyl | hydrogen |
| 1, 2 and 3 | isobutyl | isobutyl |
| 1, 2 and 3 | hydrogen | isobutyl |
| 1, 2 and 3 | isobutyl | hydrogen |
| 1, 2 and 3 | sec-butyl | sec-butyl |
| 1, 2 and 3 | hydrogen | sec-butyl |
| 1, 2 and 3 | sec-butyl | hydrogen |
| 1, 2 and 3 | —CH$_2$—ONO$_2$ | —CH$_2$—ONO$_2$ |
| 1, 2 and 3 | hydrogen | —CH$_2$—ONO$_2$ |
| 1, 2 and 3 | —CH$_2$—ONO$_2$ | hydrogen |

TABLE 2-continued

For each subgenus IBa-i, IBa-ii, IBa-iii, IBa-iv, IBa-v, IBa-vi, IBa-vii and IBa-viii

| n | R$^1$ | R$^2$ |
|---|---|---|
| 1, 2 and 3 | —(CH$_2$)$_2$—ONO$_2$ | —(CH$_2$)$_2$—ONO$_2$ |
| 1, 2 and 3 | hydrogen | —(CH$_2$)$_2$—ONO$_2$ |
| 1, 2 and 3 | —(CH$_2$)$_2$—ONO$_2$ | hydrogen |
| 1, 2 and 3 | —(CH$_2$)$_3$—ONO$_2$ | —(CH$_2$)$_3$—ONO$_2$ |
| 1, 2 and 3 | hydrogen | —(CH$_2$)$_3$—ONO$_2$ |
| 1, 2 and 3 | —(CH$_2$)$_3$—ONO$_2$ | hydrogen |
| 1, 2 and 3 | —CH$_2$CH(ONO$_2$)CH$_3$ | —CH$_2$CH(ONO$_2$)CH$_3$ |
| 1, 2 and 3 | hydrogen | —CH$_2$CH(ONO$_2$)CH$_3$ |
| 1, 2 and 3 | —CH$_2$CH(ONO$_2$)CH$_3$ | hydrogen |
| 1, 2 and 3 | —CH$_2$CH(CH$_3$)CH$_2$—ONO$_2$ | —CH$_2$CH(CH$_3$)CH$_2$—ONO$_2$ |
| 1, 2 and 3 | hydrogen | —CH$_2$CH(CH$_3$)CH$_2$—ONO$_2$ |
| 1, 2 and 3 | —CH$_2$CH(CH$_3$)CH$_2$—ONO$_2$ | hydrogen | and pharmaceutically acceptable salts, solvates, hydrates, clathrates, polymorphs and stereoisomers thereof. The present disclosure specifically discloses each of the 864 compounds shown in Table 2 and each of the possible stereoisomers thereof. A nitrated alkyl group with a stereocenter at a branch point can have the R- or S-stereochemistry or can be racemic at that stereocenter. The stereocenter of the vicinal dinitrate moiety can have the R- or S-stereochemistry or can be racemic. Moreover, an R$^1$ or R$^2$ group with a stereocenter can have the R- or S-stereochemistry or can be racemic at that stereocenter.

In certain embodiments, the compounds of Formula IBa are selected from:

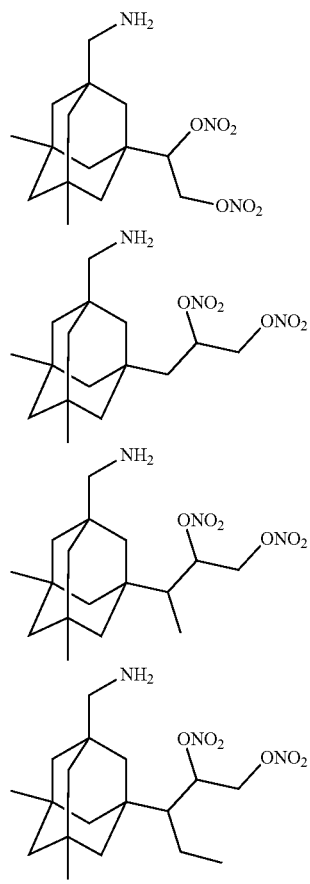
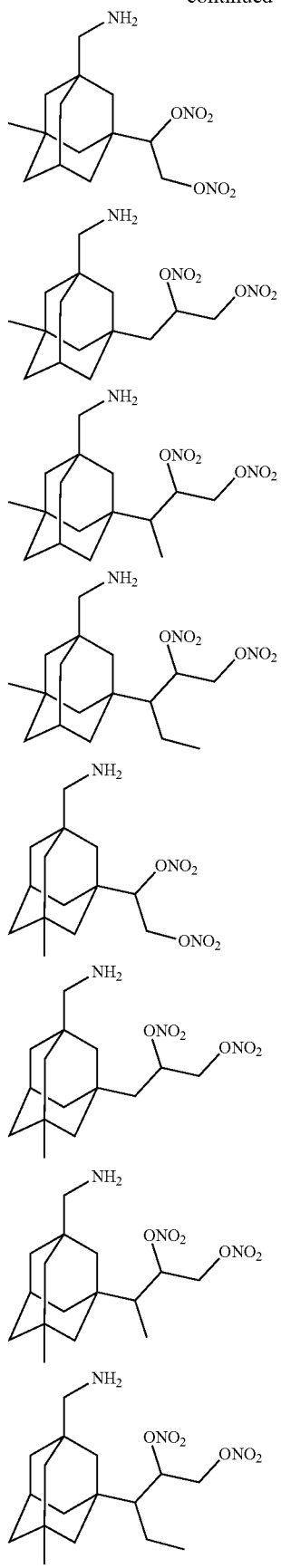

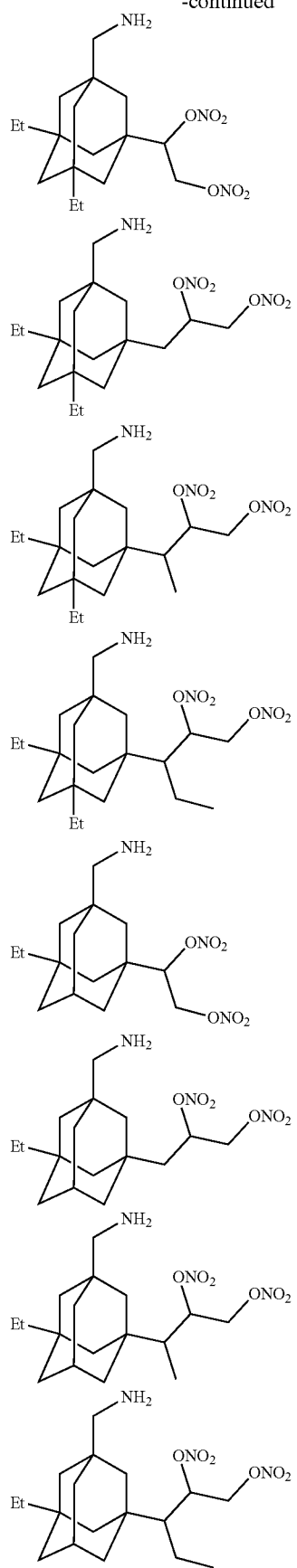
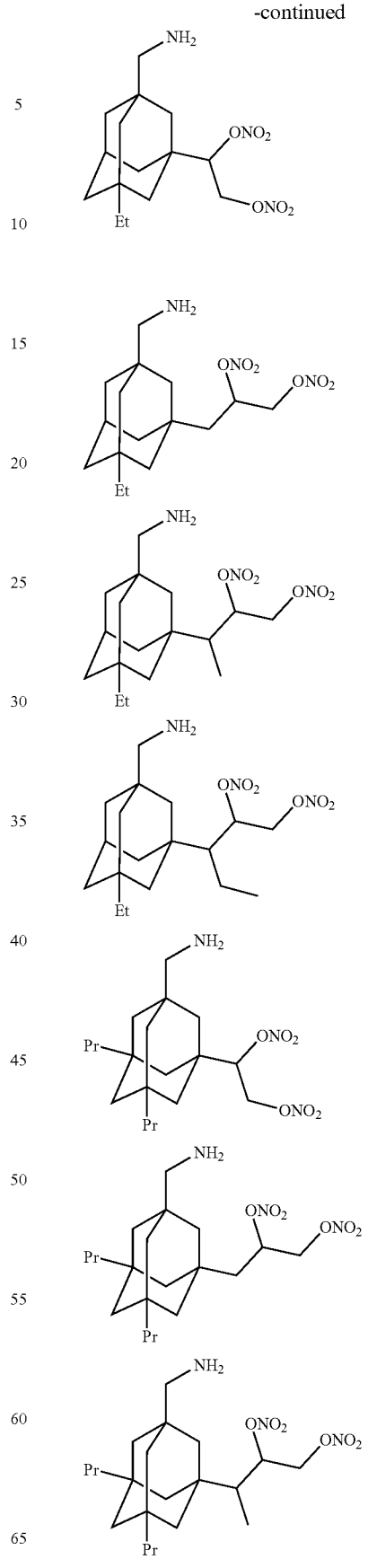

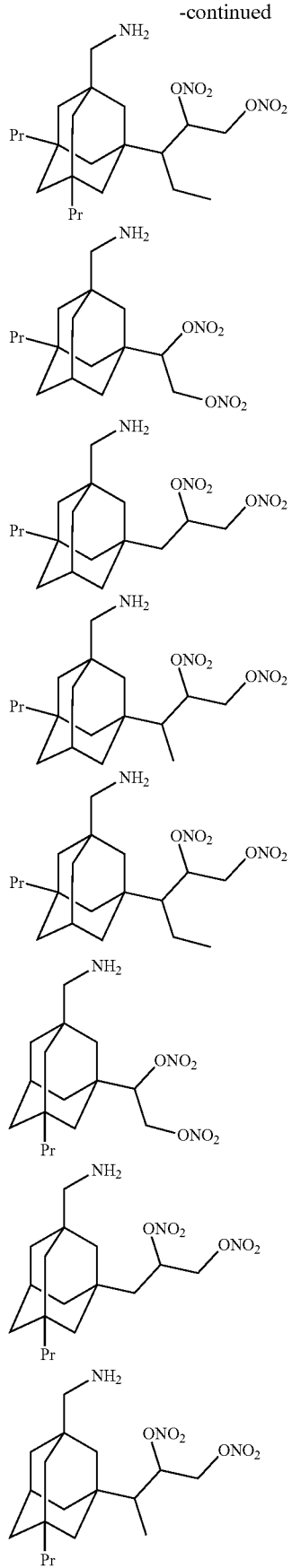
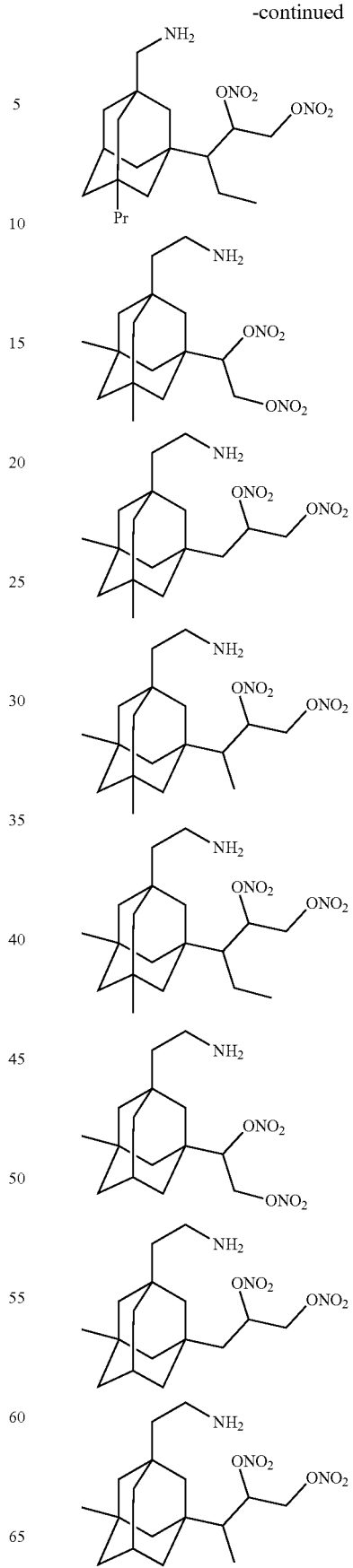

33
-continued
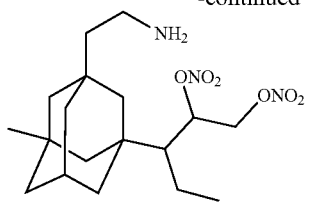
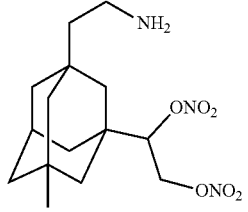
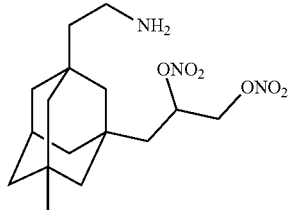
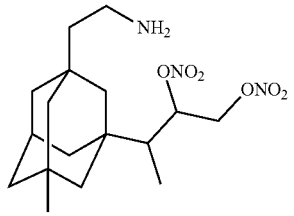
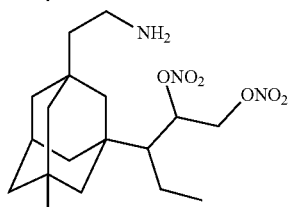
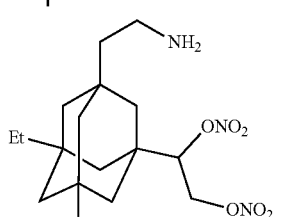
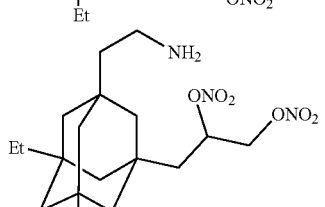
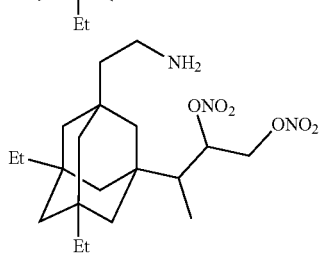
34
-continued
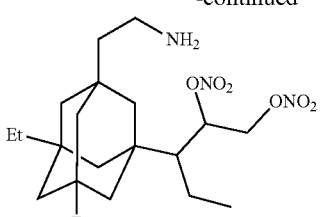
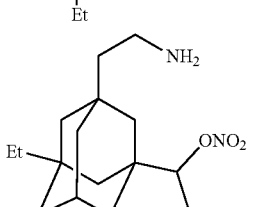
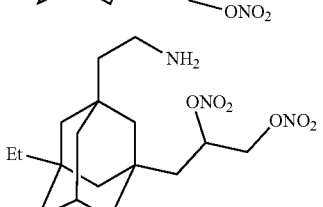
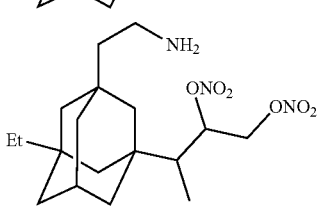
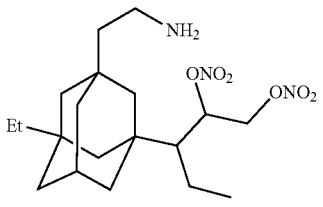
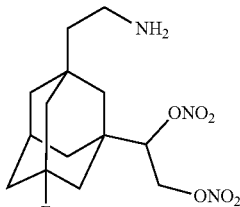
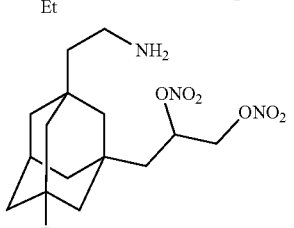
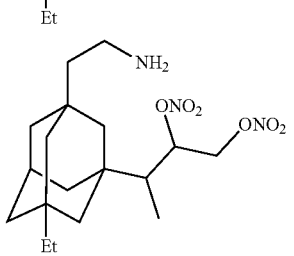

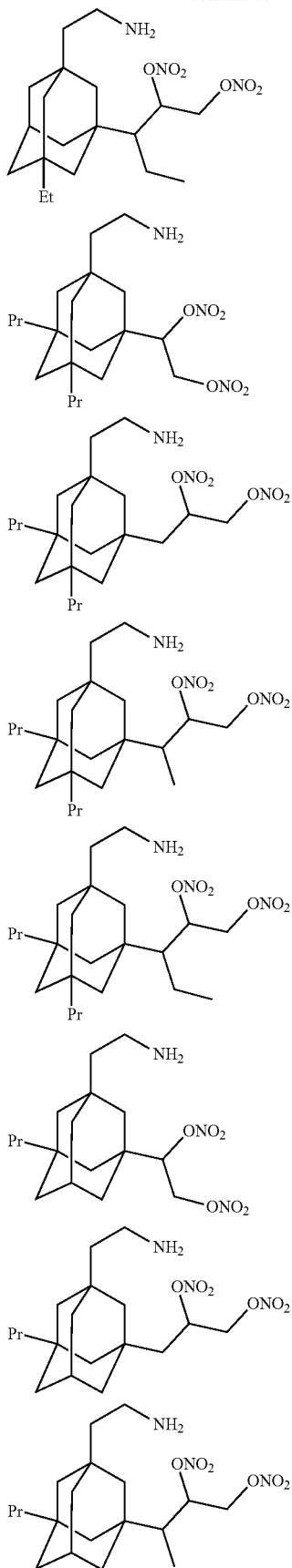

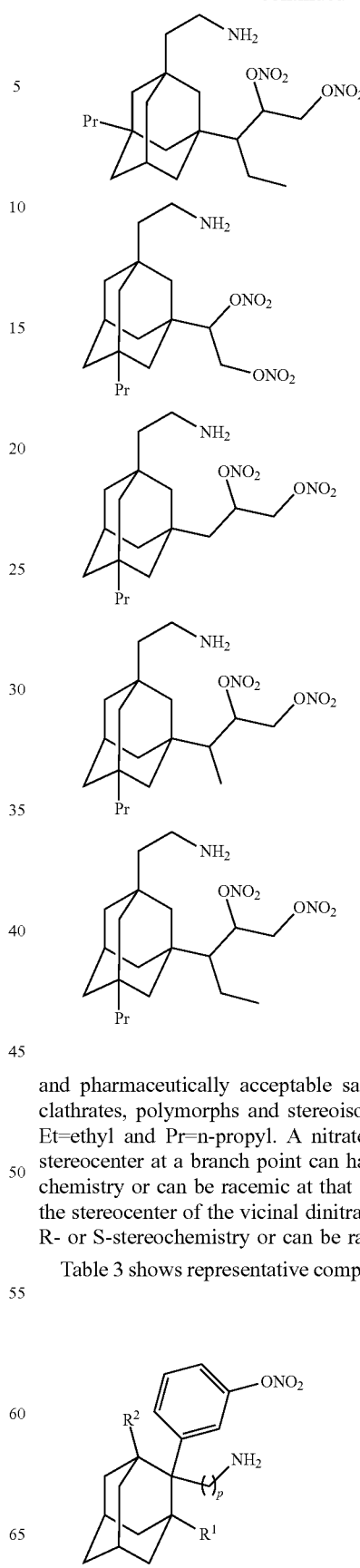

and pharmaceutically acceptable salts, solvates, hydrates, clathrates, polymorphs and stereoisomers thereof, wherein Et=ethyl and Pr=n-propyl. A nitrated alkyl group with a stereocenter at a branch point can have the R- or S-stereochemistry or can be racemic at that stereocenter. Likewise, the stereocenter of the vicinal dinitrate moiety can have the R- or S-stereochemistry or can be racemic.

Table 3 shows representative compounds of Formula IVA:

IVA-i

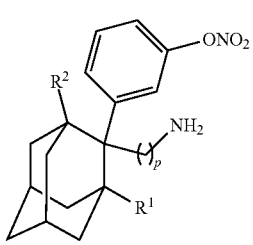

-continued

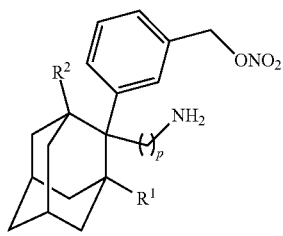

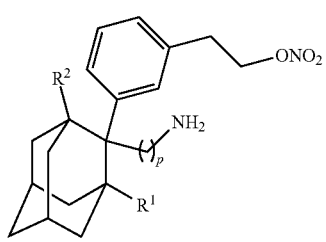

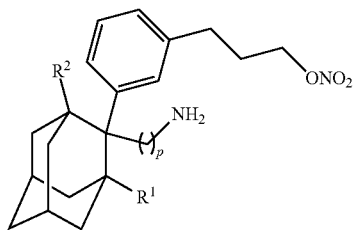

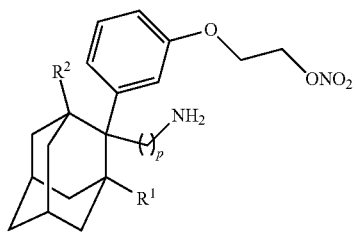

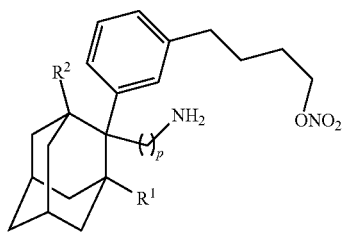

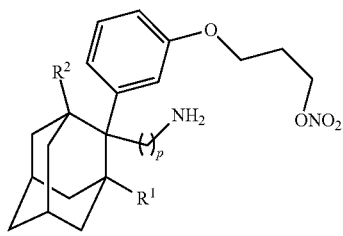

TABLE 3

For each subgenus IVA-i, IVA-ii, IVA-iii, IVA-iv, IVA-v, IVA-vi and IVA-vii

| | p | $R^1$ | $R^2$ |
|---|---|---|---|
| IVA-ii | 0, 1, 2 and 3 | hydrogen | hydrogen |
| | 0, 1, 2 and 3 | methyl | methyl |
| | 0, 1, 2 and 3 | hydrogen | methyl |
| | 0, 1, 2 and 3 | methyl | hydrogen |
| | 0, 1, 2 and 3 | ethyl | ethyl |
| IVA-iii | 0, 1, 2 and 3 | hydrogen | ethyl |
| | 0, 1, 2 and 3 | ethyl | hydrogen |
| | 0, 1, 2 and 3 | n-propyl | n-propyl |
| | 0, 1, 2 and 3 | hydrogen | n-propyl |
| | 0, 1, 2 and 3 | n-propyl | hydrogen |
| | 0, 1, 2 and 3 | isopropyl | isopropyl |
| | 0, 1, 2 and 3 | hydrogen | isopropyl |
| IVA-iv | 0, 1, 2 and 3 | isopropyl | hydrogen |
| | 0, 1, 2 and 3 | n-butyl | n-butyl |
| | 0, 1, 2 and 3 | hydrogen | n-butyl |
| | 0, 1, 2 and 3 | n-butyl | hydrogen |
| | 0, 1, 2 and 3 | isobutyl | isobutyl |
| | 0, 1, 2 and 3 | hydrogen | isobutyl |
| | 0, 1, 2 and 3 | isobutyl | hydrogen |
| IVA-v | 0, 1, 2 and 3 | sec-butyl | sec-butyl |
| | 0, 1, 2 and 3 | hydrogen | sec-butyl |
| | 0, 1, 2 and 3 | sec-butyl | hydrogen |
| | 0, 1, 2 and 3 | —$CH_2$—$ONO_2$ | —$CH_2$—$ONO_2$ |
| | 0, 1, 2 and 3 | hydrogen | —$CH_2$—$ONO_2$ |
| | 0, 1, 2 and 3 | —$CH_2$—$ONO_2$ | hydrogen |
| IVA-vi | 0, 1, 2 and 3 | —$(CH_2)_2$—$ONO_2$ | —$(CH_2)_2$—$ONO_2$ |
| | 0, 1, 2 and 3 | hydrogen | —$(CH_2)_2$—$ONO_2$ |
| | 0, 1, 2 and 3 | —$(CH_2)_2$—$ONO_2$ | hydrogen |
| | 0, 1, 2 and 3 | —$(CH_2)_3$—$ONO_2$ | —$(CH_2)_3$—$ONO_2$ |
| | 0, 1, 2 and 3 | hydrogen | —$(CH_2)_3$—$ONO_2$ |
| | 0, 1, 2 and 3 | —$(CH_2)_3$—$ONO_2$ | hydrogen |
| IVA-vii | 0, 1, 2 and 3 | —$CH_2CH(ONO_2)CH_3$ | —$CH_2CH(ONO_2)CH_3$ |
| | 0, 1, 2 and 3 | hydrogen | —$CH_2CH(ONO_2)CH_3$ |
| | 0, 1, 2 and 3 | —$CH_2CH(ONO_2)CH_3$ | hydrogen |
| | 0, 1, 2 and 3 | —$CH_2CH(CH_3)CH_2$—$ONO_2$ | —$CH_2CH(CH_3)CH_2$—$ONO_2$ |
| | 0, 1, 2 and 3 | hydrogen | —$CH_2CH(CH_3)CH_2$—$ONO_2$ |
| | 0, 1, 2 and 3 | —$CH_2CH(CH_3)CH_2$—$ONO_2$ | hydrogen | and pharmaceutically acceptable salts, solvates, hydrates, clathrates, polymorphs and stereoisomers thereof. The present disclosure specifically discloses each of the 1036 compounds shown in Table 3 and each of the possible stereoisomers thereof. An $R^1$ or $R^2$ group with a stereocenter can have the R- or S-stereochemistry or can be racemic at that stereocenter.

In certain embodiments, the compounds of Formula IVA are selected from:

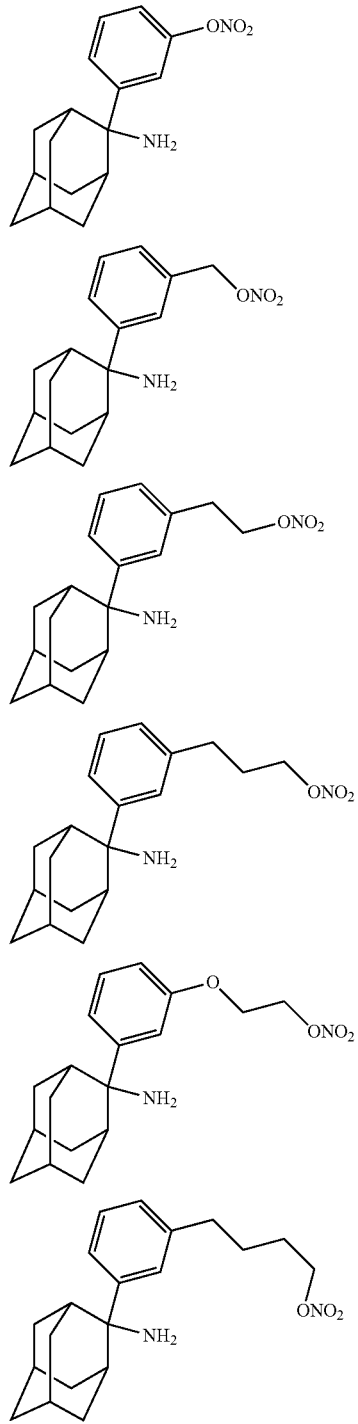

-continued

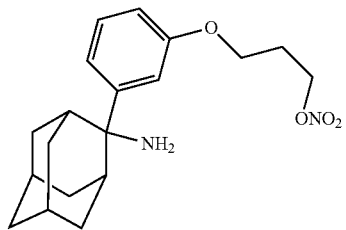

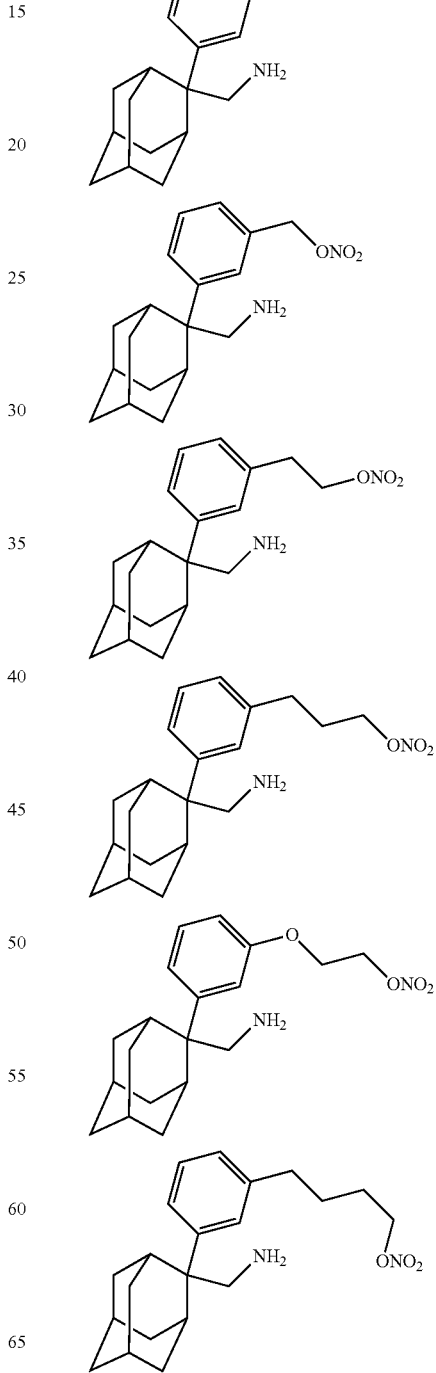

-continued
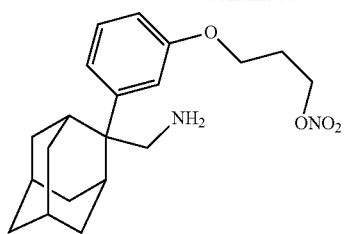
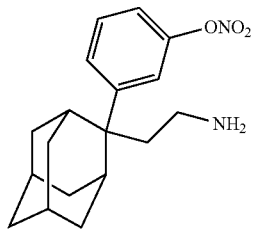
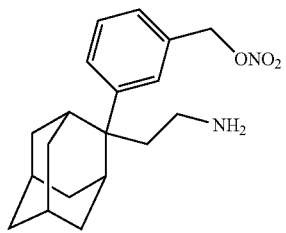
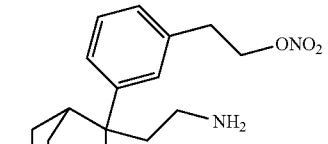
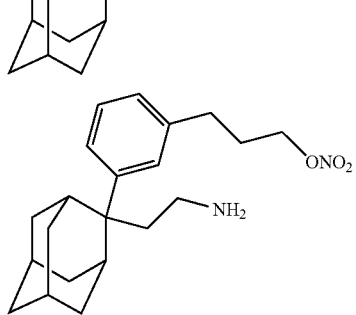
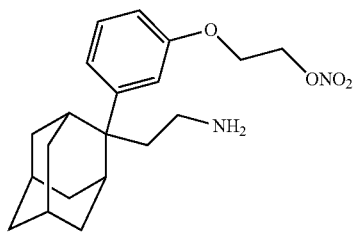
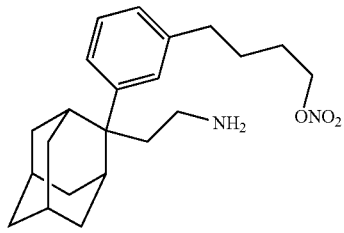
-continued
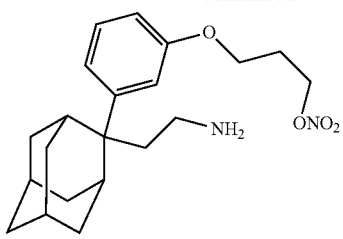
and pharmaceutically acceptable salts, solvates, hydrates, clathrates, polymorphs and stereoisomers thereof.
Table 4 shows representative compounds of Formula IVB:
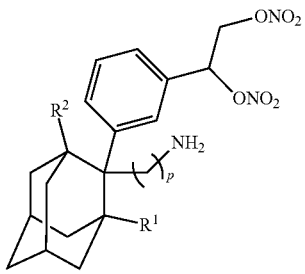
IVB-i
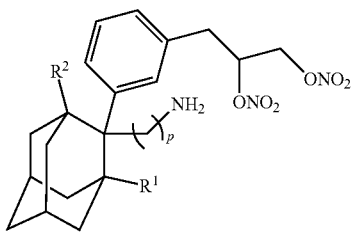
IVB-ii
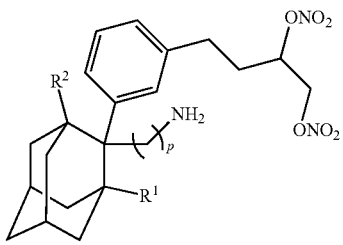
IVB-iii
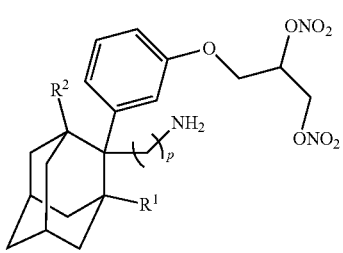
IVB-iv IVB-v

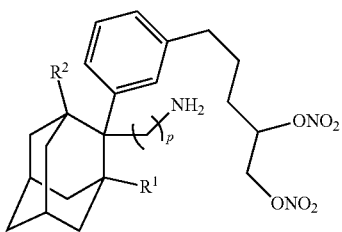

IVB-vi

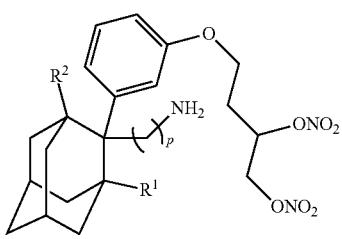

TABLE 4

| For each subgenus IVB-i, IVB-ii, IVB-iii, IVB-iv, IVB-v and IVB-vi | | |
|---|---|---|
| p | R¹ | R² |
| 0, 1, 2 and 3 | hydrogen | hydrogen |
| 0, 1, 2 and 3 | methyl | methyl |
| 0, 1, 2 and 3 | hydrogen | methyl |
| 0, 1, 2 and 3 | methyl | hydrogen |
| 0, 1, 2 and 3 | ethyl | ethyl |
| 0, 1, 2 and 3 | hydrogen | ethyl |
| 0, 1, 2 and 3 | ethyl | hydrogen |
| 0, 1, 2 and 3 | n-propyl | n-propyl |
| 0, 1, 2 and 3 | hydrogen | n-propyl |
| 0, 1, 2 and 3 | n-propyl | hydrogen |
| 0, 1, 2 and 3 | isopropyl | isopropyl |
| 0, 1, 2 and 3 | hydrogen | isopropyl |
| 0, 1, 2 and 3 | isopropyl | hydrogen |
| 0, 1, 2 and 3 | n-butyl | n-butyl |
| 0, 1, 2 and 3 | hydrogen | n-butyl |
| 0, 1, 2 and 3 | n-butyl | hydrogen |
| 0, 1, 2 and 3 | isobutyl | isobutyl |
| 0, 1, 2 and 3 | hydrogen | isobutyl |
| 0, 1, 2 and 3 | isobutyl | hydrogen |
| 0, 1, 2 and 3 | sec-butyl | sec-butyl |
| 0, 1, 2 and 3 | hydrogen | sec-butyl |
| 0, 1, 2 and 3 | sec-butyl | hydrogen |
| 0, 1, 2 and 3 | —CH₂—ONO₂ | —CH₂—ONO₂ |
| 0, 1, 2 and 3 | hydrogen | —CH₂—ONO₂ |

TABLE 4-continued

| For each subgenus IVB-i, IVB-ii, IVB-iii, IVB-iv, IVB-v and IVB-vi | | |
|---|---|---|
| p | R¹ | R² |
| 0, 1, 2 and 3 | —CH₂—ONO₂ | hydrogen |
| 0, 1, 2 and 3 | —(CH₂)₂—ONO₂ | —(CH₂)₂—ONO₂ |
| 0, 1, 2 and 3 | hydrogen | —(CH₂)₂—ONO₂ |
| 0, 1, 2 and 3 | —(CH₂)₂—ONO₂ | hydrogen |
| 0, 1, 2 and 3 | —(CH₂)₃—ONO₂ | —(CH₂)₃—ONO₂ |
| 0, 1, 2 and 3 | hydrogen | —(CH₂)₃—ONO₂ |
| 0, 1, 2 and 3 | —(CH₂)₃—ONO₂ | hydrogen |
| 0, 1, 2 and 3 | —CH₂CH(ONO₂)CH₃ | —CH₂CH(ONO₂)CH₃ |
| 0, 1, 2 and 3 | hydrogen | —CH₂CH(ONO₂)CH₃ |
| 0, 1, 2 and 3 | —CH₂CH(ONO₂)CH₃ | hydrogen |
| 0, 1, 2 and 3 | —CH₂CH(CH₃)CH₂—ONO₂ | —CH₂CH(CH₃)CH₂—ONO₂ |
| 0, 1, 2 and 3 | hydrogen | —CH₂CH(CH₃)CH₂—ONO₂ |
| 0, 1, 2 and 3 | —CH₂CH(CH₃)CH₂—ONO₂ | hydrogen | and pharmaceutically acceptable salts, solvates, hydrates, clathrates, polymorphs and stereoisomers thereof. The present disclosure specifically discloses each of the 888 compounds shown in Table 4 and each of the possible stereoisomers thereof. The stereocenter of the vicinal dinitrate moiety can have the R- or S-stereochemistry or can be racemic. Likewise, an R¹ or R² group with a stereocenter can have the R- or S-stereochemistry or can be racemic at that stereocenter.

In certain embodiments, the compounds of Formula IVB are selected from:

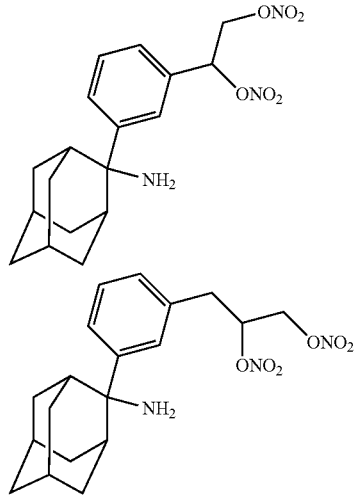

-continued
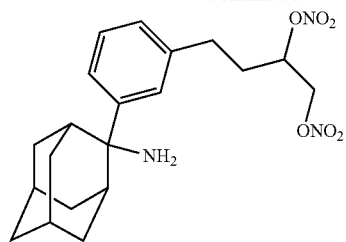
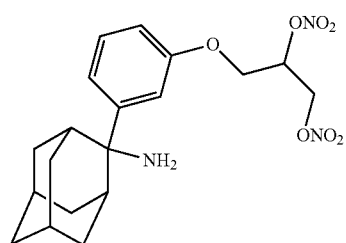
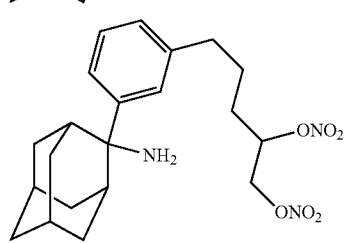
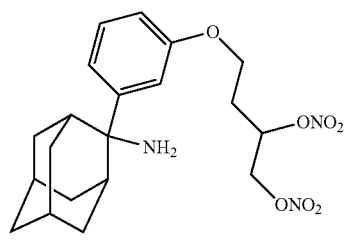
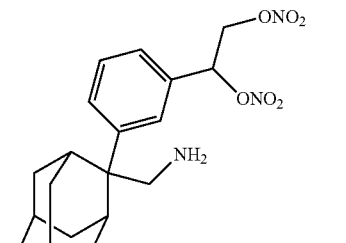
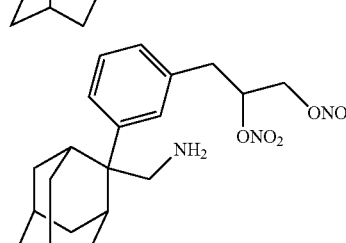
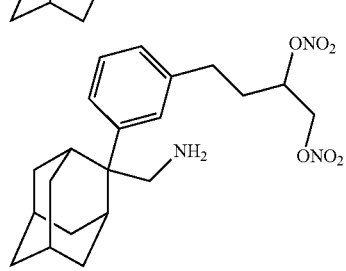
-continued
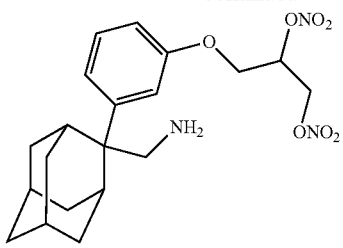
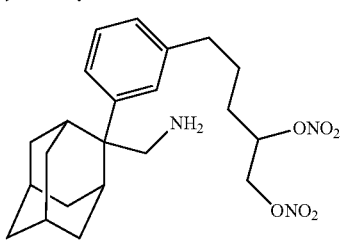
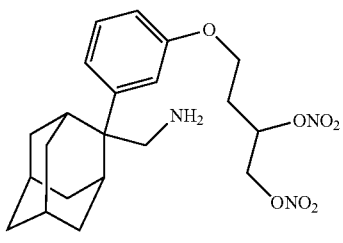
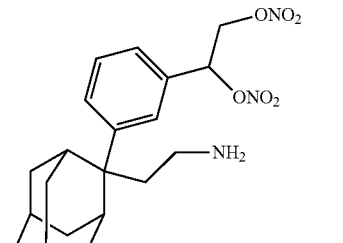
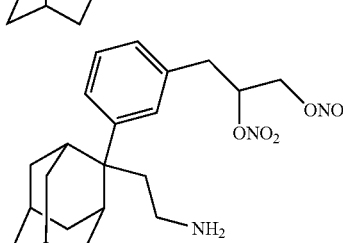
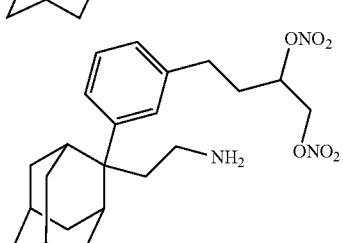
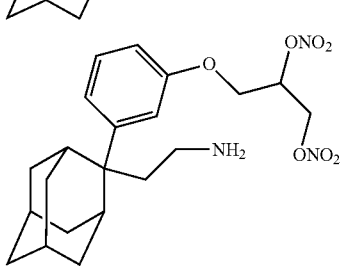

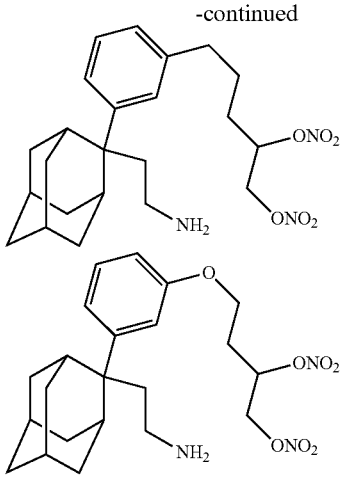

and pharmaceutically acceptable salts, solvates, hydrates, clathrates, polymorphs and stereoisomers thereof. The stereocenter of the vicinal dinitrate moiety can have the R- or S-stereochemistry or can be racemic.

Instead of being an amine group, the amine group indirectly or directly connected to the C-1 position of the aminoadamantyl nitrate compounds described herein can be an amide, carbamate or urea. The amine group of aminoadamantyl compounds, which is protonated at physiological pH, binds to the memantine/phencyclidine-binding site at or near the $Mg^{2+}$-binding site of open NMDAR channels by hydrogen bonding, with the protonated amine group acting as a hydrogen-bond donor and the side chain of asparagine at position 616 of the GluN1 (or NR1) subunit acting as a hydrogen-bond acceptor, as well as by electrostatic interaction with asparagine residues of the GluN2 (or NR2) subunit. An —NH(C=O)R amide, —NH(C=O)OR carbamate or —NHC(=O)$NR^aR^b$ urea group can also act as a hydrogen-bond donor. In some embodiments, the —$NR^3R^4$ moiety of aminoadamantyl nitrate compounds is —NH(C=O)$R^6$, —NH(C=O)$OR^6$ or —NHC(=O)$NR^7R^8$, wherein $R^6$ is hydrogen (for formamide) or linear or branched $C_1$-$C_6$ alkyl, and $R^7$ and $R^8$ independently are hydrogen or linear or branched $C_1$-$C_6$ alkyl, or $R^7$, $R^8$ and the nitrogen atom to which they are attached form a 3-6-membered ring. In certain embodiments, $R^6$ is hydrogen (for formamide) or linear or branched $C_1$-$C_3$ alkyl (e.g., methyl or ethyl), and $R^7$ and $R^8$ independently are hydrogen or linear or branched $C_1$-$C_3$ alkyl (e.g., methyl or ethyl).

IV. Salt Forms

The adamantyl compounds described herein have one or more amine groups (possibly unless the amine group indirectly or directly connected to the C-1 position of the adamantyl scaffold is an amide, carbamate or urea) and can exist as a free base or as salts. They can be used or administered as a free base or as pharmaceutically acceptable salts. An amine group can form an addition salt with an acid, such as a mineral acid (e.g., HCl, HBr, HI, nitric acid, phosphoric acid or sulfuric acid) or an organic acid (e.g., a carboxylic acid or a sulfonic acid). Suitable acids for use in the preparation of pharmaceutically acceptable salts include without limitation acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, D-gluconic acid, D-glucuronic acid, L-glutamic acid, alpha-oxoglutaric acid, glycolic acid, hippuric acid, hydrobromic acid, hydrochloric acid, hydroiodic acid, (±)-DL-lactic acid, (+)-L-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, propionic acid, L-pyroglutamic acid, pyruvic acid, saccharic acid, salicylic acid, 4-amino-salicylic acid, sebacic acid, stearic acid, succinic acid, sulfuric acid, tannic acid, (±)-DL-tartaric acid, (+)-L-tartaric acid, thiocyanic acid, p-toluenesulfonic acid, undecylenic acid, and valeric acid.

If a compound has an acidic group (e.g., a carboxyl group), the acidic group can form an addition salt with a base. Pharmaceutically acceptable base addition salts can be formed with, e.g., metals (e.g., alkali metals or alkaline earth metals) or amines (e.g., organic amines). Examples of metals useful as cations include without limitation alkali metals (e.g., lithium, sodium, potassium and cesium), alkaline earth metals (e.g., magnesium, calcium and barium), aluminum and zinc. Metal cations can be provided by way of, e.g., inorganic bases, such as hydroxides, carbonates and hydrogen carbonates. Non-limiting examples of organic amines useful for forming base addition salts include chloroprocaine, choline, cyclohexylamine, dibenzylamine, N,N'-dibenzylethylenediamine, dicyclohexylamine, diethanolamine, ethylenediamine, N-ethylpiperidine, histidine, isopropylamine, N-methylglucamine, procaine, pyrazine, triethylamine, trimethylamine and tromethamine. Pharmaceutically acceptable salts are discussed in detail in Handbook of Pharmaceutical Salts, Properties, Selection and Use, P. Stahl and C. Wermuth, Eds., Wiley-VCH (2011).

In some embodiments, the aminoadamantyl nitrate compounds described herein are used or administered in the form of pharmaceutically acceptable salts. In certain embodiments, the aminoadamantyl nitrate compounds are used or administered as a hydrochloride (HCl) or hydrobromide (HBr) salt.

V. Isotopologues, Including Deuterated Compounds

The present disclosure encompasses all isotopically enriched forms of the aminoadamantyl nitrate compounds described herein, including without limitation those enriched in the content of $^2H$ (deuterium), $^{13}C$, $^{15}N$, $^{17}O$ or $^{18}O$, or any combination thereof, at one or more, or all, instances of the corresponding atom(s).

To eliminate foreign substances such as drugs, the animal body expresses a variety of enzymes, such as cytochrome $P_{450}$ enzymes, esterases, proteases, reductases, dehydrogenases and monoamine oxidases, which react with and convert the foreign substances to more polar intermediates or metabolites for renal excretion. Such metabolic reactions can involve the oxidation of a carbon-hydrogen (C—H) bond to a carbon-oxygen (C—O) bond or a carbon-carbon (C=C) pi bond, or a carbon-oxygen (C—O) single bond to a carbon-oxygen (C=O) double bond. The resulting metabolites may be stable or unstable under physiological conditions, and may have substantially different pharmacologic, pharmacokinetic and pharmacodynamic properties and toxicity profiles compared to the parent compounds. For many drugs, such metabolic oxidations can be rapid and lead to the requirement of higher dosage amounts or/and increased dosing frequencies, which can result in greater side effects.

The disclosure provides isotopologues corresponding to the aminoadamantyl nitrate compounds described herein which are enriched with deuterium (deuterated) at one or more positions. Deuteration at one or more positions can have any one or more, or all, of the following benefits: (1) a longer half-life; (2) decreased amount of a dose or/and decreased number of doses needed to achieve a desired effect; (3) decreased variation between subjects in the blood or plasma level of the parent drug; (4) increased efficacy; (5) reduced side effects due to decreased amount of the parent drug administered or/and decreased production of deleterious metabolites; and (6) increased maximum tolerated dose.

Deuterium can be substituted for hydrogen at any one or more, or all, of the available positions in an aminoadamantyl nitrate compound, including without limitation at any one or more, or all, of the available positions in the adamantyl scaffold, the alkyl group connecting the amine group to the C-1 position of the adamantyl scaffold (unless the amine group is directly connected to the C-1 position), the X group (unless X is a bond), the $R^1$ group (unless $R^1$ is halide), the $R^2$ group (unless $R^2$ is halide), or the phenyl ring of a compound of Formula II, III or IV, or any combination thereof. In certain embodiments, an aminoadamantyl nitrate compound is deuterated at the carbon atom attached to the amine group that is indirectly connected to the C-1 position of the adamantyl scaffold (unless the amine group is directly connected to the C-1 position), or/and is deuterated at the carbon atom attached to a nitrate group for one or more, or all, nitrate groups depending on whether the compound has one or more nitrate groups (unless the compound has only one nitrate group and X is a bond). In further embodiments, an aminoadamantyl nitrate is deuterated at one or more, or all, of the available positions in the $R^1$ group (unless $R^1$ is halide) or/and the $R^2$ group (unless $R^2$ is halide).

In some embodiments, at least one of the available positions in an aminoadamantyl nitrate has deuterium enrichment of at least about 10%, 25%, 50%, 75%, 90%, 95% or 98%. In certain embodiments, at least one of the available positions has deuterium enrichment of at least about 90%, 95% or 98%. In further embodiments, each position in an aminoadamantyl nitrate enriched with deuterium (or deuterated) independently has deuterium enrichment of at least about 10%, 25%, 50%, 75%, 90%, 95% or 98%. In certain embodiments, each position enriched with deuterium (or deuterated) independently has deuterium enrichment of at least about 90%, 95% or 98%.

The term "deuterium enrichment" refers to the percentage of incorporation of deuterium at a given position in a molecule in place of hydrogen. For example, deuterium enrichment of 10% at a given position means that 10% of molecules in a given sample contain deuterium at that position. Because the naturally occurring distribution of deuterium is about 0.0156%, deuterium enrichment at any position in a molecule synthesized using non-deuterium-enriched starting materials or reagents is about 0.0156%. Deuterium enrichment can be determined using conventional analytical methods known to one of ordinary skill in the art, including mass spectrometry and nuclear magnetic resonance spectroscopy.

The term "is deuterium" or "is deuterated", when used to describe a given position in a molecule, or the symbol "D", when used to represent an element at a given position in a drawing of a molecular structure, means that the specified position is enriched with deuterium above the naturally occurring distribution of deuterium. In some embodiments, deuterium enrichment is at least about 10%, 20%, 30%, 40%, 50%, 60%, 70%, 80%, 90%, 95%, 98% or 99% (e.g., at least about 50%) of deuterium at the specified position. In certain embodiments, deuterium enrichment is at least about 90%, 95% or 98% of deuterium at the specified position.

VI. Therapeutic Uses of Aminoadamantyl Nitrate Compounds

Overactivation of the NMDA receptor, relieving the voltage-dependent channel block by $Mg^{2+}$ and causing excessive influx of $Ca^{2+}$ and subsequent oxidative stress due to overproduction of reactive oxygen species, can lead to neuronal excitotoxicity and ultimately neuronal injury and death. Without intending to be bound by theory, it is believed that stimulation of extrasynaptic NMDA receptors (eNMDAR) rather than synaptic NMDA receptors (sNMDAR) is responsible for excitotoxicity implicated in neurodegenerative disorders. Synaptic NMDAR activity is phasic by nature and synaptic NMDARs generally are transiently and intensely activated by trans-synaptic release of glutamate. By contrast, extrasynaptic NMDARs typically are activated chronically by elevated levels of ambient glutamate, whether resulting from synaptic release of glutamate or/and impairment or reversal of uptake of glutamate [G. Hardingham et al., *Nat. Rev. Neurosci.*, 11:682-696 (2010)]. Because synaptic NMDARs typically are phasically/transiently activated while extrasynaptic NMDARs typically are chronically/tonically activated, it is primarily extrasynaptic NMDARs that are excessively activated and hence allow an excessive and prolonged influx of $Ca^{2+}$ through the excessively/persistently open ion channel. Furthermore, under conditions of chronic NMDAR activation such as excessive levels of glutamate or NMDA, synaptic NMDAR activity is suppressed and extrasynaptic NMDAR signaling pathways dominate [F. Soriano et al., *J Neurosci.*, 26:4509-4518 (2006)].

Synaptic NMDAR activity promotes cell health and survival, whereas extrasynaptic NMDAR activity initiates cell-death pathways and antagonizes synaptic NMDAR-induced cell-survival pathways. $Ca^{2+}$ influx evoked by intense activation of synaptic NMDARs causes no perturbation to mitochondrial membrane potential and enhances mitochondrial health, and triggers genomic processes primarily via nuclear $Ca^{2+}$ signaling that render neurons more resistant to oxidative stress and apoptosis (including decreased expression of pro-apoptotic factors such as caspases). An episode of synaptic NMDAR activity promotes "acquired" neuroprotection that lasts after most signaling pathways are no longer active. In contrast, comparable intracellular $Ca^{2+}$ concentrations induced by activation of extrasynaptic NMDARs—either on their own or in the presence of activation of synaptic NMDARs—trigger nitochondrial dysfunction (including loss of mitochondrial membrane potential) and cell death (whether by apoptosis or necrosis). Mitochondrial dysfunction, activation of the intrinsic mitochondrial apoptotic pathway, and oxidative stress due to overproduction of reactive oxygen species are implicated in the pathogenesis of neurodegenerative diseases. The stark differences in the outcome from activation of synaptic NMDARs and extrasynaptic NMDARs result from opposing effects on intracellular signaling pathways, many involving the same signal proteins, and induction of very different programs of gene expression. Nuclear $Ca^{2+}$, an important regulator of gene expression, plays a key role in the pro-survival effects of synaptic NMDAR activation and is disrupted by extrasynaptic NMDAR activity. Many neurodegenerative disorders and other CNS disorders share common signaling pathways downstream of extrasynaptic NMDAR activity which contribute to neurotoxicity. See, e.g., Hardingham (2010, supra) and M. Parsons et al., *Neuron*, 82:279-293 (2014).

Activation of extrasynaptic NMDA receptors rather than synaptic NMDA receptors is believed to be responsible for excitotoxicity implicated in neurodegenerative disorders such as Alzheimer's disease, Huntington's disease, Parkinson's disease and amyotrophic lateral sclerosis, and in other CNS disorders such as epilepsy, stroke and traumatic brain injury [Hardingham (2010, supra) and Parsons (2014, supra)]. Extrasynaptic NMDAR expression or/and activation are elevated in disease states [Parsons (2014, supra)]. In a study relating to Alzheimer's disease (AD), the amyloid-$\beta_{1-42}$ peptide stimulates the $\alpha$-7 nicotinic acetylcholine receptor and hence the release of an excessive amount of glutamate from astrocytes, which in turn activates neuronal extrasynaptic NMDARs that mediate nitric oxide production, tau hyperphosphorylation, caspase-3 activation and mitochondrial dysfunction, resulting in neuronal spine loss and loss of synapses associated with cognitive decline in AD [M. Talantova et al., *Proc. Nat. Acad. Sci. USA*, 110:E2518-E2527 (2013)]. Loss of synapses can cause an imbalance of synaptic NMDAR and extrasynaptic NMDAR activity and signaling that can lead to cell death associated with neurodegenerative diseases such as Alzheimer's disease and Huntington's disease.

In addition to the location of NMDARs, the subunit composition of NMDARs may play an important role in the biological activity of NMDARs. NMDARs assemble as heterotetramers having two obligatory GluN1 subunits and two GluN2 (GluN2A, 2B, 2C or 2D) or/and GluN3 (GluN3A or 3B) subunits. The large majority of NMDARs in the CNS assemble as a GluN1/GluN2A or GluN1/GluN2B diheteromer, or as a GluN1/GluN2A/GluN2B triheteromer. Although both subtypes can be found synaptically and extrasynaptically, the GluN2A (or NR2A) subtype is enriched in synaptic NMDARs, while the GluN2B (or NR2B) subtype is more prevalent in extrasynaptic NMDARs [L. Groc et al., *Proc. Natl. Acad. Sci. USA*, 103:18769-18774 (2006); and M. Martel et al., *Neurosci.*, 158:334-343 (2009)]. GluN2A-containing NMDARs are associated with cell survival, whereas GluN2B-containing NMDARs are linked to cell death [T. Lai et al., *Trends Mol. Med.*, 17:266-275 (2011)]. Furthermore, intracellular signaling via the GluN2B C-terminal domain is a large contributor to NMDA-induced excitotoxicity [M. Martel et al., *Neuron*, 74:543-556 (2012)].

Neurodegenerative and other CNS disorders associated with excitotoxic events can be treated through blockade of extrasynaptic NMDARs. The physiological activity of synaptic NMDARs is essential for normal neuronal function, so an NMDAR antagonist needs to block activated extrasynaptic NMDARs without suppressing the normal activity of synaptic NMDARs. This can be achieved by an uncompetitive antagonist, or open channel blocker, that selectively enters the opened channel of extrasynaptic NMDARs after they have been activated by the binding of co-agonists and thereby blocks the flow of cations, in particular $Ca^{2+}$.

The aminoadamantyl nitrate compounds described herein act as voltage-dependent, uncompetitive antagonists that selectively block extrasynaptic NMDARs. They have a relatively low affinity for, and a relatively fast off rate from, the memantine/phencyclidine-binding site at or near the $Mg^{2+}$-binding site in the channel of activated NMDARs so that they do not accumulate in the channel when it closes and hence preserve the physiological activity of phasically activated synaptic NMDARs and avoid psychiatric side effects associated with high-affinity NMDAR antagonists [S. Lipton, *Curr. Drug Targets*, 8:621-632 (2007)]. However, the aminoadamantyl nitrate compounds have a sufficiently high affinity (e.g., a KI from about 200 nM to about single-digit $\mu$M) for the memantine/phencyclidine-binding site and a sufficiently long dwell time in the excessively/persistently open ion channel of tonically activated extrasynaptic NMDARs so that they block excessive influx of $Ca^{2+}$ through the channel and thereby prevent excitotoxic events. Whether administered as an acid addition salt or a free base, the amine group of the adamantyl compounds is protonated at physiological pH (pH of about 7.4). The protonated amine group binds at or near the $Mg^{2+}$-binding site in the channel of activated NMDARs with a higher affinity, a slower off/dissociation rate and lesser voltage dependence than $Mg^{2+}$ does at the $Mg^{2+}$-binding site, allowing the adamantyl compounds to block prolonged influx of $Ca^{2+}$ through the channel. The protonated amine group forms a hydrogen bond with the side chain of asparagine at position 616 of the GluN1 (or NR1) subunit at the narrowest constriction of the pore (the channel selectivity filter), and also has significant electrostatic interaction with the carbonyl oxygen atom of the side chain of asparagine residues at the N and N+1 sites of the GluN2 (or NR2) subunit there [H.-S. Chen et al., *J. Pharmacol. Exper. Therap.*, 314:961-971 (2005)]. The $Mg^{2+}$-binding site is within the electric field of the channel, so blockade of the channel by a (positively) charged agent binding at or near the $Mg^{2+}$-binding site is voltage-dependent.

Increased binding affinity of the aminoadamantyl nitrate compounds for extrasynaptic NMDARs is also provided by hydrophobic interaction between the compounds and the subunits of extrasynaptic NMDARs. The two methyl groups of memantine engage in hydrophobic interaction with hydrophobic binding pockets formed by the residues A645 and A644 in the third transmembrane helix of the GluN1 (or NR1) subunit and the GluN2B (or NR2B) subunit, respectively, which greatly increases memantine's binding affinity for activated NMDARs compared to that of amantadine [W. Limapichat et al., *ACS Chem. Neurosci.*, 4:255-260 (2013)]. The GluN2B (or NR2B) subtype is more prevalent in extrasynaptic NMDARs. Aminoadamantyl nitrate compounds having a non-hydrogen (e.g., alkyl) group for $R^1$ and $R^2$ can engage in hydrophobic interaction with the hydrophobic binding pockets of the GluN1 and GluN2B subunits of extrasynaptic NMDARs. The $R^1$ group is believed to be oriented toward the hydrophobic binding pocket of GluN2B. A greater number of carbon atoms of a group increases its hydrophobicity/lipophilicity.

The aminoadamantyl nitrate compounds described herein selectively inhibit activated extrasynaptic NMDARs and possess a dual mechanism of inhibition. They block the open ion channel of activated extrasynaptic NMDARs in a voltage-dependent manner by binding at or near the $Mg^{2+}$-binding site in the channel, and they suppress the activity of activated extrasynaptic NMDARs in a voltage-independent manner by S-nitrosylation of cysteine residues of a redox modulatory site on the receptor. The ion-channel conductivity of NMDA receptors is regulated by nitrosylation [Y. Choi et al., *Nat. Neurosci.*, 3:15-21 (2000)]. Binding of the protonated amine group of an aminoadamantyl nitrate at or near the $Mg^{2+}$-binding site in the open ion channel of activated extrasynaptic NMDARs brings a nitrate group of the compound in close proximity to cysteine residues of a redox modulatory site in the extracellular domain of the receptor. Oxidation at the redox site, possibly resulting in the formation of one or more disulfide bonds involving two or more cysteine residues, downregulates/desensitizes NMDAR channel activity. The nitrate group of the aminoadamantyl compound donates/transfers NO (e.g., in the form of $NO^+$) to a cysteine residue of the redox site, possibly with the aid of glutathione S-transferase. If the aminoadamantyl compound has two or more nitrate groups, two or more nitrate groups can potentially transfer NO to two or more of about five cysteine residues of the redox site. S-nitrosylation of cysteine residue(s) oxidizes the sulfhydryl group of the cysteine residue(s), or may facilitate the formation of disulfide bond(s). The effect of S-nitrosylation of cysteine residue(s) of the redox site is suppression of the activity of, and $Ca^{2+}$ influx through, extrasynaptic NMDAR channels. In neurons, nitric oxide synthase (NOS) is activated by the influx of $Ca^{2+}$ through NMDAR channels, resulting in nitric oxide (NO) production. NO downregulates NOS and inhibits $Ca^{2+}$ influx through NMDAR channels via negative feedback. Targeting of the NO-donating nitrate group(s) of the aminoadamantyl compound to the cysteine residues of the redox site avoids potential vascular and neurotoxic side effects of free nitric oxide, such as vasodilation, apoptosis and formation of neurotoxic peroxynitrite. After donation of NO for S-nitrosylation, the resulting protonated aminoadamantyl compound with a hydroxyl group in place of each donor nitrate group remains bound at or near the $Mg^{2+}$-binding site, unless its voltage-gated blockade of the ion channel is attenuated by membrane depolarization. However, the redox modulatory site is outside of the voltage field of the channel, and hence suppression of the channel activity of activated extrasynaptic NMDARs by S-nitrosylation of cysteine residues of the redox site is voltage-independent and remains for a significant amount of time after the compound is expelled from the channel by depolarization. Inhibition of activated extrasynaptic NMDARs via S-nitrosylation of cysteine residues markedly increases under hypoxic condition, and thus is particularly suited for, but not limited to, preventing or reducing neuronal damage due to cerebral ischemia such as stroke and vasular dementia [H. Takahashi et al., *Sci. Rep.*, 5:14781 (2015)].

The aminoadamantyl nitrate compounds described herein selectively inhibit activated extrasynaptic NMDARs and thereby prevent or curtail excitotoxicity while sparing normal synaptic NMDAR activity. Sparing the NMDAR component of excitatory postsynaptic currents (EPSCs) is neurotrophic and avoids synaptic injury. Like nitromemantine, the aminoadamantyl nitrate compounds described herein have at least one nitrate group. Memantine preferentially blocks the excessively open channel of activated extrasynaptic NMDARs while relatively sparing normal synaptic NMDAR activity, even under conditions of pathological depolarization in the presence of extracellular $Mg^{2+}$[P. Xia et al., *J. Neurosci.*, 30:11246-11250 (2010)]. Nitromemantine inhibits extrasynaptic NMDAR activity more selectively and spares synaptic NMDAR activity to a greater degree than memantine [Takahashi (2015, supra)]. Selective inhibition of extrasynaptic NMDARs results in greater neuroprotection and less side effects than uncompetitive antagonists that block both synaptic NMDARs and extrasynaptic NMDARs (e.g., high-affinity NMDAR antagonists) or are less selective for the latter (e.g., memantine). The aminoadamantyl nitrate compounds described herein can prevent or reduce loss of synapses and death of neurons, increase synaptic and dendritic density, and enhance the cognitive function of Alzheimer's patients by antagonizing extrasynaptic NMDARs as well as the α-7 nicotinic acetylcholine receptor with, e.g., chronic treatment. Furthermore, the aminoadamantyl nitrate compounds can stimulate regrowth of synapses and restore lost synapses with, e.g., prolonged administration.

In addition, the aminoadamantyl nitrate compounds described herein can promote long-term potentiation (LTP) underlying synaptic plasticity and hence memory and learning. Synaptic plasticity is the ability of chemical synapses to change their strength, and permits regulated strengthening or weakening of specific connections in an organized fashion. Memories are believed to be encoded by modification of synaptic strength. LTP is a persistent strengthening of synapses based on recent patterns of synaptic activity that produce a long-lasting increase in signal transmission between two neurons, a process believed to encode and store learning and long-term memory. The opposite of LTP is long-term depression (LTD), which produces a long-lasting decrease in synaptic strength. Activation of synaptic NMDA receptors induces LTP, and their inhibition impairs LTP [Parsons (2014, supra)]. In contrast, activation of extrasynaptic NMDA receptors inhibit LTP and induce LTD [Li et al., *J. Neurosci.*, 31:6627-6638 (2011); and Liu et al., *Brain Res. Bull.*, 93:10-16 (2013)]. By selectively antagonizing activated extrasynaptic NMDARs while not interfering with physiological synaptic NMDAR activity, the aminoadamantyl nitrate compounds can promote or spare LTP and prevent or curtail LTD, and thereby can restore synaptic plasticity and enhance cognitive function. Moreover, the compounds can aid recovery of synaptic function and thereby improve impaired memory and learning.

Many neurodegenerative disorders and other CNS disorders share common signaling pathways downstream of extrasynaptic NMDAR activity which contribute to neuronal dysfunction, damage and death. As selective uncompetitive antagonists of activated extrasynaptic NMDARs, the aminoadamantyl nitrate compounds described herein can be used to treat a wide variety of neurodegenerative disorders and other CNS disorders. Non-limiting examples of neurodegenerative disorders that can be treated with the aminoadamantyl nitrate compounds described herein include dementia (e.g., Alzheimer's disease, vascular dementia, dementia with Lewy bodies, frontotemporal dementia and HIV-associated dementia), Huntington's disease (which often leads to dementia), Parkinson's disease (which often leads to dementia), multiple system atrophy (Shy-Drager syndrome), cerebellar degeneration, ataxia (e.g., cerebellar ataxia, spinocerebellar ataxia, Friedreich's ataxia and ataxia-telangiectasia [Louis-Bar syndrome]), motor neuron diseases (e.g., amyotrophic lateral sclerosis [ALS], primary lateral sclerosis [PLS], progressive muscular atrophy [PMA] and spinal muscular atrophy [SMA]), multiple sclerosis, vision impairment or loss caused by neurodegeneration of the visual pathway (e.g., optic neuropathy/atrophy, glaucoma and age-related macular degeneration [AMD]), and sensorineural hearing loss. See, e.g., Hardingham (2010, supra); Parsons (2014, supra); A. Kritis et al., *Front. Cell. Neurosci.*, 9:91 (2015); A. Iizuka et al., *Neurosci. Lett.*, 592:37-41 (2015); S. Rossi et al., *PLOS One*, 8:e67357-e67369 (2013); N. Osborne et al., *Br. J. Ophthalmol.*, 83:980-986 (1999); and V. Kotak et al., *J. Neurosci.*, 25:3908-3918 (2005).

In certain embodiments, the aminoadamantyl nitrate compounds described herein are used to treat a neurodegenerative disorder selected from Alzheimer's disease, vascular dementia, Huntington's disease, Parkinson's disease and ALS.

Examples of other CNS disorders, which may or may not involve neurodegeneration in their pathophysiology, that can be treated with the aminoadamantyl nitrate compounds described herein include without limitation cerebrovascular disorders (including brain ischemia [including acute ischemia such as stroke, chronic ischemia such as vascular dementia, cerebral ischemia/reperfusion injury, and neurological damage caused by low oxygen or/and glucose levels in the brain], intracerebral hemorrhage and retinopathy), brain injury and trauma (including traumatic brain injury, diffuse axonal injury, primary and secondary brain injury, focal and diffuse brain injury, anoxic and hypoxic brain injury, intracerebral hemorrhage and brain edema), spinal cord injury (due to, e.g., trauma, ischemia or a degenerative disorder), epilepsy (including neurological damage caused by epileptic seizures), dyskinesia (e.g., levodopa-induced dyskinesia and tardive dyskinesia), spasticity, pain (e.g., acute pain, chronic pain, allodynia, complex regional pain syndrome [CRPS], fibromyalgia, hyperalgesia, inflammatory pain, neuropathic pain, postoperative pain, cancer-related pain, drug-induced pain and injury-induced pain), headaches (including primary headaches [e.g., migraine, cluster headache and tension headache] and secondary headaches [due to, e.g., a cerebrovascular disorder, a brain bleed, a brain injury, a brain infection or a brain tumor), neurodevelopmental disorders (including MEF2C haploinsufficiency syndrome [MCHS], autism spectrum disorder [including autism], developmental delay, intellectual disability, fragile X syndrome, attention-deficit hyperactivity disorder [ADHD] and schizophrenia), mood disorders (including depressive disorders [e.g., major depressive disorder and treatment-resistant depression], bipolar disorders and dementia-related mood disorders), and anxiety disorders (including generalized anxiety disorder, stress disorders [e.g., acute stress disorder, post-traumatic stress disorder and chronic stress], and obsessive-compulsive disorder). See, e.g., Hardingham (2010); Parsons (2014); S. Ivanova et al., *Parkinsons Dis.*, 2016:6461907 (2016); C. Woolf, *Pain*, 152:S2-15 (2011); M. Zhuo, *Neuropharmacol.*, 112:228-234 (2017); X. Moisset et al., *Headache*, 57:1261-1264 (2017); L. Huang et al., *Ann. Pharmacother.*, 48:1507-1511 (2014); C. Hu et al., *J. Pharmacol. Sci.*, 132:115-121 (2016); D. Rossignol et al., *Front. Pediatrics*, 2:87 (2014); S. Tu et al., *Nat. Commun.*, 8:1488 (2017); A. Toft et al., *J Neurosci.*, 36:9817-9827 (2016); M. Ghasemi et al., *Neurosci. Biobehav. Rev.*, 80:555-572 (2017); E. Lang et al., *Neurosci. Biobehav. Rev.*, S0149-7634:30322-30326 (2017); C. Kraus et al., *Int. J. Psychiatry Clin. Pract.*, 21:2-12 (2017); T. Schwartz et al., *Case Rep. Psychiatry*, 2012:749796 (2012); and N. Li et al., *Biol. Psychiatry*, 69:754-761 (2011).

In certain embodiments, the aminoadamantyl nitrate compounds described herein are used to treat a CNS disorder selected from brain ischemia, traumatic brain injury, epilepsy, pain and autism spectrum disorder.

The therapeutically effective amount and the frequency of administration of an aminoadamantyl nitrate compound to treat a neurodegenerative or other CNS disorder may depend on various factors, including the type of disorder, the severity of the condition, the potency of the compound, the mode of administration, the age, body weight, general health, gender and diet of the subject, and the response of the subject to the treatment, and can be determined by the treating physician. In some embodiments, the effective dose of an aminoadamantyl nitrate per day is from about 1, 5 or 10 mg to about 100 mg, or as deemed appropriate by the treating physician, which can be administered in a single dose or in divided doses. In certain embodiments, the effective dose of an aminoadamantyl nitrate per day is from about 5 or 10 mg to about 50 mg, or about 50-100 mg. In further embodiments, the effective dose of an aminoadamantyl nitrate per day is about 1, 5, 10, 15, 20, 25, 30, 40, 50, 60, 70, 80, 90 or 100 mg. In certain embodiments, the effective dose of an aminoadamantyl nitrate per day is about 10-30 mg, or about 10, 15, 20, 25 or 30 mg.

The dosage of an aminoadamantyl nitrate can be adjusted during the course of the treatment regimen, which can be determined by the treating physician. For example, an aminoadamantyl nitrate compound can be adminstered in an initial daily dose for the first week of treatment, and then the daily dose of the compound can be gradually or step-wise increased for every subsequent week of treatment until a target or suitable daily maintenance dose is administered for, e.g., the fourth week of treatment and thereafter for the duration of treatment. Increasing the dose of a drug gradually or step-wise during the initial phase of treatment would allow the treating physician to determine the optimum therapeutic dose while avoiding or minimizing any potential side effect, for example. The initial doses and the maintenance dose can be any effective dose described herein. As another example, if it is desired to establish a therapeutic level of an aminoadamantyl nitrate compound quickly for the treatment of a CNS disorder, such as a stroke, a traumatic brain injury or pain, a first loading dose of the compound can be administered on, e.g., day 1, an optional second loading dose can be administered on, e.g., day 2, an optional third loading dose can be administered on, e.g., day 3, and a maintenance dose of the compound can be administered daily thereafter for the duration of treatment. A loading dose can be, e.g., about 5, 4, 3, 2.5, 2 or 1.5 times larger than the maintenance dose, and the optional second and third loading doses can be, e.g., smaller than the previous loading dose. The maintenance dose can be any effective dose described herein.

An aminoadamantyl nitrate can be administered in any suitable frequency to treat a neurodegenerative or other CNS disorder, which can be determined by the treating physician. In some embodiments, an aminoadamantyl nitrate is administered daily (including one, two or more times daily), every two days, every three days or weekly, or as deemed appropriate by the treating physician. In certain embodiments, an aminoadamantyl nitrate is administered once daily.

An aminoadamantyl nitrate can be administered for any suitable period of time to treat a neurodegenerative or other CNS disorder, which can be determined by the treating physician. For the treatment of a neurodegenerative disorder, in some embodiments an aminoadamantyl nitrate is administered for a period of at least about 3 months, 6 months, 1 year, 1.5 years, 2 years, 3 years, 4 years, 5 years or longer. For the treatment of a CNS disorder that may or may not involve neurodegeneration in its pathophysiology, in certain embodiments an aminoadamantyl nitrate is administered for a period of at least about 1 week, 2 weeks, 1 month, 2 months, 3 months, 6 months, 1 year, 1.5 years, 2 years, 3 years or longer.

An aminoadamantyl nitrate can also be administered pro re nata (as needed) for the treatment of a CNS disorder, which can be determined by the treating physician. For example, for the treatment of pain or headache an aminoadamantyl nitrate can be taken until the pain or headache dissipates. If pain or headache returns, administration of the aminoadamantyl nitrate can be resumed. The appropriate dosage of, the frequency of dosing of and the length of treatment with an aminoadamantyl nitrate for a neurodegenerative or other CNS disorder can be determined by the treating physician.

A aminoadamantyl nitrate can be administered via any suitable route, and can be administered locally or systemically, for the treatment of a neurodegenerative or other CNS disorder, which can be determined by the treating physician. Potential routes of administration of an aminoadamantyl nitrate include without limitation oral, parenteral (including intradermal, subcutaneous, intramuscular, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal [e.g., by suppository], and vaginal [e.g., by suppository]). In certain embodiments, an aminoadamantyl nitrate is administered orally (e.g., as a tablet or capsule). In other embodiments, an aminoadamantyl nitrate is administered parenterally (e.g., intravenously, intramuscularly or subcutaneously, whether by injection or infusion).

The aminoadamantyl nitrate compounds described herein can effectively cross the blood-brain barrier (BBB) for the treatment of neurodegenerative and other CNS disorders, or the blood-retinal barrier (BRB) for the treatment of eye disorders such as glaucoma, AMD and retinopathy. They are small molecules with a hydrophobic/lipophilic scaffold and hence can penetrate into the brain or the eye. Increasing the lipophilicity of group(s) on aminoadamantyl compounds increases their ability to cross the BBB or the BRB. For example, 7 days of infusion of memantine or amantadine (20 and 100 mg/kg/day, respectively) resulted in a whole brain concentration of memantine or amantadine that was 44-fold and 16-fold higher than free concentration in serum, respectively [M. Hesselink et al., *Pharm. Res.,* 16:637-642 (1999)].

An aminoadamantyl nitrate can optionally be used in combination with one or more additional therapeutic agents to treat a neurodegenerative or other CNS disorder.

VII. Pharmaceutical Compositions

Additional embodiments of the disclosure relate to pharmaceutical compositions comprising an aminoadamantyl nitrate compound described herein, or a pharmaceutically acceptable salt, solvate, hydrate, clathrate or polymorph thereof, and one or more pharmaceutically acceptable excipients or carriers. The compositions can optionally contain an additional therapeutic agent. A pharmaceutical composition contains a therapeutically effective amount of an aminoadamantyl nitrate, one or more pharmaceutically acceptable excipients or carriers and optionally a therapeutically effective amount of an additional therapeutic agent, and is formulated for administration to a subject for therapeutic use.

A pharmaceutical composition contains an aminoadamantyl nitrate and optionally an additional therapeutic agent in substantially pure form. In some embodiments, the purity of the aminoadamantyl nitrate and the optional additional therapeutic agent independently is at least about 95%, 96%, 97%, 98% or 99%. In certain embodiments, the purity of the aminoadamantyl nitrate and the optional additional therapeutic agent independently is at least about 98% or 99%. In addition, a pharmaceutical composition is substantially free of contaminants or impurities. In some embodiments, the level of contaminants or impurities other than residual solvent in a pharmaceutical composition is no more than about 5%, 4%, 3%, 2% or 10% relative to the combined weight of the intended active and inactive ingredients. In certain embodiments, the level of contaminants or impurities other than residual solvent in a pharmaceutical composition is no more than about 2% or 1% relative to the combined weight of the intended active and inactive ingredients. Pharmaceutical compositions generally are prepared according to current good manufacturing practice (GMP), as recommended or required by, e.g., the Federal Food, Drug, and Cosmetic Act § 501(a)(2)(B) and the International Conference on Harmonisation Q7 Guideline.

Pharmaceutical compositions/formulations can be prepared in sterile form. For example, pharmaceutical compositions/formulations for parenteral administration by injection or infusion generally are sterile. Sterile pharmaceutical compositions/formulations are compounded or manufactured according to pharmaceutical-grade sterilization standards known to those of skill in the art, such as those disclosed in or required by the United States Pharmacopeia Chapters 797, 1072 and 1211, and 21 Code of Federal Regulations 211.

Pharmaceutically acceptable excipients and carriers include pharmaceutically acceptable substances, materials and vehicles. Non-limiting examples of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, stabilizers, preservatives, antioxidants, antimicrobial agents, antibacterial agents, antifungal agents, adjuvants, sweetening agents, flavoring agents, coloring agents, encapsulating materials and coating materials. The use of such excipients in pharmaceutical formulations is known in the art. For example, conventional vehicles and carriers include without limitation oils (e.g., vegetable oils, such as sesame oil), aqueous solvents (e.g., saline, phosphate-buffered saline [PBS] and isotonic solutions [e.g., Ringer's solution]), and solvents (e.g., dimethyl sulfoxide [DMSO] and alcohols [e.g., ethanol, glycerol and propylene glycol]). Except insofar as any conventional excipient or carrier is incompatible with the active ingredient, the disclosure encompasses the use of conventional excipients and carriers in formulations containing aminoadamantyl nitrate compounds. See, e.g., Remington: The Science and Practice of Pharmacy, 21st Ed., Lippincott Williams & Wilkins (Philadelphia, Pennsylvania [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Pre-formulation and Formulation, Gibson, Ed., CRC Press LLC (Boca Raton, Florida [2004]).

Proper formulation can depend on various factors, such as the route of administration chosen. Potential routes of administration of pharmaceutical compositions comprising aminoadamantyl nitrate compounds include without limitation oral, parenteral (including intradermal, subcutaneous, intramuscular, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal [e.g., by suppository], and vaginal [e.g., by suppository]). Topical formulations can be designed to produce a local or systemic therapeutic effect.

As an example, formulations of aminoadamantyl nitrate compounds suitable for oral administration can be presented as, e.g., boluses; capsules (including push-fit capsules and soft capsules), tablets, pills, cachets or lozenges; as powders or granules; as semisolids, electuaries, pastes or gels; as solutions or suspensions in an aqueous liquid or/and a non-aqueous liquid; or as oil-in-water liquid emulsions or water-in-oil liquid emulsions.

Push-fit capsules or two-piece hard gelatin capsules can contain an aminoadamantyl nitrate in admixture with, e.g., a filler or inert solid diluent (e.g., calcium carbonate, calcium phosphate, kaolin or lactose), a binder (e.g., a starch), a glidant or lubricant (e.g., talc or magnesium stearate), and a disintegrant (e.g., crospovidone), and optionally a stabilizer or/and a preservative. For soft capsules or single-piece gelatin capsules, an aminoadamantyl nitrate can be dissolved or suspended in a suitable liquid (e.g., liquid polyethylene glycol or an oil medium, such as a fatty oil, peanut oil, olive oil or liquid paraffin), and the liquid-filled capsules can contain one or more other liquid excipients or/and semi-solid excipients, such as a stabilizer or/and an amphiphilic agent (e.g., a fatty acid ester of glycerol, propylene glycol or sorbitol). In certain embodiments, a capsule (e.g., a hard gelatin capsule) comprises an aminoadamantyl nitrate and sugar spheres, polyvinylpyrrolidone, hypromellose, talc, polyethylene glycol, ethylcellulose, ammonium hydroxide, oleic acid, and medium-chain triglycerides.

Tablets can contain an aminoadamantyl nitrate in admixture with, e.g., a filler or inert diluent (e.g., calcium carbonate, calcium phosphate, lactose, mannitol or microcrystalline cellulose), a binding agent (e.g., a starch, gelatin, acacia, alginic acid or a salt thereof, or microcrystalline cellulose), a lubricating agent (e.g., stearic acid, magnesium stearate, talc or silicon dioxide), and a disintegrating agent (e.g., crospovidone, croscarmellose sodium or colloidal silica), and optionally a surfactant (e.g., sodium lauryl sulfate). The tablets can be uncoated or can be coated with, e.g., an enteric coating that protects the active ingredient from the acidic environment of the stomach, or with a material that delays disintegration and absorption of the active ingredient in the gastrointestinal tract and thereby provides a sustained action over a longer time period. In certain embodiments, a tablet comprises an aminoadamantyl nitrate and lactose monohydrate, microcrystalline cellulose, silica colloidal anhydrous, talc and magnesium stearate, and is film-coated (e.g., a film-coating containing hypromellose, titanium dioxide and macrogol 400).

Compositions for oral administration can also be formulated as solutions or suspensions in an aqueous liquid or/and a non-aqueous liquid, or as oil-in-water liquid emulsions or water-in-oil liquid emulsions. Dispersible powder or granules of an aminoadamantyl nitrate can be mixed with any suitable combination of an aqueous liquid, an organic solvent or/and an oil and any suitable excipients (e.g., any combination of a dispersing agent, a wetting agent, a suspending agent, an emulsifying agent or/and a preservative) to form a solution, suspension or emulsion.

Aminoadamantyl nitrate compounds can also be formulated for parenteral administration by injection or infusion to circumvent gastrointestinal absorption and first-pass metabolism. An exemplary parenteral route is intravenous. Additional advantages of intravenous administration include direct administration of a therapeutic agent into systemic circulation to achieve a rapid systemic effect, and the ability to administer the agent continuously or/and in a large volume if desired. Formulations for injection or infusion can be in the form of, e.g., solutions, suspensions or emulsions in oily or aqueous vehicles, and can contain excipients such as suspending agents, dispersing agents or/and stabilizing agents. For example, aqueous or non-aqueous (e.g., oily) sterile injection solutions can contain an aminoadamantyl nitrate along with excipients such as an antioxidant, a buffer, a bacteriostat and solutes that render the formulation isotonic with the blood of the subject. Aqueous or non-aqueous sterile suspensions can contain an aminoadamantyl nitrate along with excipients such as a suspending agent and a thickening agent, and optionally a stabilizer and an agent that increases the solubility of the aminoadamantyl nitrate to allow for the preparation of a more concentrated solution or suspension. As another example, a sterile aqueous solution for injection or infusion (e.g., subcutaneously or intravenously) can contain an aminoadamantyl nitrate, sodium chloride, a buffering agent (e.g., sodium citrate), a preservative (e.g., meta-cresol), and optionally a base (e.g., NaOH) or/and an acid (e.g., HCl) to adjust pH.

For topical administration, an aminoadamantyl nitrate can be formulated as, e.g., a buccal or sublingual tablet or pill. Advantages of a buccal or sublingual tablet or pill include avoidance of gastrointestinal absorption and first-pass metabolism, and rapid absorption into systemic circulation. A buccal or sublingual tablet or pill can be designed to provide faster release of the aminoadamantyl nitrate for more rapid uptake of it into systemic circulation. In addition to a therapeutically effective amount of an aminoadamantyl nitrate, the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide).

For topical administration, aminoadamantyl nitrate compounds can also be formulated for intranasal administration. The nasal mucosa provides a big surface area, a porous endothelium, a highly vascular subepithelial layer and a high absorption rate, and hence allows for high bioavailability. Moreover, intranasal administration avoids first-pass metabolism and can introduce a significant concentration of the aminoadamantyl nitrate to the CNS. An intranasal formulation can comprise an aminoadamantyl nitrate along with excipients, such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethylcellulose) or/and a penetration enhancer.

An additional mode of topical administration of an aminoadamantyl nitrate is pulmonary, including by oral inhalation and nasal inhalation. The lungs serve as a portal to the systemic circulation. Advantages of pulmonary drug delivery include, for example: 1) avoidance of first pass hepatic metabolism; 2) fast drug action; 3) large surface area of the alveolar region for absorption, high permeability of the lungs (thin air-blood barrier), and profuse vasculature of the airways; 4) reduced extracellular enzyme levels compared to the gastronintestinal tract due to the large alveolar surface area; and 5) smaller doses to achieve equivalent therapeutic effect compared to other oral routes, and hence reduced systemic side effects. An advantage of oral inhalation over nasal inhalation includes deeper penetration/deposition of the drug into the lungs. Oral or nasal inhalation can be achieved by means of, e.g., a metered-dose inhaler, a dry powder inhaler or a nebulizer, as is known in the art. In certain embodiments, a sterile aqueous solution for oral inhalation contains an aminoadamantyl nitrate, sodium chloride, a buffering agent (e.g., sodium citrate), optionally a preservative (e.g., meta-cresol), and optionally a base (e.g., NaOH) or/and an acid (e.g., HCl) to adjust pH.

Topical formulations for application to the skin or mucosa can be useful for transdermal or transmucosal administration of a therapeutic agent into the blood for systemic distribution. Advantages of topical administration can include circumvention of gastrointestinal absorption and first-pass metabolism, delivery of a therapeutic agent with a short half-life and low oral bioavailability, more controlled and sustained release of the therapeutic agent, a more uniform plasma dosing or delivery profile of the therapeutic agent, less frequent dosing of the therapeutic agent, minimal or no invasiveness, ease of self-administration, and increased patient compliance.

In general, compositions suitable for topical administration include without limitation liquid or semi-liquid preparations such as sprays, gels, liniments, lotions, oil-in-water or water-in-oil emulsions such as creams, foams, ointments and pastes, and solutions or suspensions such as drops (e.g., eye drops, nose drops and ear drops). In some embodiments, a topical composition comprises an aminoadamantyl nitrate dissolved, dispersed or suspended in a carrier. The carrier can be in the form of, e.g., a solution, a suspension, an emulsion, an ointment or a gel base, and can contain, e.g., petrolatum, lanolin, a wax (e.g., bee wax), mineral oil, a long-chain alcohol, polyethylene glycol or polypropylene glycol, a diluent (e.g., water or/and an alcohol [e.g., ethanol or propylene glycol]), a gel, an emulsifier, a thickening agent, a stabilizer or a preservative, or any combination thereof. A topical composition can include, or a topical formulation can be administered by means of, e.g., a transdermal or transmucosal delivery device, such as a transdermal patch, a microneedle patch or an iontophoresis device. A topical composition can deliver an aminoadamantyl nitrate transdermally or transmucosally via a concentration gradient (with or without the use of a chemical permeation enhancer) or an active mechanism (e.g., iontophoresis or microneedles).

For transdermal administration, in some embodiments a topical composition (e.g., a transdermal delivery system) comprises a chemical permeation enhancer (e.g., a surfactant [e.g., sodium laureth sulfate], optionally in combination with an aromatic compound [e.g., phenylpiperazine]) that facilitates the transport of an aminoadamantyl nitrate across the skin into systemic circulation. In further embodiments, an aminoadamantyl nitrate is administered via a transdermal patch. In certain embodiments, a transdermal patch comprises an impermeable backing membrane or layer, a drug reservoir, a semi-permeable membrane that can serve as a rate-limiting or rate-controlling diffusion barrier, and a skin-contacting adhesive layer. The semi-permeable membrane can be composed of, e.g., a suitable polymeric material (e.g., cellulose nitrate or acetate, polyisobutene, polypropylene, polyvinyl acetate or a polycarbonate). Transdermal drug-delivery systems, including patches, can be designed to provide controlled and prolonged release of a drug over a period of about 1 week, 2 weeks, 1 month or longer.

In some embodiments, an aminoadamantyl nitrate is delivered from a sustained-release composition. As used herein, the term "sustained-release composition" encompasses sustained-release, prolonged-release, extended-release, slow-release and controlled-release compositions, systems and devices. Use of a sustained-release composition can have benefits, such as an improved profile of the amount of the drug delivered to the target site(s) over a time period, including delivery of a therapeutically effective amount of the drug over a prolonged time period. In certain embodiments, the sustained-release composition delivers the aminoadamantyl nitrate over a period of at least about 1 day, 2 days, 3 days, 1 week, 2 weeks, 3 weeks, 1 month, 2 months, 3 months or longer. In some embodiments, the sustained-release composition is a drug-encapsulation system, such as, e.g., nanoparticles, microparticles or a capsule made of, e.g., a biodegradable polymer or/and a hydrogel. In certain embodiments, the sustained-release composition comprises a hydrogel. Non-limiting examples of polymers of which a hydrogel can be composed include polyvinyl alcohol, acrylate polymers (e.g., sodium polyacrylate), and other homopolymers and copolymers having a large number of hydrophilic groups (e.g., hydroxyl or/and carboxylate groups). In other embodiments, the sustained-release drug-encapsulation system comprises a membrane-enclosed reservoir, wherein the reservoir contains a drug and the membrane is permeable to the drug. Such a drug-delivery system can be in the form of, e.g., a transdermal patch.

In some embodiments, the sustained-release composition is an oral dosage form, such as a tablet or capsule. For example, a drug can be embedded in an insoluble porous matrix such that the dissolving drug must make its way out of the matrix before it can be absorbed through the gastrointestinal tract. Alternatively, a drug can be embedded in a matrix that swells to form a gel through which the drug exits. Sustained release can also be achieved by way of a single-layer or mylti-layer osmotic controlled-release oral delivery system (OROS). An OROS is a tablet with a semi-permeable outer membrane and one or more small laser-drilled holes in it. As the tablet passes through the body, water is absorbed through the semi-permeable membrane via osmosis, and the resulting osmotic pressure pushes the drug out through the hole(s) in the tablet and into the gastrointestinal tract where it can be absorbed.

In further embodiments, the sustained-release composition is formulated as polymeric nanoparticles or microparticles, wherein the polymeric particles can be delivered, e.g., by injection or from an implant. In some embodiments, the polymeric implant or polymeric nanoparticles or microparticles are composed of a biodegradable polymer. In certain embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. The biodegradable polymer of the polymeric implant or polymeric nanoparticles or microparticles can be selected so that the polymer substantially completely degrades around the time the period of treatment is expected to end, and so that the byproducts of the polymer's degradation, like the polymer, are biocompatible.

For a delayed or sustained release of an aminoadamantyl nitrate, a composition can also be formulated as, e.g., a depot that can be implanted in or injected into a subject, e.g., intramuscularly or subcutaneously. A depot formulation can be designed to deliver the aminoadamantyl nitrate over an extended period of time, e.g., over a period of at least about 1 week, 2 weeks, 3 weeks, 1 month, 6 weeks, 2 months, 3 months or longer. For example, an aminoadamantyl nitrate can be formulated with a polymeric material (e.g., polyethylene glycol [PEG], polylactic acid [PLA] or polyglycolic acid [PGA], or a copolymer thereof [e.g., PLGA]), a hydrophobic material (e.g., as an emulsion in an oil) or/and an ion-exchange resin, or as a sparingly soluble derivative (e.g., a sparingly soluble salt). As an illustrative example, an aminoadamantyl nitrate can be incorporated or embedded in sustained-release microparticles composed of PLGA and formulated as a monthly depot.

An aminoadamantyl nitrate compound can also be contained or dispersed in a matrix material. The matrix material can comprise a polymer (e.g., ethylene-vinyl acetate) and controls the release of the compound by controlling dissolution or/and diffusion of the compound from, e.g., a reservoir, and can enhance the stability of the compound while contained in the reservoir. Such a "release system" can be designed as a sustained-release system, can be configured as, e.g., a transdermal or transmucosal patch, and can contain an excipient that can accelerate the compound's release, such as a water-swellable material (e.g., a hydrogel) that aids in expelling the compound out of the reservoir. U.S. Pat. Nos. 4,144,317 and 5,797,898 describe examples of such a release system.

The release system can provide a temporally modulated release profile (e.g., pulsatile release) when time variation in plasma levels is desired, or a more continuous or consistent release profile when a constant plasma level is desired. Pulsatile release can be achieved from an individual reservoir or from a plurality of reservoirs. For example, where each reservoir provides a single pulse, multiple pulses ("pulsatile" release) are achieved by temporally staggering the single pulse release from each of multiple reservoirs.

Alternatively, multiple pulses can be achieved from a single reservoir by incorporating several layers of a release system and other materials into a single reservoir. Continuous release can be achieved by incorporating a release system that degrades, dissolves, or allows diffusion of a compound through it over an extended time period. In addition, continuous release can be approximated by releasing several pulses of a compound in rapid succession ("digital" release). An active release system can be used alone or in conjunction with a passive release system, as described in U.S. Pat. No. 5,797,898.

In addition, pharmaceutical compositions comprising an aminoadamantyl nitrate can be formulated as, e.g., liposomes, micelles (e.g., those composed of biodegradable natural or/and synthetic polymers, such as lactosomes), microparticles, microspheres or nanoparticles, whether or not designed for sustained release.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

The compositions can be presented in unit dosage form as a single dose wherein all active and inactive ingredients are combined in a suitable system, and components do not need to be mixed to form the composition to be administered. The unit dosage form contains an effective dose of an aminoadamantyl nitrate. A representative example of a unit dosage form is a tablet, capsule, or pill for oral uptake.

Alternatively, the compositions can be presented as a kit, wherein the active ingredient, excipients and carriers (e.g., solvents) are provided in two or more separate containers (e.g., ampules, vials, tubes, bottles or syringes) and need to be combined to form the composition to be administered. The kit can contain instructions for storing, preparing and administering the composition (e.g., a solution to be injected intravenously).

A kit can contain all active and inactive ingredients in unit dosage form or the active ingredient and inactive ingredients in two or more separate containers, and can contain instructions for using the pharmaceutical composition to treat a neurodegenerative or other CNS order. In some embodiments, a kit contains an aminoadamantyl nitrate or a pharmaceutically acceptable salt, solvate, hydrate, clathrate or polymorph thereof, and instructions for administering the compound to treat a neurodegenerative or other CNS order.

VIII. Synthesis of Aminoadamantyl Nitrate Compounds

The synthesis of representative aminoadamantyl nitrate compounds is described in the Examples and FIG. 1.

IX. Representative Embodiments

The following embodiments of the disclosure are provided by way of example only:

1. A compound of Formula I:

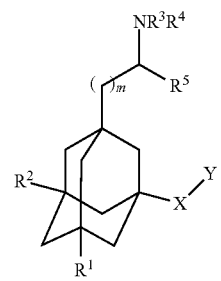

I wherein:
  $R^1$ and $R^2$ independently are hydrogen, halide, linear or branched alkyl, linear or branched heteroalkyl, linear or branched alkoxy, linear or branched —O-heteroalkyl, cycloalkyl, heterocyclyl, aryl or heteroaryl, each of which can optionally be substituted;
  $R^3$ and $R^4$ independently are hydrogen or linear or branched $C_1$-$C_6$ alkyl, or $R^3$, $R^4$ and the nitrogen atom to which they are attached form a 3-8-membered heterocyclic ring;
  $R^5$ is hydrogen or linear or branched $C_1$-$C_6$ alkyl;
  X is bond, linear or branched -alkyl-, linear or branched -heteroalkyl-, linear or branched —O-alkyl-, linear or branched —O-heteroalkyl-, —(CH$_2$)$_j$-cycloalkyl-(CH$_2$)$_k$—, —(CH$_2$)$_j$-heterocyclyl-(CH$_2$)$_k$—, —(CH$_2$)$_j$-aryl-(O)$_h$—(CH$_2$)$_k$— or —(CH$_2$)$_j$-heteroaryl-(O)$_h$—(CH$_2$)$_k$—, each of which can optionally be substituted;
  Y is —ONO$_2$ or

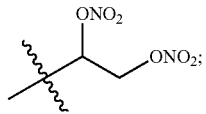

m is 0, 1, 2, 3, 4 or 5;
  j is 0, 1, 2 or 3;
  k is 0, 1, 2 or 3; and
  h is 0 or 1;

or a pharmaceutically acceptable salt, solvate, hydrate, clathrate, polymorph or stereoisomer thereof.

2. The compound of embodiment 1, which is of Formula Ia:

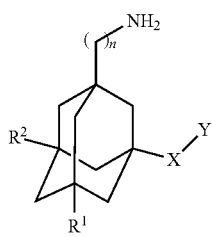

wherein:
  R¹, R², X and Y are as defined in embodiment 1; and
  n is 1, 2, 3, 4, 5 or 6;
or a pharmaceutically acceptable salt, solvate, hydrate, clathrate, polymorph or stereoisomer thereof.

3. The compound of embodiment 1, which is of Formula IA:

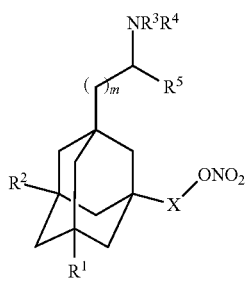

wherein R¹, R², R³, R⁴, R⁵, X and m are as defined in embodiment 1;
or a pharmaceutically acceptable salt, solvate, hydrate, clathrate, polymorph or stereoisomer thereof.

4. The compound of embodiment 3, which is of Formula IAa:

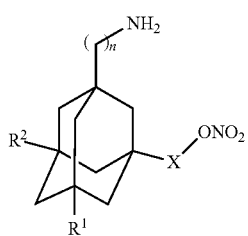

wherein:
  R¹, R² and X are as defined in embodiment 1; and
  n is 1, 2, 3, 4, 5 or 6;
or a pharmaceutically acceptable salt, solvate, hydrate, clathrate, polymorph or stereoisomer thereof.

5. The compound of embodiment 1, which is of Formula IB:

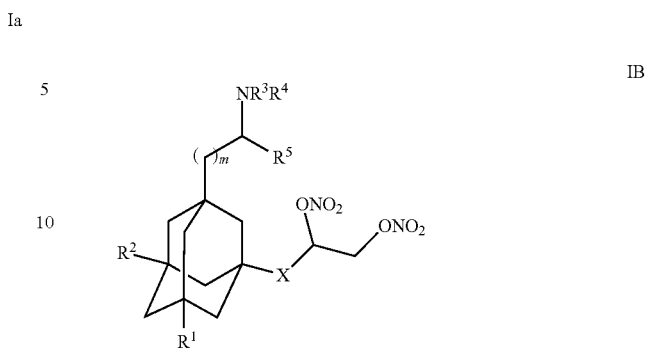

wherein R¹, R², R³, R⁴, R⁵, X and m are as defined in embodiment 1;
or a pharmaceutically acceptable salt, solvate, hydrate, clathrate, polymorph or stereoisomer thereof.

6. The compound of embodiment 5, which is of Formula IBa:

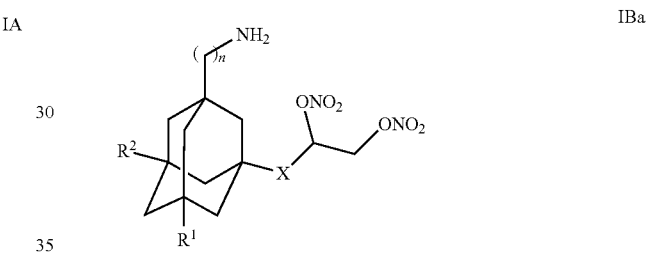

wherein:
  R¹, R² and X are as defined in embodiment 1; and
  n is 1, 2, 3, 4, 5 or 6;
or a pharmaceutically acceptable salt, solvate, hydrate, clathrate, polymorph or stereoisomer thereof.

7. The compound of any one of the preceding embodiments, wherein X of the compound of Formula I, Ia, IA, IAa, IB or IBa is bond, linear or branched $C_1$-$C_6$ or $C_1$-$C_3$-alkyl-, or linear or branched $C_1$-$C_6$ or $C_1$-$C_3$—O-alkyl-.

8. The compound of embodiment 7, wherein X of the compound of Formula I, Ia, IA, IAa, IB or IBa is bond or linear or branched $C_1$-$C_3$-alkyl- [e.g., —$CH_2$—, —$(CH_2)_2$—, —$CHCH_3$, —$(CH_2)_3$—, —$CHCH_2CH_3$, —$CH_2CHCH_3$ or —$CH(CH_3)CH_2$—].

9. A compound of Formula II or Formula III:

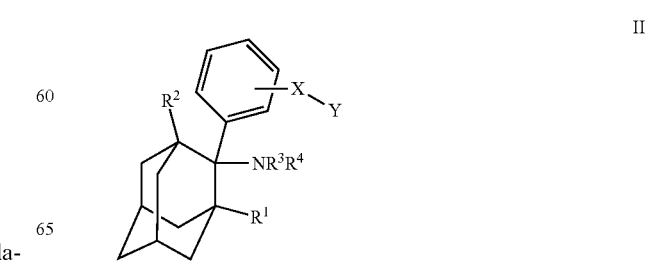

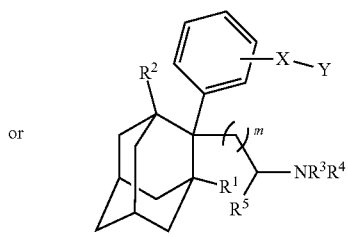

III or wherein:
- $R^1$ and $R^2$ independently are hydrogen, halide, linear or branched alkyl, linear or branched heteroalkyl, linear or branched alkoxy, linear or branched —O-heteroalkyl, cycloalkyl, heterocyclyl, aryl or heteroaryl, each of which can optionally be substituted;
- $R^3$ and $R^4$ independently are hydrogen or linear or branched $C_1$-$C_6$ alkyl, or $R^3$, $R^4$ and the nitrogen atom to which they are attached form a 3-8-membered heterocyclic ring;
- $R^5$ is hydrogen or linear or branched $C_1$-$C_6$ alkyl;
- X is bond, linear or branched -alkyl-, linear or branched -heteroalkyl-, linear or branched —O-alkyl-, linear or branched —O-heteroalkyl-, —($CH_2$)$_j$-cycloalkyl-($CH_2$)$_k$—, —($CH_2$)$_j$-heterocyclyl-($CH_2$)$_k$—, —($CH_2$)$_j$-aryl-(O)$_h$—($CH_2$)$_k$— or —($CH_2$)$_j$-heteroaryl-(O)$_h$—($CH_2$)$_k$—, each of which can optionally be substituted;
- Y is —$ONO_2$ or

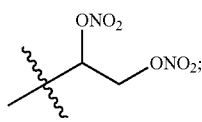

- m is 0, 1, 2, 3, 4 or 5;
- j is 0, 1, 2 or 3;
- k is 0, 1, 2 or 3; and
- h is 0 or 1;

or a pharmaceutically acceptable salt, solvate, hydrate, clathrate, polymorph or stereoisomer thereof.

10. The compound of embodiment 9, which is of Formula IV:

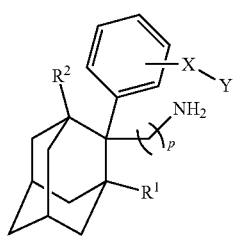

IV wherein:
- $R^1$, $R^2$, X and Y are as defined in embodiment 9; and
- p is 0, 1, 2, 3, 4, 5 or 6;

or a pharmaceutically acceptable salt, solvate, hydrate, clathrate, polymorph or stereoisomer thereof.

11. The compound of embodiment 10, which is of Formula IVa:

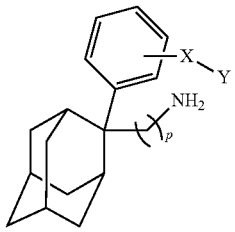

IVa wherein:
- X and Y are as defined in embodiment 9; and
- p is 0, 1, 2, 3, 4, 5 or 6;

or a pharmaceutically acceptable salt, solvate, hydrate, clathrate, polymorph or stereoisomer thereof.

12. The compound of embodiment 9, which is of Formula IIA or Formula IIIA:

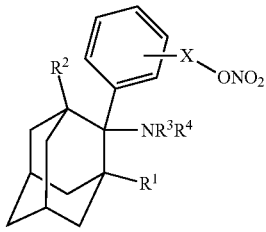

IIA

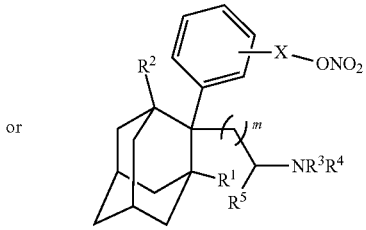

IIIA or wherein $R^1$, $R^2$, $R^3$, $R^4$, $R^5$, X and m are as defined in embodiment 9;

or a pharmaceutically acceptable salt, solvate, hydrate, clathrate, polymorph or stereoisomer thereof.

13. The compound of embodiment 12, which is of Formula IVA:

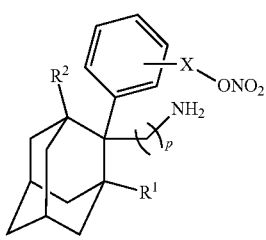

IVA wherein:
- $R^1$, $R^2$ and X are as defined in embodiment 9; and
- p is 0, 1, 2, 3, 4, 5 or 6;

or a pharmaceutically acceptable salt, solvate, hydrate, clathrate, polymorph or stereoisomer thereof.

14. The compound of embodiment 13, which is of Formula IVAa:

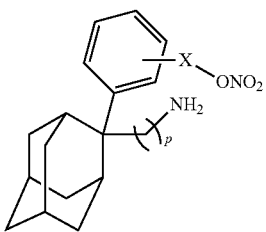

IVAa

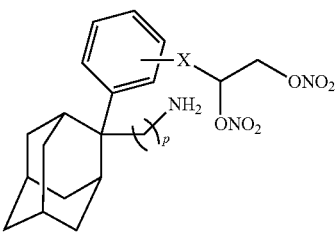

IVBa wherein:
X is as defined in embodiment 9; and
p is 0, 1, 2, 3, 4, 5 or 6;
or a pharmaceutically acceptable salt, solvate, hydrate, clathrate, polymorph or stereoisomer thereof.

15. The compound of embodiment 9, which is of Formula IIB or Formula IIIB:

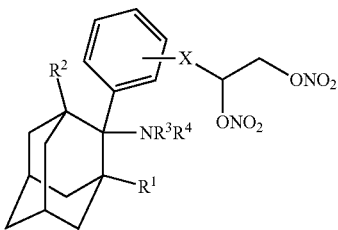

IIB or

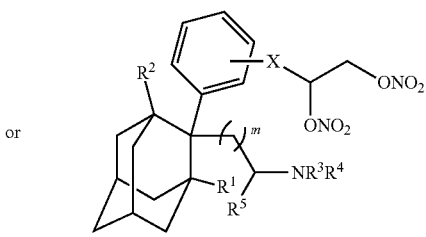

IIIB wherein $R^1$, $R^2$, $R^3$, $R^4$, $R^5$, X and m are as defined in embodiment 9;
or a pharmaceutically acceptable salt, solvate, hydrate, clathrate, polymorph or stereoisomer thereof.

16. The compound of embodiment 15, which is of Formula IVB:

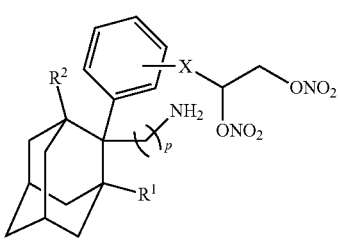

IVB wherein:
$R^1$, $R^2$ and X are as defined in embodiment 9; and
p is 0, 1, 2, 3, 4, 5 or 6;
or a pharmaceutically acceptable salt, solvate, hydrate, clathrate, polymorph or stereoisomer thereof.

17. The compound of embodiment 16, which is of Formula IVBa:

wherein:
X is as defined in embodiment 9; and
p is 0, 1, 2, 3, 4, 5 or 6;
or a pharmaceutically acceptable salt, solvate, hydrate, clathrate, polymorph or stereoisomer thereof.

18. The compound of any one of embodiments 9 to 17, wherein the —X—Y, —X—$ONO_2$ or —X—CH($ONO_2$) $CH_2$—$ONO_2$ moiety is attached to a meta position of the phenyl ring.

19. The compound of any one of embodiments 9 to 18, wherein X of the compound of Formula II, IIA, IIB, III, IIIA, IIIB, IV, IVa, IVA, IVAa, IVB or IVBa is bond, linear or branched $C_1$-$C_6$ or $C_1$-$C_3$-alkyl-, or linear or branched $C_1$-$C_6$ or $C_1$-$C_3$—O-alkyl-.

20. The compound of any one of the preceding embodiments, wherein:
m is 0, 1 or 2;
n is 1, 2 or 3; or
p is 0, 1, 2 or 3.

21. The compound of any one of the preceding embodiments, wherein both $R^3$ and $R^4$ are hydrogen.

22. The compound of any one of embodiments 1 to 20, wherein one of $R^3$ and $R^4$ is hydrogen, and the other is linear or branched $C_1$-$C_3$ alkyl (e.g., methyl or ethyl).

23. The compound of any one of embodiments 1 to 20, wherein $R^3$ and $R^4$ independently are linear $C_1$-$C_3$ alkyl (e.g., methyl or ethyl), optionally the same alkyl group.

24. The compound of any one of the preceding embodiments, wherein $R^5$ is hydrogen.

25. The compound of any one of embodiments 1 to 23, wherein $R^5$ is linear or branched $C_1$-$C_3$ alkyl (e.g., methyl or ethyl).

26. The compound of any one of the preceding embodiments, wherein $R^1$ and $R^2$ independently are hydrogen or linear or branched $C_1$-$C_6$ alkyl.

27. The compound of embodiment 26, wherein $R^1$ and $R^2$ independently are hydrogen or linear or branched $C_1$-$C_3$ alkyl (e.g., methyl, ethyl or n-propyl).

28. The compound of embodiment 26 or 27, wherein both $R^1$ and $R^2$ are hydrogen.

29. The compound of embodiment 26 or 27, wherein $R^1$ is hydrogen and $R^2$ is linear or branched $C_1$-$C_6$ or $C_1$-$C_3$ alkyl (e.g., methyl, ethyl or n-propyl), or $R^2$ is hydrogen and $R^1$ is linear or branched $C_1$-$C_6$ or $C_1$-$C_3$ alkyl (e.g., methyl, ethyl or n-propyl).

30. The compound of embodiment 26 or 27, wherein $R^1$ and $R^2$ independently are linear or branched $C_1$-$C_6$ or $C_1$-$C_3$ alkyl (e.g., methyl, ethyl or n-propyl), optionally the same alkyl group.

31. The compound of any one of the preceding embodiments, wherein the $R^1$ group, the $R^2$ group or the X group, or any combination or all thereof, independently are substituted with 1, 2 or 3 substituents selected from linear or branched $C_1$-$C_6$ or $C_1$-$C_3$ alkyl, haloalkyl, —$OR^6$, —$NR^7R^8$, —$ONO_2$, —CN, —C(=O)$R^6$, —C(=O)$OR^6$, —OC(=O)R⁶, —C(=O)NR⁷R⁸, —NR⁷C(=O)R⁶, —OC(=O)OR⁶, —OC(=O)NR⁷R⁸, —NR⁷C(=O)OR⁶, —NR⁶C(=O)NR⁷R⁸, aryl and heteroaryl, or/and are substituted with 1 to 6 halogen (e.g., fluorine) or deuterium atoms or have all available hydrogen atoms replaced with halogen (e.g., fluorine) or deuterium atoms, wherein:

R⁶ in each occurrence independently is hydrogen or linear or branched $C_1$-$C_6$ or $C_1$-$C_3$ alkyl; and R⁷ and R⁸ in each occurrence independently are hydrogen or linear or branched $C_1$-$C_6$ or $C_1$-$C_3$ alkyl, or R⁷, R⁸ and the nitrogen atom to which they are attached form a 3-6-membered ring.

32. The compound of embodiment 31, wherein the R¹ group, the R² group or the X group, or any combination or all thereof, independently are deuteroalkyl, fluoroalkyl or alkyl-ONO₂.

33. The compound of any one of the preceding embodiments, wherein X has 0, 1, 2, 3, 4, 5 or 6 carbon atoms.

34. The compound of embodiment 33, wherein X has 0, 1, 2 or 3 carbon atoms.

35. The compound of any one of the preceding embodiments, which is a hydrochloride (HCl) or hydrobromide (HBr) salt.

36. A compound of Formula IAa selected from the compounds shown in Table 1:

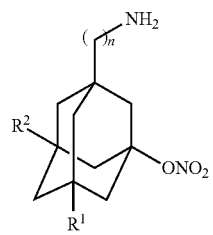

IAa-i

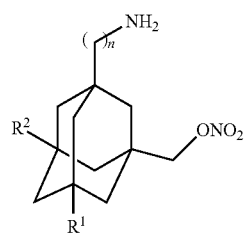

IA-a-ii

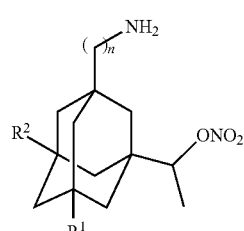

IAa-iii

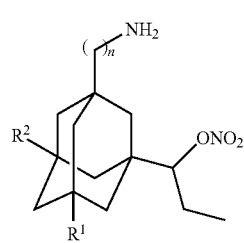

IAa-iv

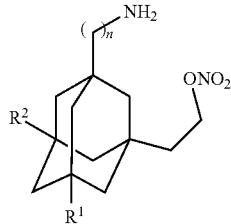

IAa-v

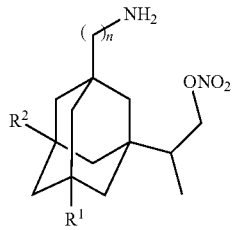

IA-a-vi

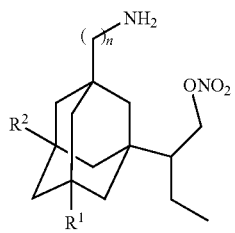

IAa-vii

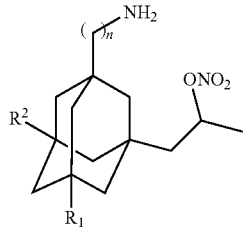

IAa-viii

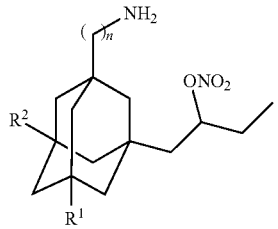

IAa-ix

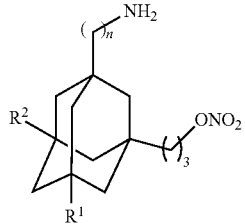

IAa-x

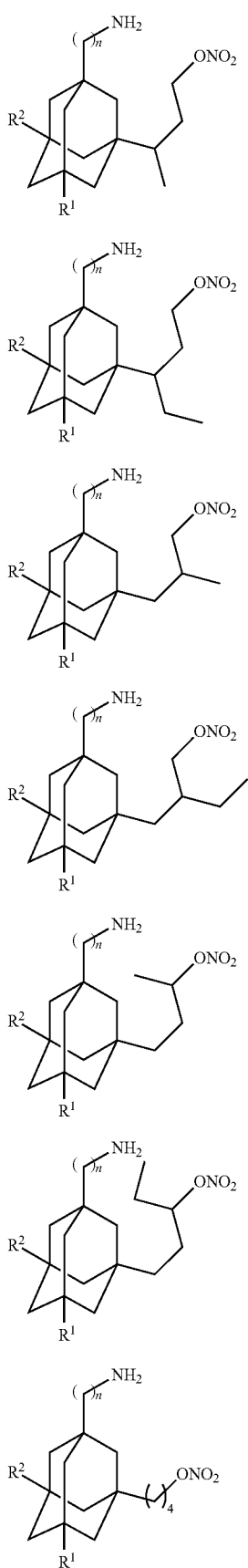

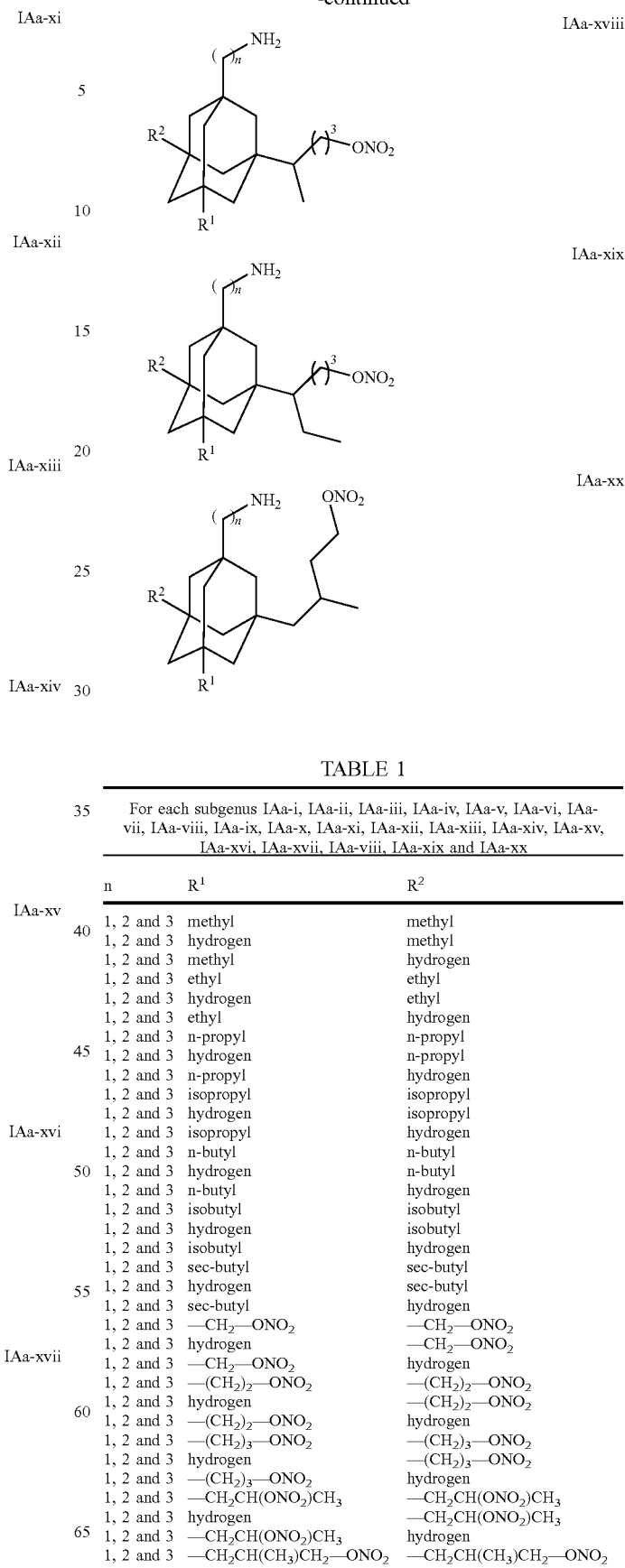

TABLE 1

For each subgenus IAa-i, IAa-ii, IAa-iii, IAa-iv, IAa-v, IAa-vi, IAa-vii, IAa-viii, IAa-ix, IAa-x, IAa-xi, IAa-xii, IAa-xiii, IAa-xiv, IAa-xv, IAa-xvi, IAa-xvii, IAa-viii, IAa-xix and IAa-xx

| n | $R^1$ | $R^2$ |
|---|---|---|
| 1, 2 and 3 | methyl | methyl |
| 1, 2 and 3 | hydrogen | methyl |
| 1, 2 and 3 | methyl | hydrogen |
| 1, 2 and 3 | ethyl | ethyl |
| 1, 2 and 3 | hydrogen | ethyl |
| 1, 2 and 3 | ethyl | hydrogen |
| 1, 2 and 3 | n-propyl | n-propyl |
| 1, 2 and 3 | hydrogen | n-propyl |
| 1, 2 and 3 | n-propyl | hydrogen |
| 1, 2 and 3 | isopropyl | isopropyl |
| 1, 2 and 3 | hydrogen | isopropyl |
| 1, 2 and 3 | isopropyl | hydrogen |
| 1, 2 and 3 | n-butyl | n-butyl |
| 1, 2 and 3 | hydrogen | n-butyl |
| 1, 2 and 3 | n-butyl | hydrogen |
| 1, 2 and 3 | isobutyl | isobutyl |
| 1, 2 and 3 | hydrogen | isobutyl |
| 1, 2 and 3 | isobutyl | hydrogen |
| 1, 2 and 3 | sec-butyl | sec-butyl |
| 1, 2 and 3 | hydrogen | sec-butyl |
| 1, 2 and 3 | sec-butyl | hydrogen |
| 1, 2 and 3 | —$CH_2$—$ONO_2$ | —$CH_2$—$ONO_2$ |
| 1, 2 and 3 | hydrogen | —$CH_2$—$ONO_2$ |
| 1, 2 and 3 | —$CH_2$—$ONO_2$ | hydrogen |
| 1, 2 and 3 | —$(CH_2)_2$—$ONO_2$ | —$(CH_2)_2$—$ONO_2$ |
| 1, 2 and 3 | hydrogen | —$(CH_2)_2$—$ONO_2$ |
| 1, 2 and 3 | —$(CH_2)_2$—$ONO_2$ | hydrogen |
| 1, 2 and 3 | —$(CH_2)_3$—$ONO_2$ | —$(CH_2)_3$—$ONO_2$ |
| 1, 2 and 3 | hydrogen | —$(CH_2)_3$—$ONO_2$ |
| 1, 2 and 3 | —$(CH_2)_3$—$ONO_2$ | hydrogen |
| 1, 2 and 3 | —$CH_2CH(ONO_2)CH_3$ | —$CH_2CH(ONO_2)CH_3$ |
| 1, 2 and 3 | hydrogen | —$CH_2CH(ONO_2)CH_3$ |
| 1, 2 and 3 | —$CH_2CH(ONO_2)CH_3$ | hydrogen |
| 1, 2 and 3 | —$CH_2CH(CH_3)CH_2$—$ONO_2$ | —$CH_2CH(CH_3)CH_2$—$ONO_2$ |

TABLE 1-continued

For each subgenus IAa-i, IAa-ii, IAa-iii, IAa-iv, IAa-v, IAa-vi, IAa-vii, IAa-viii, IAa-ix, IAa-x, IAa-xi, IAa-xii, IAa-xiii, IAa-xiv, IAa-xv, IAa-xvi, IAa-xvii, IAa-viii, IAa-xix and IAa-xx

| n | $R^1$ | $R^2$ |
|---|---|---|
| 1, 2 and 3 | hydrogen | —$CH_2CH(CH_3)CH_2$—$ONO_2$ |
| 1, 2 and 3 | —$CH_2CH(CH_3)CH_2$—$ONO_2$ | hydrogen | and pharmaceutically acceptable salts (e.g., HCl and HBr salts), solvates, hydrates, clathrates, polymorphs and stereoisomers thereof.

37. The compound of embodiment 36, which is selected from:

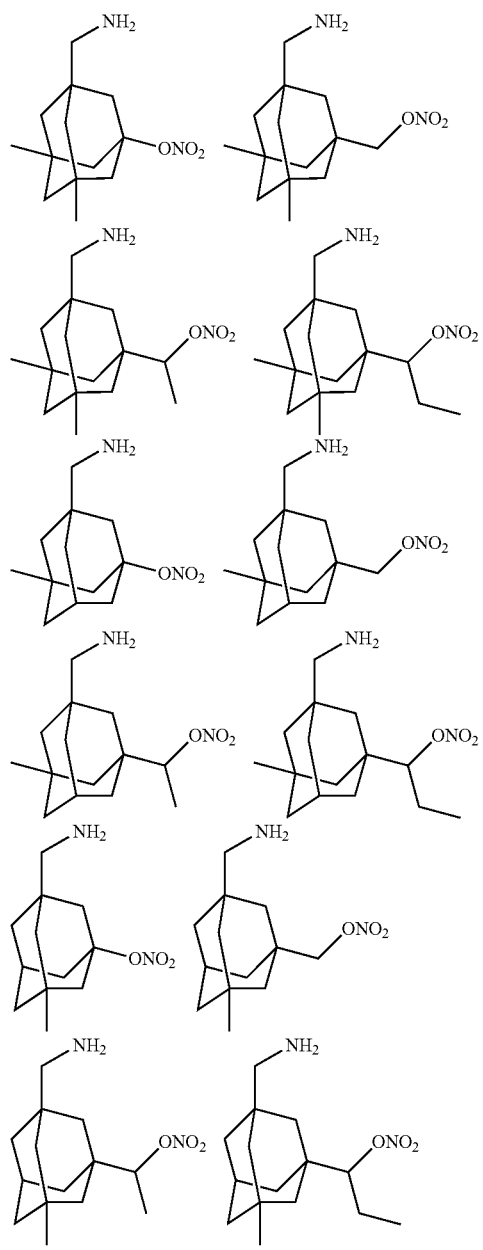
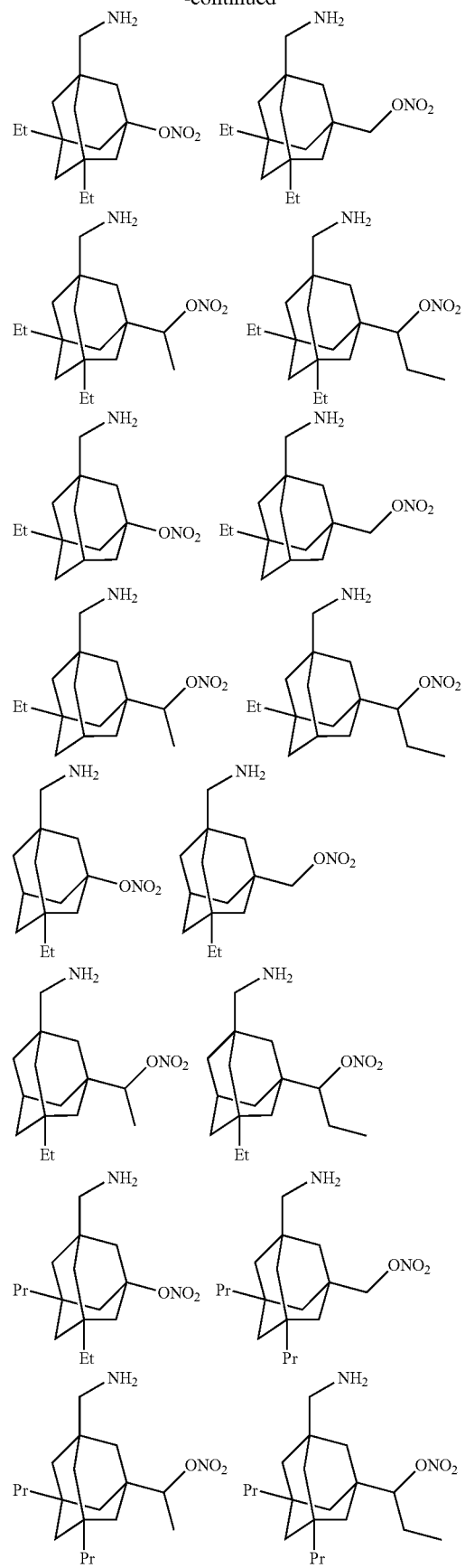

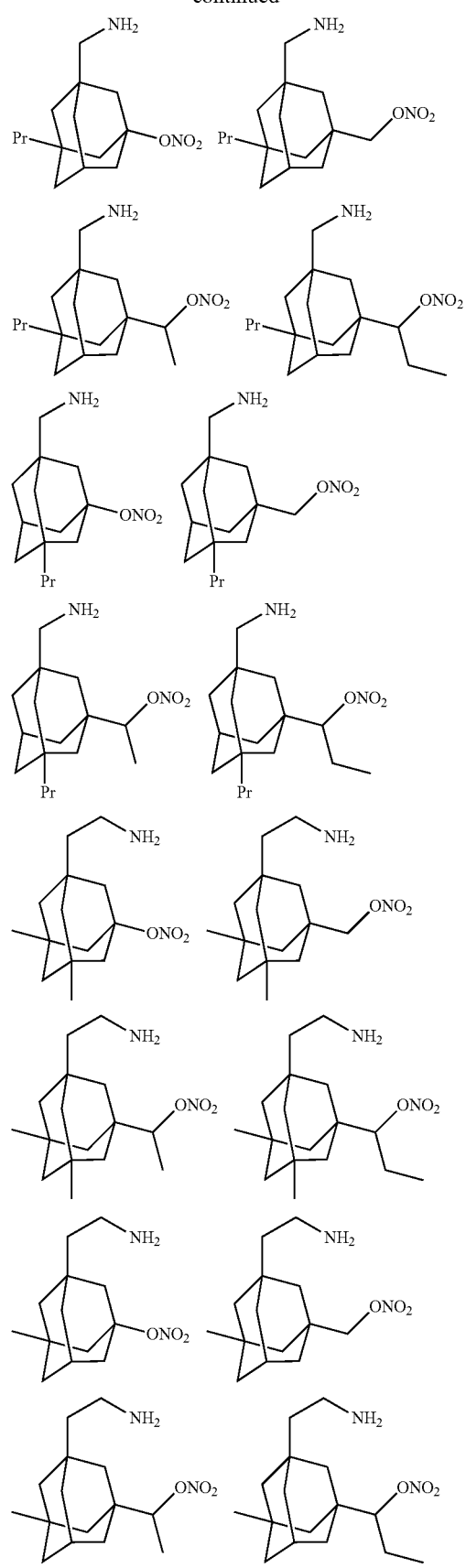
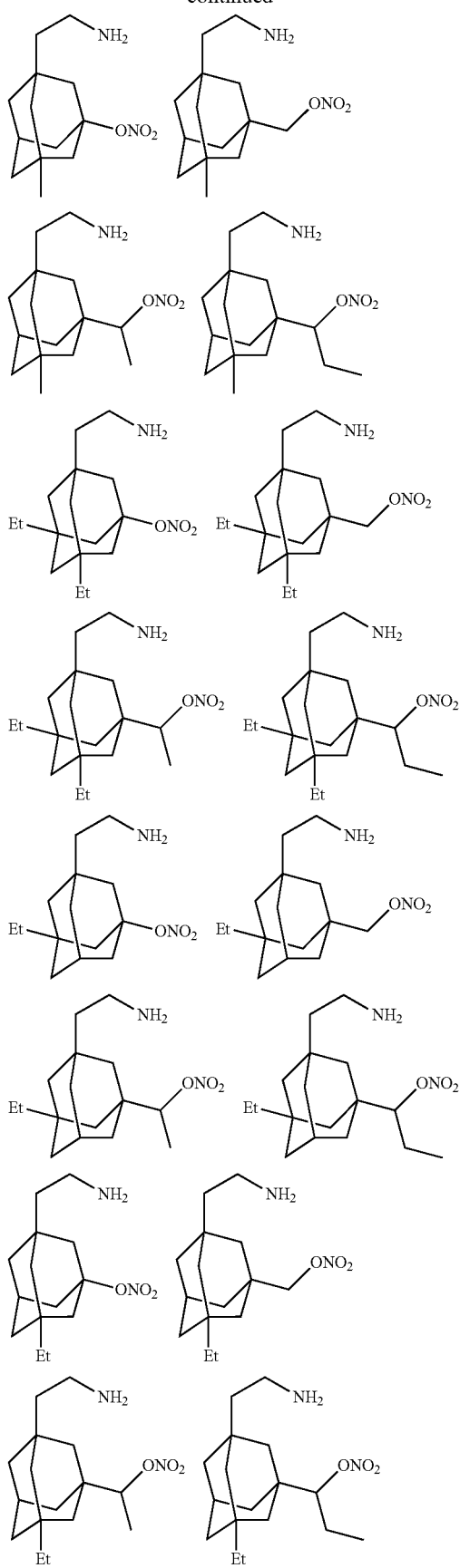

-continued
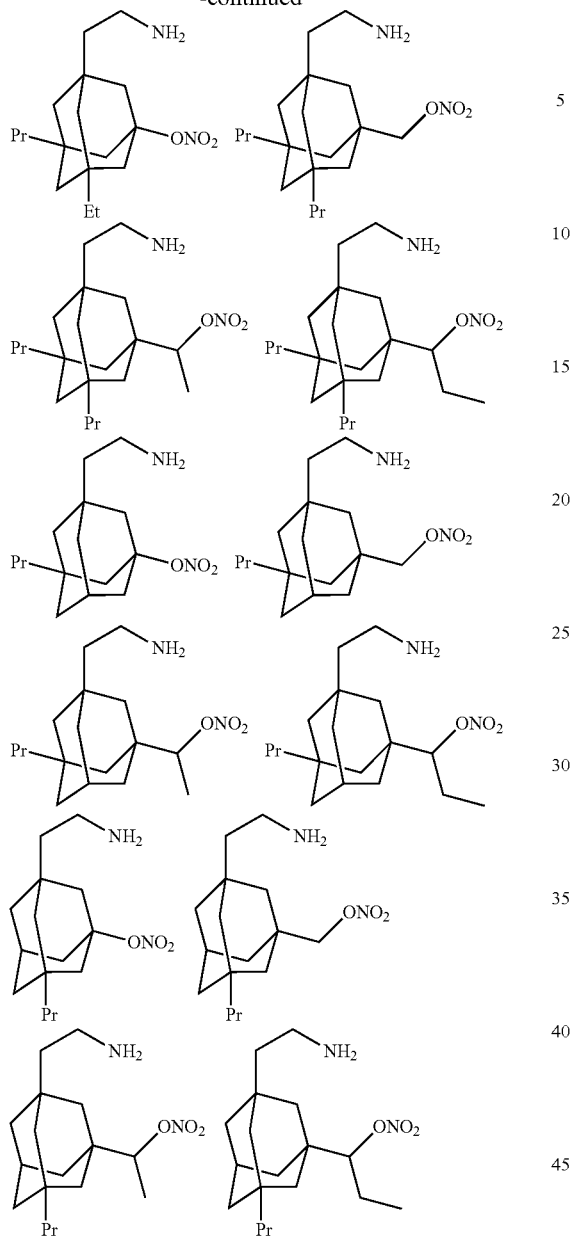
and pharmaceutically acceptable salts (e.g., HCl and HBr salts), solvates, hydrates, clathrates, polymorphs and stereoisomers thereof, wherein Et=ethyl and Pr=n-propyl.
38. A compound of Formula IBa selected from the compounds shown in Table 2:
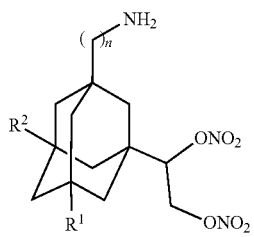
IBa-i
-continued
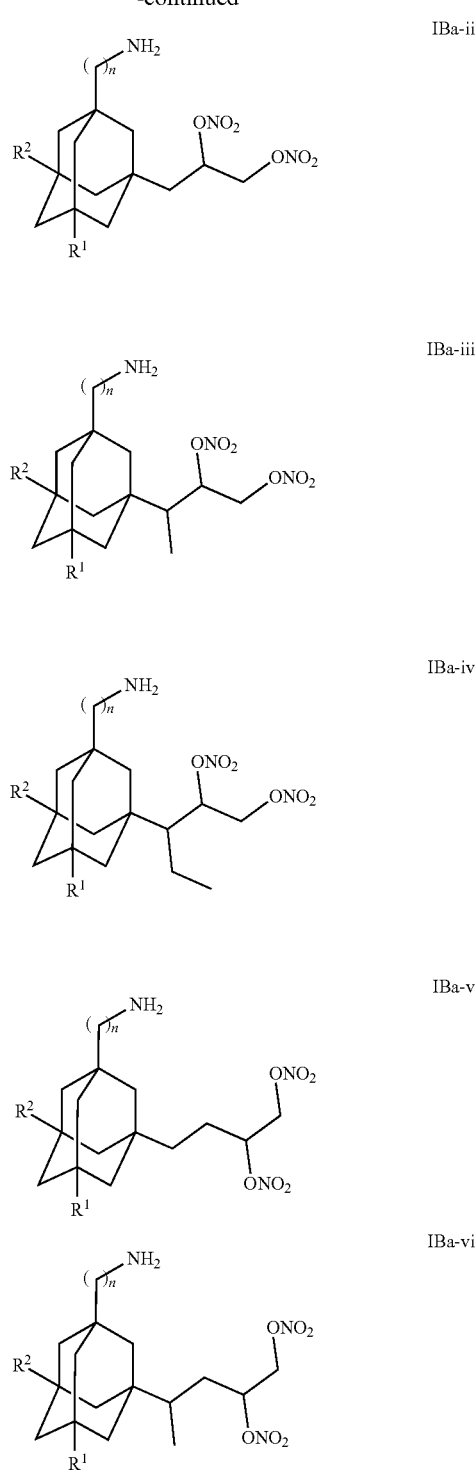
IBa-ii
IBa-iii
IBa-iv
IBa-v
IBa-vi
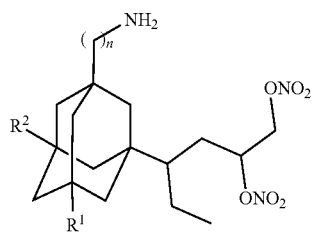
IBa-vii

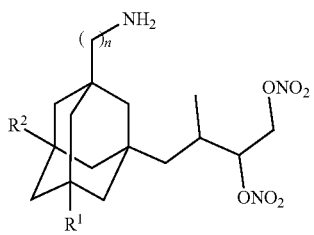

IBa-viii

TABLE 2

For each subgenus IBa-i, IBa-ii, IBa-iii, IBa-iv, IBa-v, IBa-vi, IBa-vii and IBa-viii

| n | $R^1$ | $R^2$ |
|---|---|---|
| 1, 2 and 3 | methyl | methyl |
| 1, 2 and 3 | hydrogen | methyl |
| 1, 2 and 3 | methyl | hydrogen |
| 1, 2 and 3 | ethyl | ethyl |
| 1, 2 and 3 | hydrogen | ethyl |
| 1, 2 and 3 | ethyl | hydrogen |
| 1, 2 and 3 | n-propyl | n-propyl |
| 1, 2 and 3 | hydrogen | n-propyl |
| 1, 2 and 3 | n-propyl | hydrogen |
| 1, 2 and 3 | isopropyl | isopropyl |
| 1, 2 and 3 | hydrogen | isopropyl |
| 1, 2 and 3 | isopropyl | hydrogen |
| 1, 2 and 3 | n-butyl | n-butyl |
| 1, 2 and 3 | hydrogen | n-butyl |
| 1, 2 and 3 | n-butyl | hydrogen |
| 1, 2 and 3 | isobutyl | isobutyl |
| 1, 2 and 3 | hydrogen | isobutyl |
| 1, 2 and 3 | isobutyl | hydrogen |
| 1, 2 and 3 | sec-butyl | sec-butyl |
| 1, 2 and 3 | hydrogen | sec-butyl |
| 1, 2 and 3 | sec-butyl | hydrogen |
| 1, 2 and 3 | —CH$_2$—ONO$_2$ | —CH$_2$—ONO$_2$ |
| 1, 2 and 3 | hydrogen | —CH$_2$—ONO$_2$ |
| 1, 2 and 3 | —CH$_2$—ONO$_2$ | hydrogen |
| 1, 2 and 3 | —(CH$_2$)$_2$—ONO$_2$ | —(CH$_2$)$_2$—ONO$_2$ |
| 1, 2 and 3 | hydrogen | —(CH$_2$)$_2$—ONO$_2$ |
| 1, 2 and 3 | —(CH$_2$)$_2$—ONO$_2$ | hydrogen |
| 1, 2 and 3 | —(CH$_2$)$_3$—ONO$_2$ | —(CH$_2$)$_3$—ONO$_2$ |
| 1, 2 and 3 | hydrogen | —(CH$_2$)$_3$—ONO$_2$ |
| 1, 2 and 3 | —(CH$_2$)$_3$—ONO$_2$ | hydrogen |
| 1, 2 and 3 | —CH$_2$CH(ONO$_2$)CH$_3$ | —CH$_2$CH(ONO$_2$)CH$_3$ |
| 1, 2 and 3 | hydrogen | —CH$_2$CH(ONO$_2$)CH$_3$ |
| 1, 2 and 3 | —CH$_2$CH(ONO$_2$)CH$_3$ | hydrogen |
| 1, 2 and 3 | —CH$_2$CH(CH$_3$)CH$_2$—ONO$_2$ | —CH$_2$CH(CH$_3$)CH$_2$—ONO$_2$ |
| 1, 2 and 3 | hydrogen | —CH$_2$CH(CH$_3$)CH$_2$—ONO$_2$ |
| 1, 2 and 3 | —CH$_2$CH(CH$_3$)CH$_2$—ONO$_2$ | hydrogen | and pharmaceutically acceptable salts (e.g., HCl and HBr salts), solvates, hydrates, clathrates, polymorphs and stereoisomers thereof.

39. The compound of embodiment 38, which is selected from:

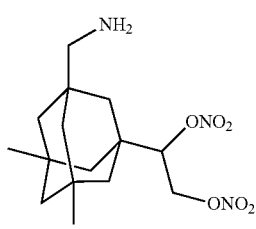
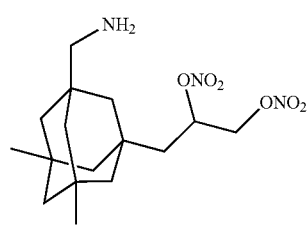
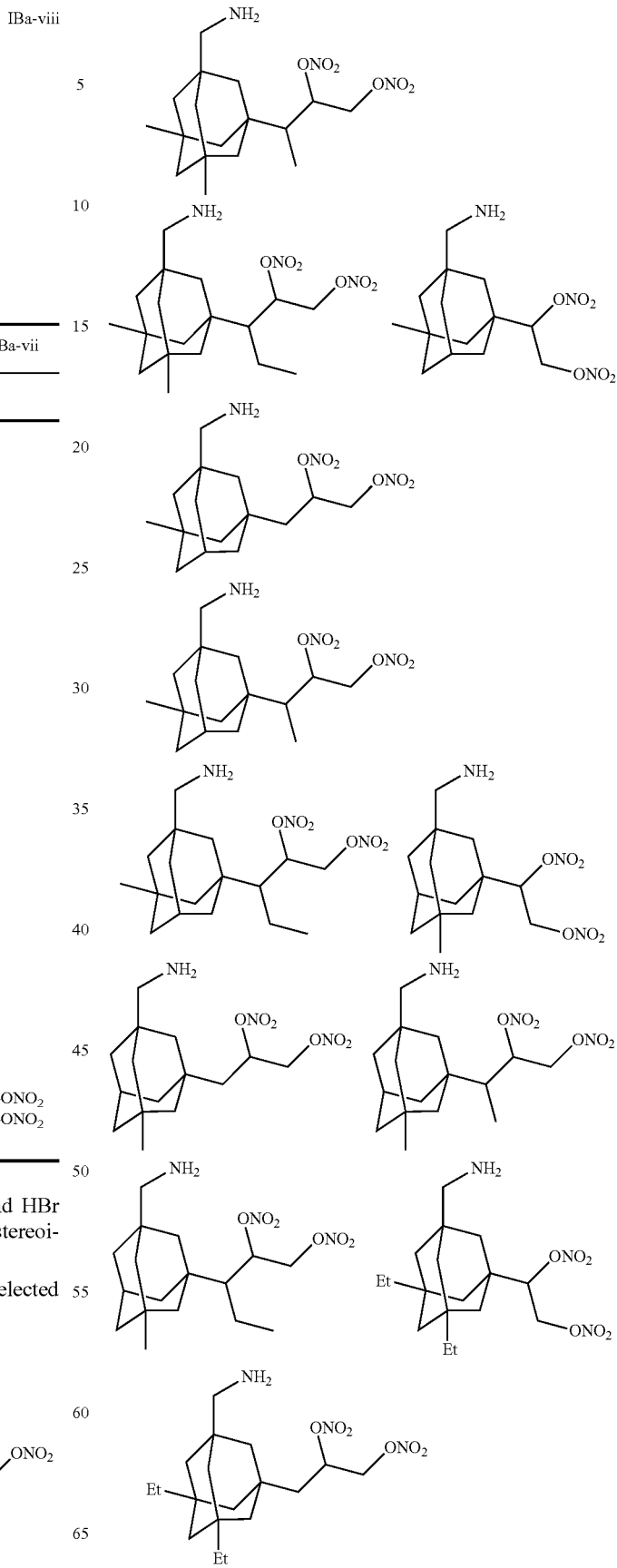

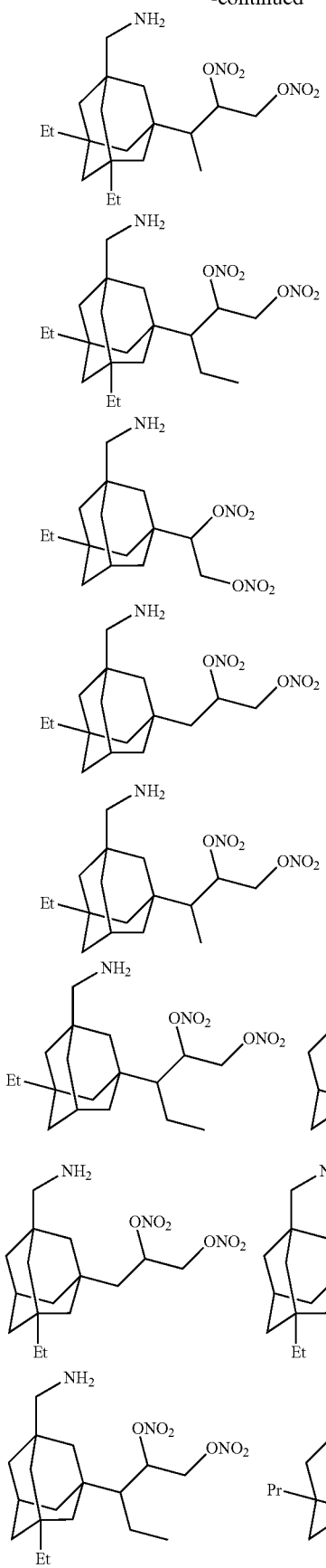
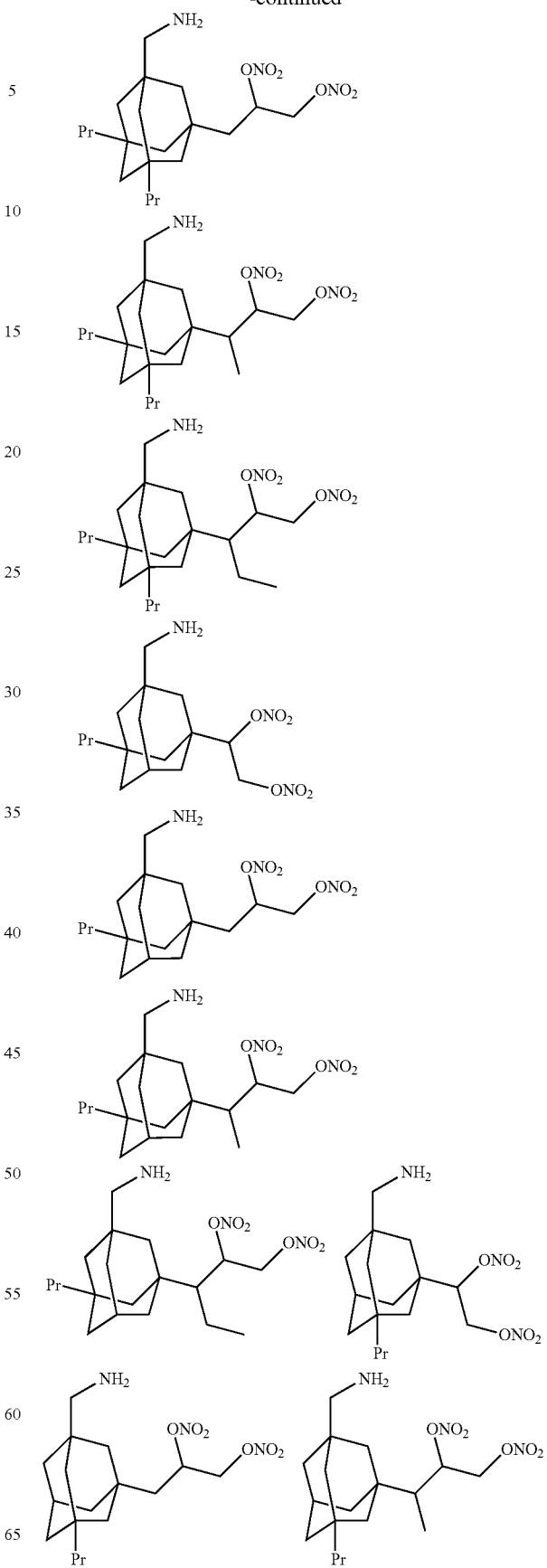

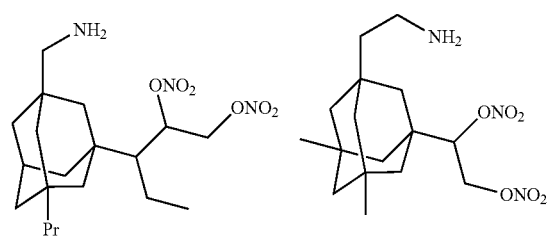
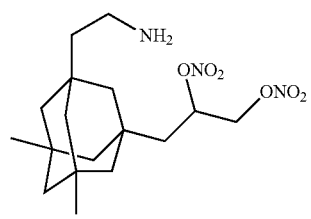
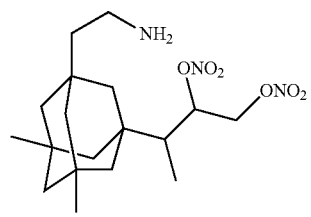
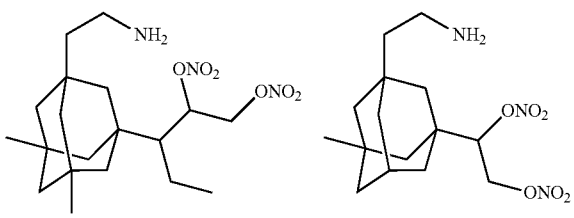
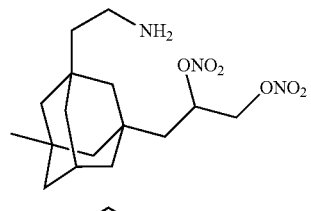
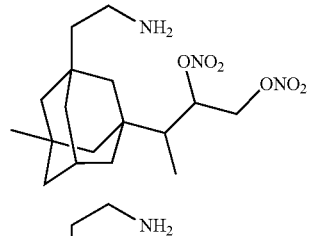
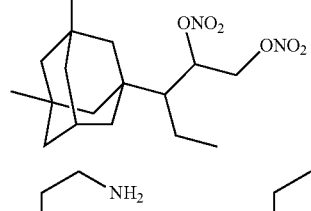
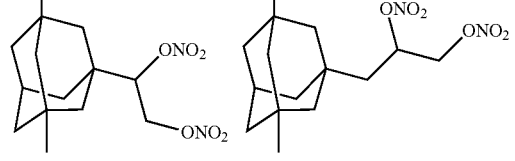
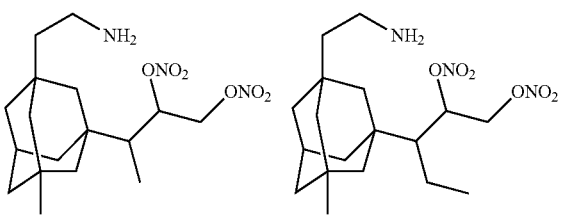
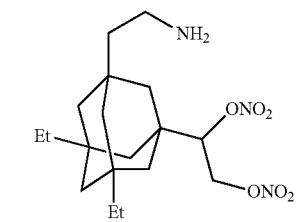
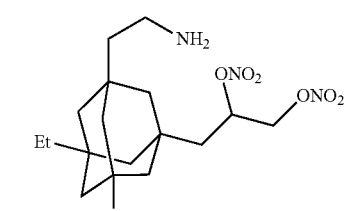
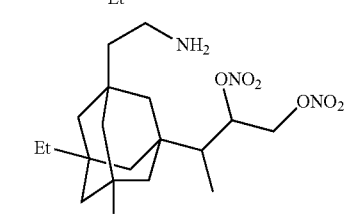
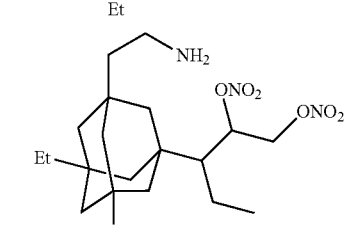
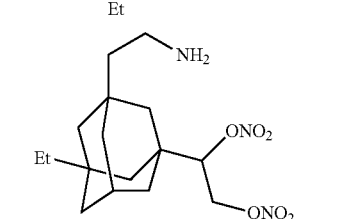
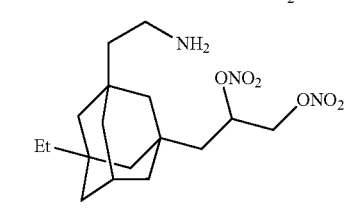
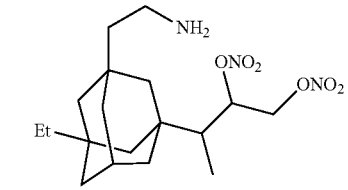

-continued
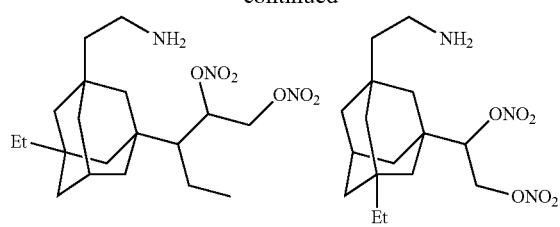
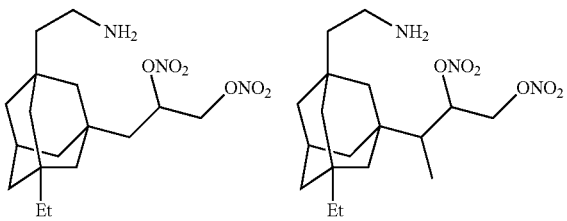
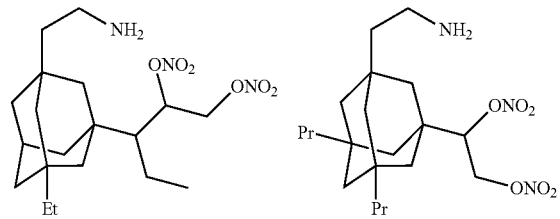
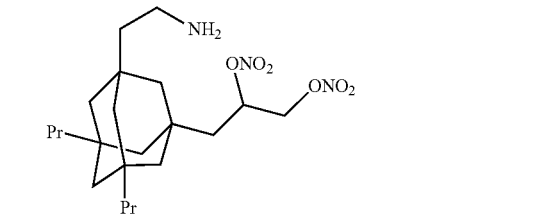
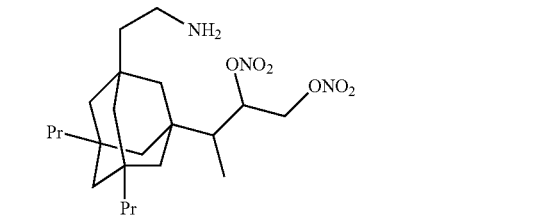
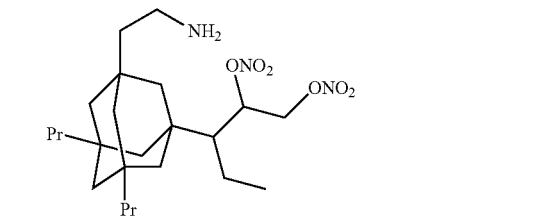
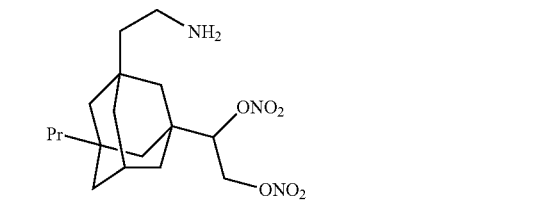
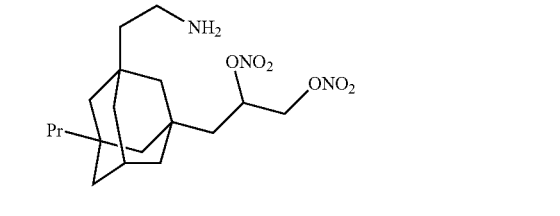
-continued
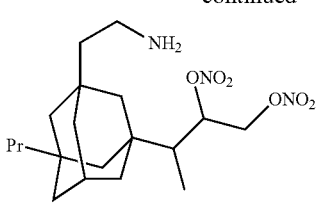
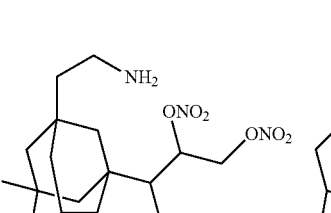
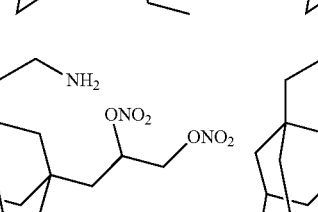
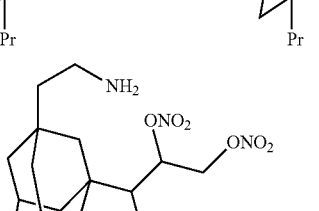
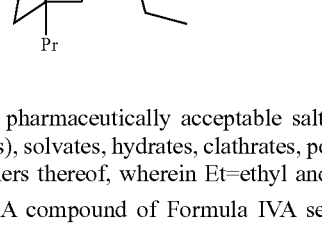
and pharmaceutically acceptable salts (e.g., HCl and HBr salts), solvates, hydrates, clathrates, polymorphs and stereoisomers thereof, wherein Et=ethyl and Pr=n-propyl.
40. A compound of Formula IVA selected from the compounds shown in Table 3:
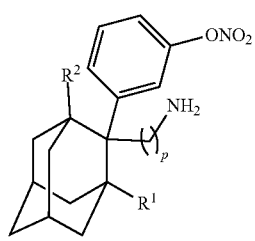
IVA-i
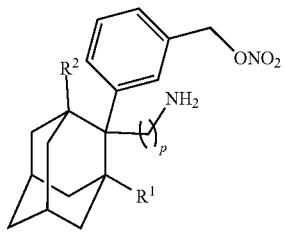
IVA-ii

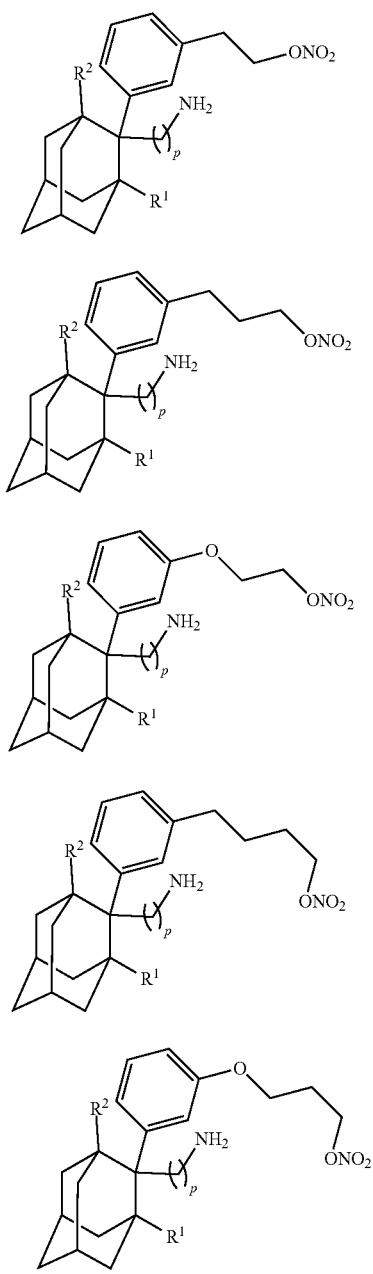

TABLE 3

For each subgenus IVA-i, IVA-ii, IVA-iii,
IVA-iv, IVA-v, IVA-vi and IVA-vii

| p | R¹ | R² |
|---|---|---|
| 0, 1, 2 and 3 | hydrogen | hydrogen |
| 0, 1, 2 and 3 | methyl | methyl |
| 0, 1, 2 and 3 | hydrogen | methyl |
| 0, 1, 2 and 3 | methyl | hydrogen |
| 0, 1, 2 and 3 | ethyl | ethyl |

TABLE 3-continued

For each subgenus IVA-i, IVA-ii, IVA-iii,
IVA-iv, IVA-v, IVA-vi and IVA-vii

| p | R¹ | R² |
|---|---|---|
| 0, 1, 2 and 3 | hydrogen | ethyl |
| 0, 1, 2 and 3 | ethyl | hydrogen |
| 0, 1, 2 and 3 | n-propyl | n-propyl |
| 0, 1, 2 and 3 | hydrogen | n-propyl |
| 0, 1, 2 and 3 | n-propyl | hydrogen |
| 0, 1, 2 and 3 | isopropyl | isopropyl |
| 0, 1, 2 and 3 | hydrogen | isopropyl |
| 0, 1, 2 and 3 | isopropyl | hydrogen |
| 0, 1, 2 and 3 | n-butyl | n-butyl |
| 0, 1, 2 and 3 | hydrogen | n-butyl |
| 0, 1, 2 and 3 | n-butyl | hydrogen |
| 0, 1, 2 and 3 | isobutyl | isobutyl |
| 0, 1, 2 and 3 | hydrogen | isobutyl |
| 0, 1, 2 and 3 | isobutyl | hydrogen |
| 0, 1, 2 and 3 | sec-butyl | sec-butyl |
| 0, 1, 2 and 3 | hydrogen | sec-butyl |
| 0, 1, 2 and 3 | sec-butyl | hydrogen |
| 0, 1, 2 and 3 | —CH$_2$—ONO$_2$ | —CH$_2$—ONO$_2$ |
| 0, 1, 2 and 3 | hydrogen | —CH$_2$—ONO$_2$ |
| 0, 1, 2 and 3 | —CH$_2$—ONO$_2$ | hydrogen |
| 0, 1, 2 and 3 | —(CH$_2$)$_2$—ONO$_2$ | —(CH$_2$)$_2$—ONO$_2$ |
| 0, 1, 2 and 3 | hydrogen | —(CH$_2$)$_2$—ONO$_2$ |
| 0, 1, 2 and 3 | —(CH$_2$)$_2$—ONO$_2$ | hydrogen |
| 0, 1, 2 and 3 | —(CH$_2$)$_3$—ONO$_2$ | —(CH$_2$)$_3$—ONO$_2$ |
| 0, 1, 2 and 3 | hydrogen | —(CH$_2$)$_3$—ONO$_2$ |
| 0, 1, 2 and 3 | —(CH$_2$)$_3$—ONO$_2$ | hydrogen |
| 0, 1, 2 and 3 | —CH$_2$CH(ONO$_2$)CH$_3$ | —CH$_2$CH(ONO$_2$)CH$_3$ |
| 0, 1, 2 and 3 | hydrogen | —CH$_2$CH(ONO$_2$)CH$_3$ |
| 0, 1, 2 and 3 | —CH$_2$CH(ONO$_2$)CH$_3$ | hydrogen |
| 0, 1, 2 and 3 | —CH$_2$CH(CH$_3$)CH$_2$—ONO$_2$ | —CH$_2$CH(CH$_3$)CH$_2$—ONO$_2$ |
| 0, 1, 2 and 3 | hydrogen | —CH$_2$CH(CH$_3$)CH$_2$—ONO$_2$ |
| 0, 1, 2 and 3 | —CH$_2$CH(CH$_3$)CH$_2$—ONO$_2$ | hydrogen | and pharmaceutically acceptable salts (e.g., HCl and HBr salts), solvates, hydrates, clathrates, polymorphs and stereoisomers thereof.

41. The compound of embodiment 40, which is selected from:

91
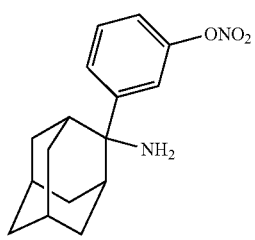
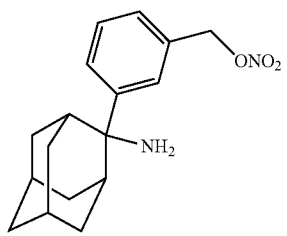
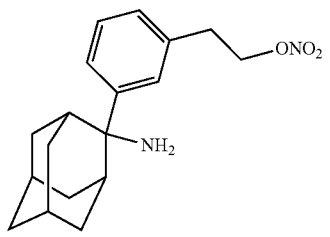
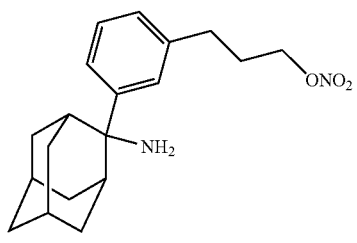
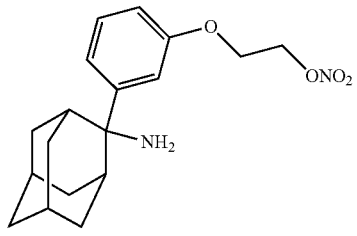
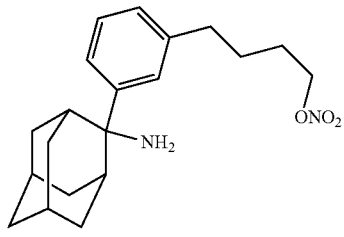
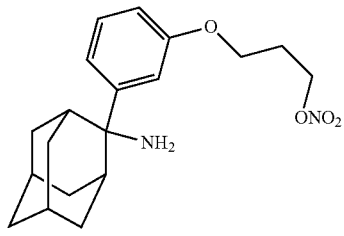
92
-continued
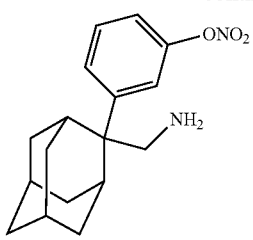
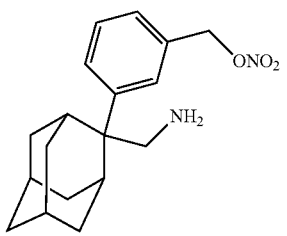
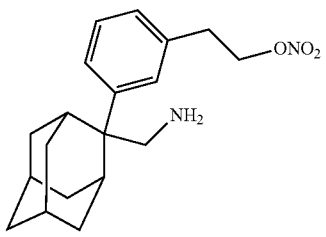
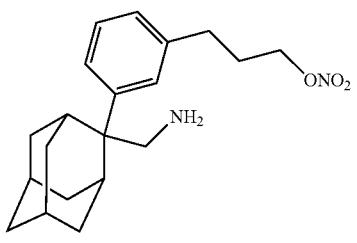
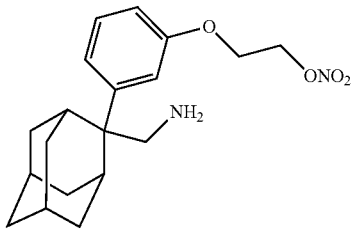
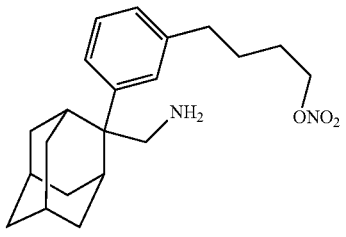
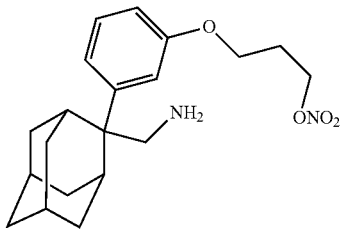

-continued
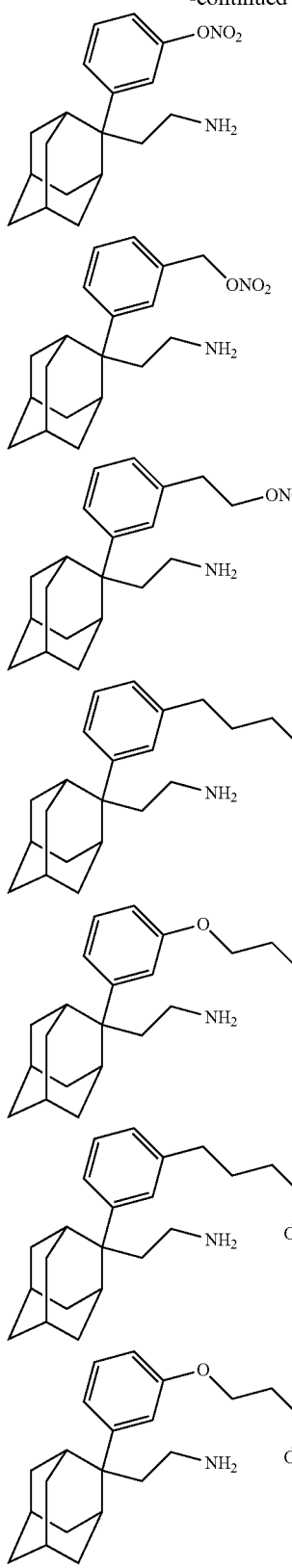
and pharmaceutically acceptable salts (e.g., HCl and HBr salts), solvates, hydrates, clathrates, polymorphs and stereoisomers thereof.
42. A compound of Formula IVB selected from the compounds shown in Table 4:
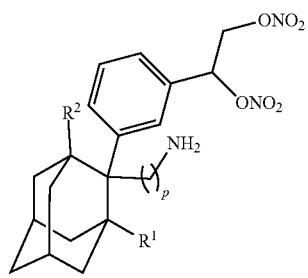
IVB-i
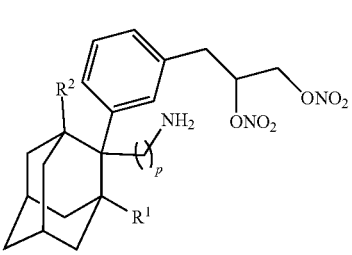
IVB-ii
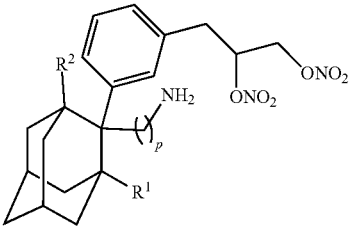
IVB-iii
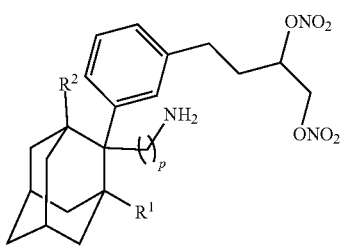
IVB-iv
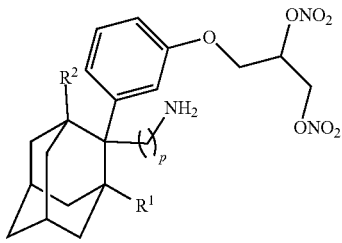
IVB-v
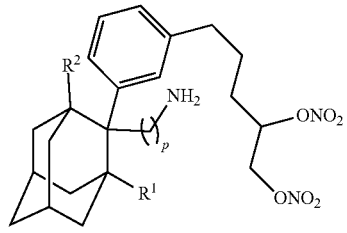
IVB-vi
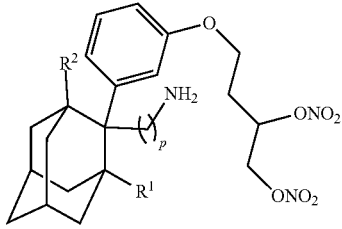

TABLE 4

For each subgenus IVB-i, IVB-ii, IVB-iii, IVB-iv, IVB-v and IVB-vi

| p | R¹ | R² |
|---|---|---|
| 0, 1, 2 and 3 | hydrogen | hydrogen |
| 0, 1, 2 and 3 | methyl | methyl |
| 0, 1, 2 and 3 | hydrogen | methyl |
| 0, 1, 2 and 3 | methyl | hydrogen |
| 0, 1, 2 and 3 | ethyl | ethyl |
| 0, 1, 2 and 3 | hydrogen | ethyl |
| 0, 1, 2 and 3 | ethyl | hydrogen |
| 0, 1, 2 and 3 | n-propyl | n-propyl |
| 0, 1, 2 and 3 | hydrogen | n-propyl |
| 0, 1, 2 and 3 | n-propyl | hydrogen |
| 0, 1, 2 and 3 | isopropyl | isopropyl |
| 0, 1, 2 and 3 | hydrogen | isopropyl |
| 0, 1, 2 and 3 | isopropyl | hydrogen |
| 0, 1, 2 and 3 | n-butyl | n-butyl |
| 0, 1, 2 and 3 | hydrogen | n-butyl |
| 0, 1, 2 and 3 | n-butyl | hydrogen |
| 0, 1, 2 and 3 | isobutyl | isobutyl |
| 0, 1, 2 and 3 | hydrogen | isobutyl |
| 0, 1, 2 and 3 | isobutyl | hydrogen |
| 0, 1, 2 and 3 | sec-butyl | sec-butyl |
| 0, 1, 2 and 3 | hydrogen | sec-butyl |
| 0, 1, 2 and 3 | sec-butyl | hydrogen |
| 0, 1, 2 and 3 | —CH$_2$—ONO$_2$ | —CH$_2$—ONO$_2$ |
| 0, 1, 2 and 3 | hydrogen | —CH$_2$—ONO$_2$ |
| 0, 1, 2 and 3 | —CH$_2$—ONO$_2$ | hydrogen |
| 0, 1, 2 and 3 | —(CH$_2$)$_2$—ONO$_2$ | —(CH$_2$)$_2$—ONO$_2$ |
| 0, 1, 2 and 3 | hydrogen | —(CH$_2$)$_2$—ONO$_2$ |
| 0, 1, 2 and 3 | —(CH$_2$)$_2$—ONO$_2$ | hydrogen |
| 0, 1, 2 and 3 | —(CH$_2$)$_3$—ONO$_2$ | —(CH$_2$)$_3$—ONO$_2$ |
| 0, 1, 2 and 3 | hydrogen | —(CH$_2$)$_3$—ONO$_2$ |
| 0, 1, 2 and 3 | —(CH$_2$)$_3$—ONO$_2$ | hydrogen |
| 0, 1, 2 and 3 | —CH$_2$CH(ONO$_2$)CH$_3$ | —CH$_2$CH(ONO$_2$)CH$_3$ |
| 0, 1, 2 and 3 | hydrogen | —CH$_2$CH(ONO$_2$)CH$_3$ |
| 0, 1, 2 and 3 | —CH$_2$CH(ONO$_2$)CH$_3$ | hydrogen |
| 0, 1, 2 and 3 | —CH$_2$CH(CH$_3$)CH$_2$—ONO$_2$ | —CH$_2$CH(CH$_3$)CH$_2$—ONO$_2$ |
| 0, 1, 2 and 3 | hydrogen | —CH$_2$CH(CH$_3$)CH$_2$—ONO$_2$ |
| 0, 1, 2 and 3 | —CH$_2$CH(CH$_3$)CH$_2$—ONO$_2$ | hydrogen | and pharmaceutically acceptable salts (e.g., HCl and HBr salts), solvates, hydrates, clathrates, polymorphs and stereoisomers thereof.

43. The compound of embodiment 42, which is selected from:

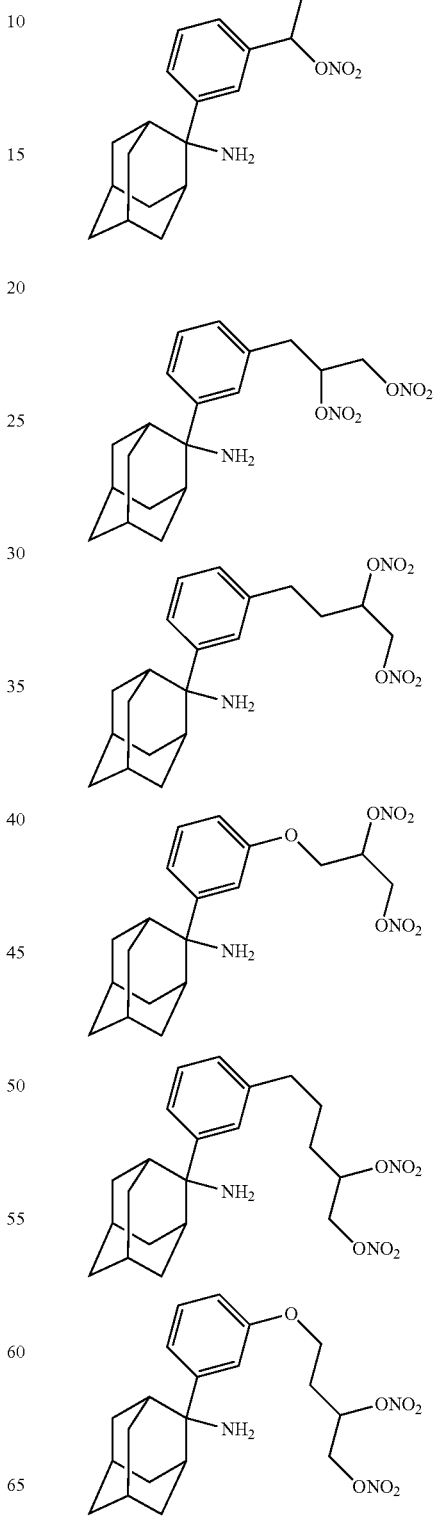

-continued

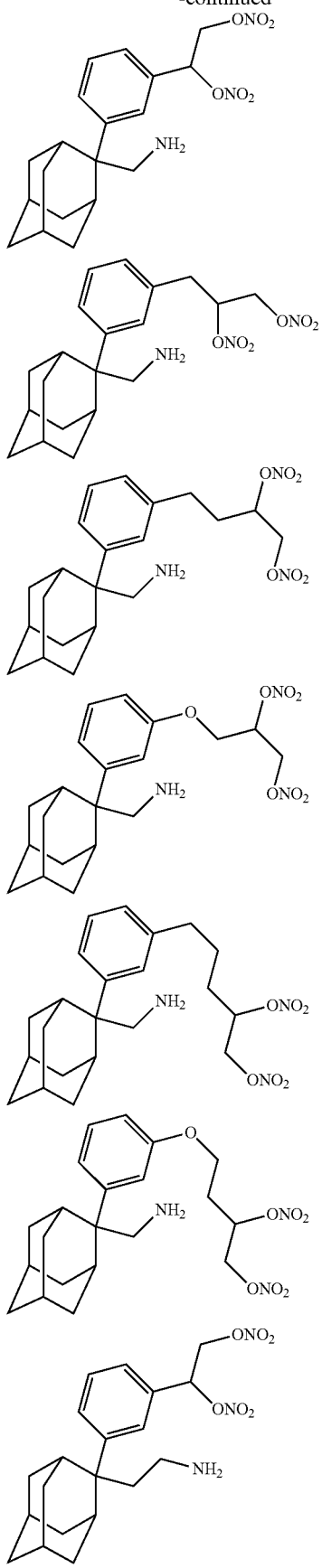

-continued

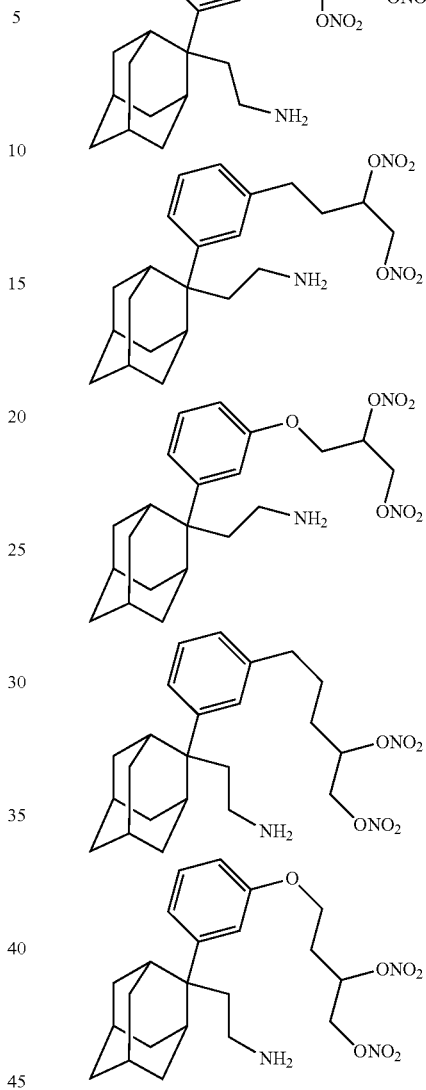

and pharmaceutically acceptable salts (e.g., HCl and HBr salts), solvates, hydrates, clathrates, polymorphs and stereoisomers thereof.

44. A pharmaceutical composition comprising a compound of any one of the preceding embodiments, or a pharmaceutically acceptable salt, solvate, hydrate, clathrate, polymorph or stereoisomer thereof, and one or more pharmaceutically acceptable excipients or carriers.

45. A method of treating a disorder of the central nervous system (CNS), comprising administering to a subject in need of treatment a therapeutically effective amount of a compound of any one of embodiments 1 to 43, or a pharmaceutically acceptable salt, solvate, hydrate, clathrate, polymorph or stereoisomer thereof.

46. The method of embodiment 45, wherein the CNS disorder is a neurodegenerative disorder.

47. The method of embodiment 46, wherein the neurodegenerative disorder is selected from dementia (e.g., Alzheimer's disease, vascular dementia, dementia with Lewy bodies, frontotemporal dementia and HIV-associated dementia), Huntington's disease, Parkinson's disease, multiple system atrophy (Shy-Drager syndrome), cerebellar degeneration, ataxia (e.g., cerebellar ataxia, spinocerebellar ataxia, Friedreich's ataxia and ataxia-telangiectasia [Louis-Bar syndrome]), motor neuron diseases (e.g., amyotrophic lateral sclerosis [ALS], primary lateral sclerosis [PLS], progressive muscular atrophy [PMA] and spinal muscular atrophy [SMA]), multiple sclerosis, vision impairment or loss caused by neurodegeneration of the visual pathway (e.g., optic neuropathy/atrophy, glaucoma and age-related macular degeneration), and sensorineural hearing loss.

48. The method of embodiment 47, wherein the neurodegenerative disorder is Alzheimer's disease, vascular dementia, Huntington's disease, Parkinson's disease or ALS.

49. The method of embodiment 45, wherein the CNS disorder is selected from cerebrovascular disorders (including brain ischemia [including acute ischemia such as stroke, chronic ischemia such as vascular dementia, cerebral ischemia/reperfusion injury, and neurological damage caused by low oxygen or/and glucose levels in the brain], intracerebral hemorrhage and retinopathy), brain injury and trauma (including traumatic brain injury, diffuse axonal injury, primary and secondary brain injury, focal and diffuse brain injury, anoxic and hypoxic brain injury, intracerebral hemorrhage and brain edema), spinal cord injury (due to, e.g., trauma, ischemia or a degenerative disorder), epilepsy (including neurological damage caused by epileptic seizures), dyskinesia (e.g., levodopa-induced dyskinesia and tardive dyskinesia), spasticity, pain (e.g., acute pain, chronic pain, allodynia, complex regional pain syndrome [CRPS], fibromyalgia, hyperalgesia, inflammatory pain, neuropathic pain, postoperative pain, cancer-related pain, drug-induced pain and injury-induced pain), headaches (including primary headaches [e.g., migraine, cluster headache and tension headache] and secondary headaches [due to, e.g., a cerebrovascular disorder, a brain bleed, a brain injury, a brain infection or a brain tumor), neurodevelopmental disorders (including MEF2C haploinsufficiency syndrome [MCHS], autism spectrum disorder [including autism], developmental delay, intellectual disability, fragile X syndrome, attention-deficit hyperactivity disorder [ADHD] and schizophrenia), mood disorders (including depressive disorders [e.g., major depressive disorder and treatment-resistant depression], bipolar disorders and dementia-related mood disorders), and anxiety disorders (including generalized anxiety disorder, stress disorders [e.g., acute stress disorder, post-traumatic stress disorder and chronic stress], and obsessive-compulsive disorder).

50. The method of embodiment 49, wherein the CNS disorder is brain ischemia, traumatic brain injury, epilepsy, pain or autism spectrum disorder.

51. The method of any one of embodiments 45 to 50, wherein the compound is administered orally.

52. The method of any one of embodiments 45 to 50, wherein the compound is administered parenterally (e.g., intravenously, intramuscularly or subcutaneously).

53. The method of any one of embodiments 45 to 52, wherein the compound is administered in a daily dose of from about 1, 5 or 10 mg to about 100 mg.

54. The method of embodiment 53, wherein the compound is administered in a daily dose of about 1, 5, 10, 15, 20, 25, 30, 40, 50, 60, 70, 80, 90 or 100 mg.

55. The method of embodiment 53 or 54, wherein the compound is administered in a daily dose of from about 5 or 10 mg to about 50 mg.

56. The method of any one of embodiments 45 to 55, further comprising administering an additional therapeutic agent.

57. A compound of any one of embodiments 1 to 43, or a pharmaceutically acceptable salt, solvate, hydrate, clathrate, polymorph or stereoisomer thereof, for use as a medicament.

58. A composition comprising a compound of any one of embodiments 1 to 43, or a pharmaceutically acceptable salt, solvate, hydrate, clathrate, polymorph or stereoisomer thereof, for use as a medicament.

59. Use of a compound of any one of embodiments 1 to 43, or a pharmaceutically acceptable salt, solvate, hydrate, clathrate, polymorph or stereoisomer thereof, in the preparation of a medicament.

60. The compound, composition or use of embodiment 57, 58 or 59, respectively, wherein the medicament is for use in the treatment of a CNS disorder, such as a neurodegenerative disorder or a non-neurodegenerative disorder.

61. A kit comprising:
   a compound of any one of embodiments 1 to 43, or a pharmaceutically acceptable salt, solvate, hydrate, clathrate, polymorph or stereoisomer thereof; and
   instructions for administering the compound to treat a CNS disorder, such as a neurodegenerative disorder or a non-neurodegenerative disorder.

X. EXAMPLES

The following examples are intended only to illustrate the disclosure. Other synthetic processes, assays, studies, protocols, procedures, methodologies, reagents and conditions may alternatively be used as appropriate.

Abbreviations: DCM=dichloromethane; DMF=N,N-dimethylformamide; EGTA=ethylene glycol-bis(β-aminoethyl ether)-N,N,N',N'-tetraacetic acid; HEPES=4-(2-hydroxyethyl)-1-piperazineethanesulfonic acid; MTBE=methyl tert-butyl ether; PBS=phosphate-buffered saline; RT=room/ambient temperature; TEA=triethylamine; THF=tetrahydrofuran Synthesis of Aminoadamantyl Nitrate Compounds Representative syntheses of compounds of Formulas I and III are shown below.

Example 1. Synthesis of 1-Aminomethylene-3,5-dimethyl-7-nitratemethyladamantane Hydrochloride

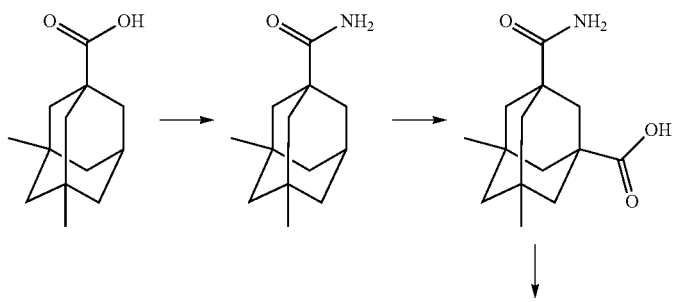

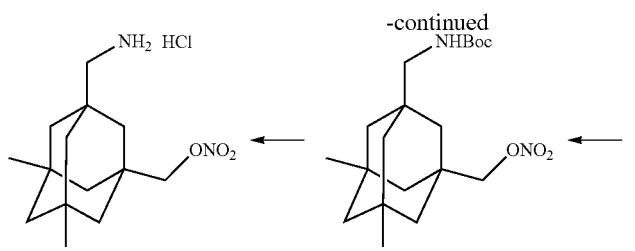
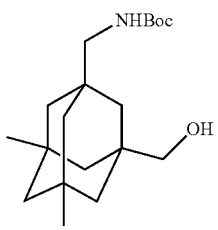

To a solution of 1-carboxy-3,5-dimethyladamantane (5 g, 24 mmol, available from Sigma-Aldrich) in DCM (20 mL) was added DMF (2 drops) followed by oxalyl chloride (6.2 mL, 72 mmol) dropwise. The reaction mixture was stirred overnight at room temperature and then concentrated in vacuo. The resulting oil was diluted in THF (10 mL) and added to an ice-cooled solution of THF (20 mL) and 28% ammonium hydroxide (5 mL). The reaction was stirred for 1 hr, diluted with MTBE, washed with brine, dried over sodium sulfate and concentrated to give 1-carboxamide-3, 5-dimethyladamantane as a white solid.

1-Carboxamide-3,5-dimethyladamantane (2 g, 9.7 mmol) was added to fuming sulfuric acid (30 mL) at 0° C. over 1 hr. The reaction mixture was stirred at 0° C. for 2 hr and then was treated with 95% formic acid (4 mL) dropwise. The mixture was stirred at 0° C. for 2 hr and then was poured carefully onto ice (200 g). The precipitate was filtered, washed with water and dried under vacuum to afford 1-carboxamide-3,5-dimethyl-7-carboxy adamantane.

LiAlH$_4$ (1 M in THF, 4 mL) was added to a solution of 1-carboxamide-3,5-dimethyl-7-carboxyadamantane (620 mg, 2.5 mmol) in THF (15 mL). The reaction mixture was stirred at 40° C. for 24 hr, and then was quenched with Glauber's salt, diluted with ether, and stirred for 1 hr. The solids were removed by filtration, and the organic layer of the filtrate was concentrated. The residue was dissolved in acetonitrile (10 mL) and treated with saturated sodium bicarbonate solution (10 mL) and BOC$_2$O (545 mg, 2.5 mmol), and the resulting mixture was stirred for 8 hr. The mixture was diluted with MTBE, washed with brine, dried over sodium sulfate, and concentrated. The residue was purified by silica gel column chromatography (10-100% EtOAc/hexanes) to give 1-(N-Boc-aminomethylene)-3,5-dimethyl-7-hydroxymethyladamantane. MS: m/z 324 [M+H]$^+$ A chilled solution (0° C.) of acetyl nitrate (420 μL) formed from a mixture of fuming nitric acid and acetic anhydride (1:1.5 v/v) was added to a solution of 1-(N-Boc-aminomethylene)-3,5-dimethyl-7-hydroxymethyladamantane (225 mg, 0.7 mmol) in DCM (5 mL) at 0° C. The reaction mixture was stirred cold for 15 min and then was quenched with saturated sodium bicarbonate, extracted into DCM, washed with water, dried over sodium sulfate and concentrated. The residue was purified by silica gel column chromatography (10-50% EtOAc/hexanes) to give 1-(N-Boc-aminomethylene)-3,5-dimethyl-7-nitratemethyladamantane. MS: m/z 369 [M+H]$^+$ A solution of HCl in dioxane (4 N, 2 mL) was added to 1-(N-Boc-aminomethylene)-3,5-dimethyl-7-nitratemethyladamantane (150 mg). The reaction mixture was stirred at room temperature for 30 min and then was concentrated in vacuo. The residue was triturated with ether and filtered to provide 1-aminomethylene-3,5-dimethyl-7-nitratemethyladamantane hydrochloride. MS: m/z 269 [M+H]$^+$ The following compounds were synthesized using similar procedures as above: 1-(2-aminoethyl)-3,5-dimethyl-7-nitratemethyladamantane hydrochloride starting from 1-acetic acid-3,5-dimethyladamantane (available from Sigma-Aldrich).

Example 2. Synthesis of 1-Aminomethylene-3,5-dimethyl-7-nitrateadamantane Hydrochloride

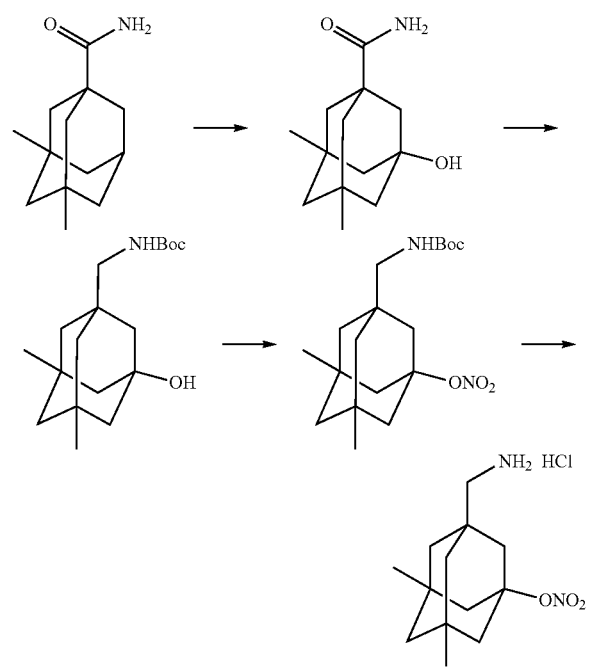

1-Carboxamide-3,5-dimethyladamantane (2 g, 9.7 mmol, prepared as described in Example 1) was added to fuming sulfuric acid (30 mL) at 0° C. over 1 hr. The reaction mixture was stirred at 0° C. for 2 hr and then was poured carefully onto ice (200 g). The precipitate was filtered, washed with water and dried under vacuum to give 1-carboxamide-3,5-dimethyl-7-hydroxyadamantane. MS: m/z 224 [M+H]+

LiATH$_4$ (1 M in THF, 5 mL) was added to a solution of 1-carboxamide-3,5-dimethyl-7-hydroxyadamantane (830 mg, 3.7 mmol) in THF (20 mL). The reaction mixture was stirred at 40° C. for 24 hr, and then was quenched with Glauber's salt, diluted with ether, and stirred for 1 hr. The solids were removed by filtration, and the organic layer of the filtrate was concentrated. The residue was dissolved in acetonitrile (10 mL) and treated with saturated sodium bicarbonate solution (10 mL) and BOC$_2$O (806 mg, 3.7 mmol), and the resulting mixture was stirred for 10 hr. The mixture was diluted with MTBE, washed with brine, dried over sodium sulfate, and concentrated. The residue was purified by silica gel column chromatography (10-100% EtOAc/hexanes) to afford 1-(N-Boc-aminomethylene)-3,5-dimethyl-7-hydroxyadamantane. MS: m/z 310 [M+H]+

A chilled solution (0° C.) of acetyl nitrate (300 μL) formed from a mixture of fuming nitric acid and acetic anhydride (1:1.5 v/v) was added to a solution of 1-(N-Boc-aminomethylene)-3,5-dimethyl-7-hydroxyadamantane (150 mg, 0.5 mmol) in DCM (3 mL) at 0° C. The reaction mixture was stirred cold for 15 min and then was quenched with saturated sodium bicarbonate, extracted into DCM, washed with water, dried over sodium sulfate and concentrated. The residue was purified by silica gel column chromatography (10-50% EtOAc/hexanes) to furnish 1-(N-Boc-aminomethylene)-3,5-dimethyl-7-nitrateadamantane. MS: m/z 355 [M+H]+

A solution of HCl in dioxane (4 N, 2 mL) was added to 1-(N-Boc-aminomethylene)-3,5-dimethyl-7-nitrateadamantane (85 mg). The reaction mixture was stirred at room temperature for 30 min and then was concentrated in vacuo. The residue was triturated with ether and filtered to provide 1-aminomethylene-3,5-dimethyl-7-nitrateadamantane hydrochloride. MS: m/z 255 [M+H]+

The following compounds can be synthesized using similar procedures as above: 1-(2-aminoethyl)-3,5-dimethyl-7-nitrateadamantane hydrochloride starting from 1-acetic acid-3,5-dimethyladamantane (available from Sigma-Aldrich).

Example 3. Synthesis of 1-(2-Aminoethyl)-3,5-dimethyl-7-(1-nitratepropyl)adamantane Hydrochloride nium chloride and extracted with ethyl acetate. The organic layer was washed with brine, dried over sodium sulfate and concentrated to provide a crude mixture of the ethyl ketone and the dialkylated alcohol. Purification by silica gel column chromatography using ethyl acetate/hexane as the eluent provided 1-carboxamidemethyl-3,5-dimethyl-7-(propan-1-one)adamantane (86 mg).

LiAlH4 (1 M in THF, 36 mg, 0.93 mmol) was added to a cooled (ice bath) solution of 1-carboxamidemethyl-3,5-dimethyl-7-(propan-1-one)adamantane (86 mg, 0.31 mmol) in THF (2 mL) over 5 min, and the reaction mixture was then heated at 50° C. and stirred for 4 hr. The reaction was quenched with sodium sulfate decahydrate. The resulting solid was filtered and washed with THF (2×5 mL), and the filtrate was concentrated. Purification by silica gel column chromatography using DCM/methanol as the eluent furnished 1-(2-aminoethyl)-3,5-dimethyl-7-(1-hydroxypropyl)adamantane (72 mg). The amino group was protected with a Boc group using BOC2O according to a similar procedure as described in Example 1.

1-(2-Aminoethyl)-3,5-dimethyl-7-(1-nitratepropyl)adamantane hydrochloride was prepared starting from 1-(N-Boc-2-aminoethyl)-3,5-dimethyl-7-(1-hydroxypropyl)adamantane using similar procedures as described for the preparation of 1-aminomethylene-3,5-dimethyl-7-nitratemethyladamantane hydrochloride starting from 1-(N-Boc-aminomethylene)-3,5-dimethyl-7-hydroxymethyladamantane in Example 1.

The following compounds can be synthesized using similar procedures as above: 1-(Aminomethylene)-3,5-dimethyl-

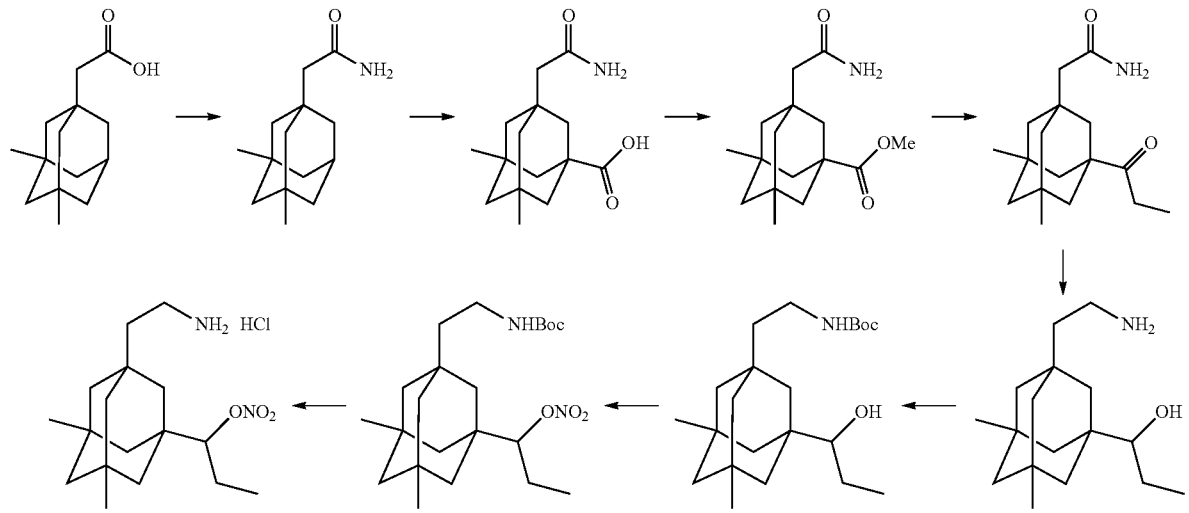

1-Carboxamidemethyl-3,5-dimethyl-7-carboxyadamantane was prepared starting from 1-acetic acid-3,5-dimethyladamantane (available from Sigma-Aldrich) using similar procedures as described for the preparation of 1-carboxamide-3,5-dimethyl-7-carboxyadamantane starting from 1-carboxy-3,5-dimethyladamantane in Example 1. The methyl ester was formed using TMS diazomethane.

Ethylmagnesium bromide (3 M in ether, 208 mg, 1.6 mmol) was added to a cooled solution of 1-carboxamidemethyl-3,5-dimethyl-7-(carboxylic acid methyl ester)adamantane (220 mg, 0.78 mmol) in THF (5 mL) over 5 min, and the reaction mixture in the ice bath was stirred for 2 hr. The reaction was quenched with a saturated solution of ammo- 7-(1-nitratepropyl)adamantane hydrochloride starting from 1-carboxy-3,5-dimethyladamantane.

Furthermore, 1-(2-aminoethyl)-3,5-dimethyl-7-(1-nitrate-ethyl)adamantane hydrochloride and 1-(aminomethylene)-3,5-dimethyl-7-(1-nitrate-ethyl)adamantane hydrochloride can be synthesized using similar procedures as above. MeMgBr can be reacted with the corresponding methyl ester to form the methyl ketone, or the methyl ketone can be formed by reacting MeLi with the corresponding carboxylic acid according to the procedure described in J. Henkel et al., J. Med. Chem., 25:51-56 (1982).

Example 4. Synthesis of 2-Aminomethylene-2-(3-nitratephenyl)adamantane Hydrochloride

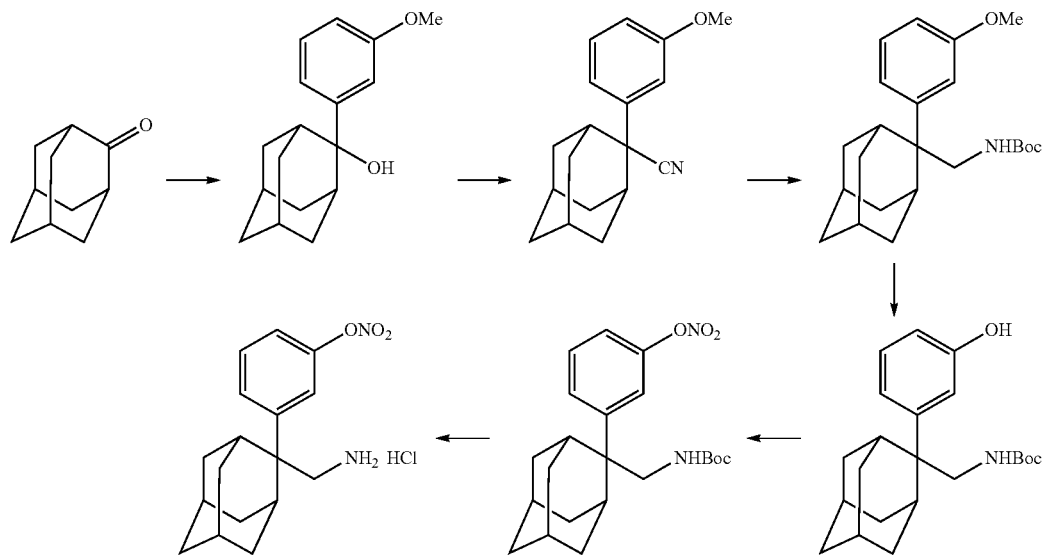

3-Methoxyphenylmagnesium bromide (1 M in THF, 16 mL) was added to a chilled (0° C.) solution of 2-adamantanone (2 g, 13.3 mmol, available from Sigma-Aldrich) in THF (20 mL). The reaction mixture was stirred at room temperature for 3 days over the weekend, and then was quenched with saturated sodium bicarbonate solution, diluted with MTBE, washed with brine, dried over sodium sulfate and concentrated. The residue was purified by silica gel column chromatography (30% EtOAc/hexanes) to give 2-hydroxy-2-(3-methoxyphenyl)adamantane.

A chilled (0° C.) solution of 2-hydroxy-2-(3-methoxyphenyl)adamantane (3.4 g, 13.2 mmol) in chloroform (10 mL) was treated with TMSCN (1.84 mL, 13.9 mmol) followed by $BF_3 \cdot OEt_2$ (1.96 mL, 15.8 mmol). The reaction mixture was allowed to warm to room temperature and stirred for 3 hr. The reaction was quenched with sodium bicarbonate solution, extracted into DCM, dried over sodium sulfate and concentrated. The residue was purified by silica gel column chromatography (20% EtOAc/hexanes) to afford 2-cyano-2-(3-methoxyphenyl)adamantane.

$LiAlH_4$ (1 M in $Et_2O$, 27.8 mL) was added dropwise to a solution of 2-cyano-2-(3-methoxyphenyl)adamantane (2.48 g, 9.2 mmol) in THF (20 mL), and the reaction mixture was stirred at 50° C. overnight. The mixture was allowed to cool to room temperature, quenched with Glauber's salt, diluted with ether, and stirred for 1 hr. The solids were removed by filtration, and the organic layer of the filtrate was concentrated. The residue was dissolved in acetonitrile (30 mL), treated with saturated sodium bicarbonate solution (30 mL) and $BOC_2O$ (2 g, 9.2 mmol), and stirred for 14 hr. The mixture was diluted with MTBE, washed with brine, dried over sodium sulfate, and concentrated. The residue was purified by silica gel column chromatography (10-100% EtOAc/hexanes) to furnish 2-(N-Boc-aminomethylene)-2-(3-methoxyphenyl)adamantane. MS: m/z 372 [M+H]$^+$ A solution of 2-(N-Boc-aminomethylene)-2-(3-methoxyphenyl)adamantane (1.1 g, 4.0 mmol) in dichloroethane (20 mL) was treated with $BBr_3 \cdot SMe_2$ (1 M, 12 mmol), and the reaction mixture was stirred at 80° C. for 24 hr. The reaction was quenched with saturated sodium bicarbonate, diluted with DCM, washed with brine, dried over sodium sulfate, and concentrated. The residue was purified by silica gel column chromatography (20-60% EtOAc/hexanes) to provide 2-(N-Boc-aminomethylene)-2-(3-hydroxyphenyl)adamantane. MS: m/z 358 [M+H]$^+$ 2-Aminomethylene-2-(3-nitratephenyl)adamantane hydrochloride was prepared starting from 2-(N-Boc-aminomethylene)-2-(3-hydroxyphenyl)adamantane using similar procedures as described for the preparation of 1-aminomethylene-3,5-dimethyl-7-nitratemethyladamantane hydrochloride starting from 1-(N-Boc-aminomethylene)-3,5-dimethyl-7-hydroxymethyl-adamantane in Example 1.

Example 5. Synthesis of 2-Aminomethylene-2-[3-(2-nitrate-ethoxy)phenyl]adamantane Hydrochloride

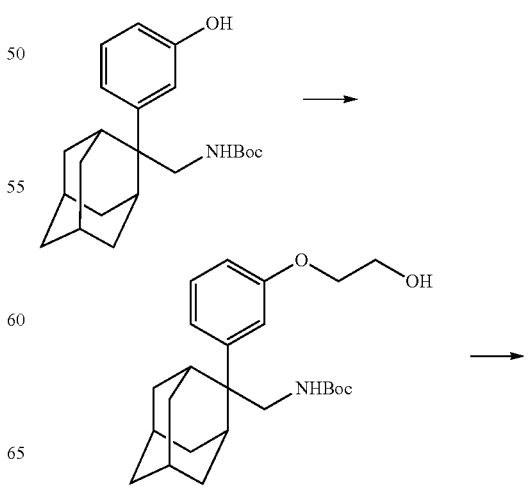

-continued

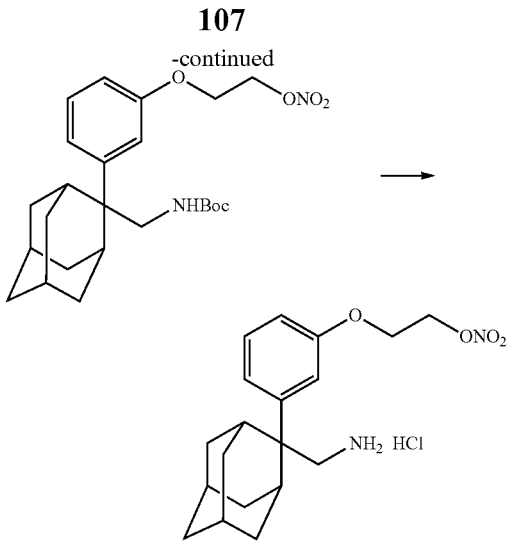

A solution of 2-(N-Boc-aminomethylene)-2-(3-hydroxyphenyl)adamantane (230 mg, 0.64 mmol, prepared as described in Example 4) in DMF (5 mL) was treated with potassium carbonate (200 mg) and 2-benzyloxy-1-bromoethane (172 mg, 0.8 mmol), and the reaction mixture was stirred at 80° C. for 24 hr. The mixture was diluted with MTBE, washed with brine, dried over sodium sulfate, and concentrated. The residue was dissolved in ethanol (10 mL) and treated with 10% Pd—C(20 mg), and the reaction mixture was stirred under 1 atm hydrogen at room temperature for 18 hr. The mixture was filtered, and the filtrate was concentrated. The residue was purified by silica gel column chromatography (20-100% EtOAc/hexanes) to provide 2-(N-Boc-aminomethylene)-2-[3-(2-hydroxyethoxy)phenyl]adamantane. MS: m/z 402 [M+H]$^+$ 2-Aminomethylene-2-[3-(2-nitrate-ethoxy)phenyl]adamantane hydrochloride was prepared starting from 2-(N-Boc-aminomethylene)-2-[3-(2-hydroxyethoxy)phenyl]adamantane using similar procedures as described for the preparation of 1-aminomethylene-3,5-dimethyl-7-nitratemethyladamantane hydrochloride starting from 1-(N-Boc-aminomethylene)-3,5-dimethyl-7-hydroxymethyl-adamantane in Example 1.

The following compounds were synthesized using similar procedures as above: 2-Aminomethylene-2-[3-(3-nitratepropyloxy)phenyl]adamantane hydrochloride.

Example 6. Syntheses of Various Aminoadamantyl Nitrate Compounds

FIG. 1 describes the synthesis of aminoadamantyl nitrate compounds 9a-e, 13a-e and 16a-e. 1-Bromoadamantanes 2b-d can be generated from adamantanes 1b-d as described in J. Henkel et al., *J. Med. Chem.*, 25:51-56 (1982) ("Henkel"), while 1-bromoadamantane 2a can be generated from the corresponding 1-hydroxyadamantane as described in Henkel. 1,3-Di-n-propyladamantane 1e can be prepared by reacting 1,3-adamantanediacetic acid (available from Sigma-Aldrich) with CH$_3$Li followed by Wolff-Kishner reduction of the resulting 1,3-adamantanediacetone with hydrazine, similar to the preparation of 1-propyladamantane from 1-adamantaneacetic acid as described in Henkel. Adamantane 1e can be brominated using the procedure of Henkel to form 1-bromoadamantane 2e. 1-Bromoadamantanes 2a-e can be converted to 1-cyanoadamantanes 3a-e using NaCN or KCN at elevated temperature. Alternatively, adamantanes 1a-e can be converted to 1-carboxyadamantanes 4a-e and then 1-carboxamideadamantanes 5a-e using procedures described in Example 1.

Aminoadamantyl nitrate compounds 9a-e can be synthesized from 1-cyanoadamantanes 3a-e or 1-carboxamideadamantanes 5a-e using procedures described for the synthesis of 1-aminomethylene-3,5-dimethyl-7-nitrateadamantane hydrochloride in Example 2. Conversion of a cyano group to a —CH$_2$NHBoc group using LiATH$_4$ followed by Boc$_2$O is described in Example 4.

Aminoadamantyl nitrate compounds 13a-e can be synthesized from 1-cyanoadamantanes 3a-e or 1-carboxamideadamantanes 5a-e using procedures described for the synthesis of 1-aminomethylene-3,5-dimethyl-7-nitratemethyladamantane hydrochloride in Example 1.

Aminoadamantyl nitrate compounds 16a-e can be synthesized from 1-(cyano or carboxamide)-5 or 7-carboxyadamantanes 10a-e using procedures described for the synthesis of 1-(2-aminoethyl)-3,5-dimethyl-7-(1-nitratepropyl)adamantane hydrochloride in Example 3. Methyl or ethyl ketones 14a-e can be prepared by reacting carboxyadamantanes 10a-e with MeLi or EtLi, similar to the preparation of 1-adamantaneacetone by reacting 1-adamantaneacetic acid with MeLi as described in Henkel. Alternatively, methyl or ethyl ketones 14a-e can be prepared by reacting the methyl ester of carboxylic acid 10 with MeMgBr or EtMgBr as described in Example 3.

Aminoadamantyl nitrate compounds with R$^1$=H and R$^2$=Me, Et or n-Pr and corresponding to compounds 9a, b and d, 13a, b and d, and 16a, b and d are stereoisomers of compounds 9a, b and d, 13a, b and d, and 16a, b and d. The stereoisomers can be included in a mixture (e.g., an about 1:1 mixture) with compounds 9a, b and d, 13a, b and d, and 16a, b and d, or can be separated from compounds 9a, b and d, 13a, b and d, and 16a, b and d, such as by chiral high-pressure liquid chromatography (HPLC).

Biological Assays and Studies of Aminoadamantyl Nitrate Compounds

Example 7. In Vitro Inhibition of NMDAR-Evoked Current

The antagonistic activity of various aminoadamantyl nitrate compounds on NMDA receptors was assessed in a ScreenPatch IonWorks Barracuda-based assay using HEK293 cells expressing NR1/NR2A ionotropic glutamate receptors. The assay was conducted at ambient temperature. Extracellular buffer (137 mM NaCl, 1 mM KCl, 5 mM CaCl$_2$, 10 mM HEPES, 10 mM glucose, pH 7.4) was loaded into the wells of a PPC plate (11 IL per well). A suspension of NR1/NR2A-expressing HEK293 cells was pipetted into the wells (9 μL per well) of the PPC planar electrode whose intracellular compartment contained an intracellular solution of 50 mM CsCl, 90 mM CsF, 2 mM MgCl$_2$, 5 mM EGTA, 10 mM HEPES, pH 7.2. The holding potential was −70 mV, and the potential during application of a test compound or memantine HCl (positive control) was −40 mV. Whole-cell recording configuration was established via patch perforation with membrane currents recorded by on-board patch clamp amplifiers. One recording (scans) was performed during co-application of a test compound and agonist (EC$_{20}$ L-glutamate) to detect any PAM effect of the test compound. Application of a test compound or memantine HCl consisted of addition of 20 μL of 1× or 2× concentrated solution of the test compound or memantine HCl and co-agonists (3 μM L-glutamate and 50 μM glycine) at 10 μL/s (2 second total application time). The duration of co-exposure/co-application of a test compound or memantine HCl and co-agonists was at least 15 seconds. Activation of NMDA receptors was calculated in three ways based on measurements of peak current amplitudes and current amplitude 2 seconds after agonist addition. The vehicle (agonist) control was 3 µM L-glutamate and 50 µM glycine, and the positive control was memantine HCl. Data acquisition and analysis were performed using IonWorks system software (Molecular Devices Corporation, Union City, California). The $IC_{50}$ of test compounds and memantine HCl was calculated from a dose-response curve generated from 8 different concentrations of the test compounds and memantine HCl. The decrease in current amplitude and current decay after co-application of a test compound or memantine HCl and co-agonists was used to calculate the percent NMDAR channel block.

The following aminoadamantyl nitrate compounds as a hydrochloride salt were tested in the ScreenPatch assay:

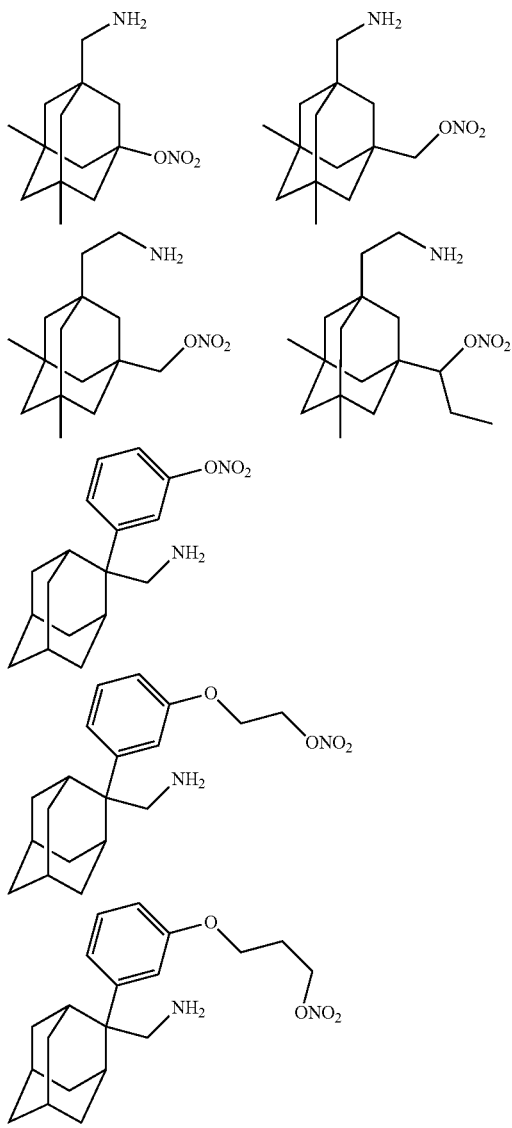

Memantine hydrochloride and all of the aminoadamantyl nitrate compounds, except for the phenylnitrate compound, had an $IC_{50} \leq$ about 20 µM in the ScreenPatch assay.

Example 8. Inhibition of NMDA Receptor Function in Patch-Clamp Electrophysiology Patch-clamp electrophysiology experiments are performed to assess the ability of test compounds to block NMDA-evoked currents by a dual mechanism of channel blockade at or near the $Mg^{2+}$-binding site and S-nitrosylation of the redox modulatory site.

Preparation of Cerebrocortical Neurons

Tissues containing parieto-occipital cortex from C57BL/6 mice are incubated twice (20 min each time) at 37° C. in Hanks' balanced salt solution (HBSS), pH 7.22, containing 3.5 U/mL papain, 1.7 mM cysteine, 20 µg/mL bovine serum albumin and NMDAR blockers (100 µM DL-APV [DL-amino-5-phosphonovaleric acid], 1 mM kynurenic acid, 10 mM $MgCl_2$). After being rinsed, the tissues are gently washed with a 1-mL glass serological pipette. The supernatant is placed onto glass cover slips coated with poly-L-lysine. Cells are plated 2-10 hr before electrophysiological recordings.

Electrophysiological Recordings of Dissociated Neurons

Single-channel currents from outside-out patches and whole-cell currents from cerebrocortical neurons are recorded at 20-25° C. by an experimenter masked to genotype, as described in Chen et al., *J Neurosci.*, 12:4427-4436 (1992) and Chen et al., *J. Physiol.* (Lond), 499:27-46 (1997). Briefly, electrodes are filled with an intracellular solution (pH 7.22) containing 120 mM CsCl, 20 mM TEA-Cl, 10 mM HEPES, 2.25 mM EGTA, 1 mM $CaCl_2$, and 2 mM $MgCl_2$. The external solution is a modified HBSS with 10 µM glycine in which $Mg^{2+}$ salts are omitted, and $[Ca^{2+}]_O$ is adjusted to 2.5 mM or lowered to the nanomolar range by adding 1 mM EGTA in the absence of added $CaCl_2$. (Low $[Ca^{2+}]_O$ is used to minimize subconductance states during single-channel recording). A potential problem in electrophysiology experiments is rundown of the NMDA-evoked response—keeping $[Ca^{2+}]_O$ low and using an ATP-regenerating system helps. Moreover, since dithiothreitol (DTT, 0.5-2 mM) can reverse the effect of the nitrate group of aminoadamantyl nitrate compounds (and of other oxidizing agents), the effects of rundown can be distinguished from real NMDAR inhibition by $NO^+$ donation to thiol group(s). When multiple compounds are tested in a single experiment, significance of the results is evaluated with an analysis of variance followed by a Scheffé multiple comparison of means. The dwell time of the test compounds in the NMDAR channel and their effect on excitatory postsynaptic current (EPSC) amplitude are assessed [Chen (1997, supra) and Chen et al., *Neurosci.*, 86:1121-1132 (1998)]. Memantine and nitroglycerin (NTG) are used are positive controls in the experiments.

Example 9. Recordings of NMDAR-Mediated Currents Under Whole-Cell Clamp

The protocol for performing whole-cell recordings of NMDAR-mediated currents using rat cerebrocortical cultures and hippocampal autaptic cultures is described in H. Takahashi et al., *Sci. Rep.*, 5:14781 (2015).

Example 10. Assessment of Rat Hippocampal LTP by Field Recordings

The protocol for recording extracellular field excitatory postsynaptic potentials (EPSPs) in rat hippocampus is described in H. Takahashi et al., *Sci. Rep.*, 5:14781 (2015).

Example 11. S-Nitrosylation of NMDA Receptors

The protocol for performing S-nitrosylation of NMDA receptors in rat brain in a biotin switch assay is described in H. Takahashi et al., *Sci. Rep.*, 5:14781 (2015).

Example 12. In Vitro Protection Against Neurotoxicity

Mixed cerebrocortical cultures, composed of similar cell types as found in vivo in the cerebral cortex, are used [Chen et al., *Neurosci.*, 86:1121-1132 (1998); and Kim et al., *Neuron*, 24:461-469 (1999)]. For neurotoxicity experiments using rat fetal cortical cultures, the normal culture medium is exchanged at room temperature for Earle's Balanced Salt Solution (EBSS) without phenol red. Cultures are then incubated in NMDA (dose response curve of 10 μM-1 mM) for 5 to 30 min. The culture medium is then replaced with fresh EBSS, and the cultures are returned to the incubator. Cultures are scored for neuronal viability at various times up to 24 hr using assays that quantitate cell death and distinguish between apoptosis and necrosis.

Mild insults with NMDA induce apoptosis (monitored by propidium iodide staining and morphology after cell permeabilization, DNA fragmentation in agarose gels, electron microscopy, in situ labeling of DNA fragments [TUNEL and ApoTag] with morphology, and ELISA of histone-associated DNA fragments [mono- and oligonucleosomes]) [Bonfoco et al., Techniques for distinguishing apoptosis from necrosis in cerebrocortical and cerebellar neurons, in Neuromethods: Apoptosis Techniques and Protocols, J. Poirier, Ed., pp. 237-253 (1997) (Humana, Totowa, New Jersey)]. Intense insults with NMDA induce necrosis (monitored by histology, trypan blue staining, and lactate dehydrogenase [LDH] leakage) [Ankarcrona et al., *Neuron*, 15:961-973 (1995); Bonfoco et al., *Proc. Natl. Acad. Sci. USA*, 92:7162-7166 (1995); Bonfoco et al. (1997, supra); and Nicotera et al., *Apoptosis*, 1:5-10 (1996)]. Dose-response for protection by test compounds is evaluated using memantine and nitroglycerin alone and combined as controls.

In situ detection of apoptotic cells is performed by TUNEL staining using a commercial kit (Intergen, Purchase, New York). After being washed with PBS, cells cultured on slides are fixed with 1% paraformaldehyde for 10 min. After being washed with PBS, the adherent cultured cells are incubated with terminal deoxynucleotidyl transferase (TdT) in a humidified chamber at 37° C. for 1 hr. After being treated with stop/wash buffer at room temperature for 10 min and three washes with PBS, cells are incubated with anti-digoxigenin conjugated with fluorescein in a humidified chamber at room temperature for 30 min. After 4 washes in PBS, the slides with adherent cultured cells are counterstained with 0.5 μg/mL propidium iodide and mounted with a glass cover slip. The number of apoptotic cells are counted under a microscope (100× magnification).

Example 13. In Vitro Protection of Primary Cerebellum Granule Cells of Rats

Isolated primary cerebellum granule cells of infant rats are inoculated in 96-well plates at about $1.2 \times 10^5$ cells per well using 10% FBS+25 mM KCl+2 mM glutamine+1% of double-antibody BME medium. After 24 hours, cytarabine at a final concentration of 10 μM is added to inhibit the proliferation of neurogliocyte cells. After day 4, glucose at a final concentration of 5 mM is added every four days to complement energy metabolism and water evaporation of cells. The materials are placed in a cell incubator (37° C., 5% $CO_2$) for culturing for 10 days. 200 μM of glutamate is used to induce excitotoxic injury of the primary cerebellum granule cells. Test groups include normal control group, glutamate group, pretreatment groups with different amino-adamantyl nitrate compounds, and pretreatment control group with memantine. After pretreatment for 2 hr, 200 μM of glutamate is added to induce cell damage for 24 hr, and then MTT [3-(4,5-dimethylthiazol-2-yl)-2,5-diphenyltetrazolium bromide] is added to the culture for 4 hr. The supernatant fraction is removed, and 150 μL of DMSO is added to each well for dissolving. After blending with shaking, the light absorption values at 570 nm wavelength is measured with a microplate reader, and the viability of cells is calculated. Cell viability (%)=(absorbance of test group/absorbance of normal control group)×100%.

Example 14. Water Maze Neurobehavioral Test in Rats

The protocol for conducting a water maze neurobehavioral test in spontaneously hypertensive rats is described in H. Takahashi et al., *Sci. Rep.*, 5:14781 (2015).

Example 15. In Vivo Neuroprotection in a Murine Cerebral Ischemia Model

In a mouse model of focal cerebral ischemia/reperfusion, the middle cerebral artery (MCA) of C57BL/6 mice is ligated for 2 hr using an intraluminal suture method as described in Chen et al., *Neurosci.*, 86:1121-1132 (1998). A loading dose of a test compound or vehicle control is initially administered intraperitoneally (i.p.) 2 hr after MCA occlusion, followed by i.p. administration of a maintenance dose of the test compound or vehicle control every 12 hr for 48 hr. The animals are sacrificed and analyzed with TTC staining 48 hr after MCA occlusion. Outcomes of focal cerebral ischemia/reperfusion induced by the intraluminal suture method, such as infarct area or volume, are measured as a gage of the test compound's ability to reduce cerebral damage after a stroke.

Example 16. In Vivo Neuroprotection in a Rat Cerebral Ischemia Model

Compounds were tested for inhibition of NMDA receptors using NMDA glutamate receptors NR1/NR2B encoded by the human GRIN1 and GRIN2B genes, expressed in HEK293 cells (originally from ATCC, Manassas, VA). Cells were maintained in tissue culture incubators, and stocks were maintained in cryogenic storage. Cells used for electrophysiology were plated in 150-mm plastic culture dishes. HEK293 cells were transfected with the appropriate ion channel or receptor cDNA(s) encoding NR1 and NR2B. Stable transfectants were selected using the G418 and Zeocin™-resistance genes incorporated into the expression plasmid. Selection pressure was maintained with G418 and Zeocin™ in the culture medium. Cells were cultured in Dulbecco's Modified Eagle Medium/Nutrient Mixture F-12 (D-MEM/F-12) supplemented with 10% fetal bovine serum, 100 U/mL penicillin G sodium, 100 μg/mL streptomycin sulfate, 100 μg/mL Zeocin™, 5 μg/mL blasticidin, and 500 μg/mL G418.

Test compounds were evaluated in 8-point concentration-response format (8 replicate wells/concentration). All test and control solutions contained 0.3% DMSO. The test article formulations were loaded in a 384-well plate using an automated liquid handling system (SciClone ALH3000, Caliper LifeScienses). To verify the sensitivity the assay, the antagonist positive control article (memantine) was applied at 8 concentrations (n=4, where n=the number of replicates).

The effects of the test compounds were evaluated using the IonWorks® Barracuda™ Automated Patch Clamp System. Intracellular solution contained 50 mM CsCl, 90 mM CsF, 2 mM MgCl2, 5 mM EGTA, and 10 mM HEPES, pH 7.2. This solution was prepared in batches and stored refrigerated. In preparation for a recording session, the intracellular solution was loaded into the intracellular compartment of the PPC planar electrode. Extracellular solution (137 mM NaCl; 1.0 mM KCl; 5 mM $CaCl_2$); 10 mM HEPES; 10 mM glucose; pH 7.4. Patch clamp measurements were made with a holding potential of −70 mV, and the potential during compound application was −40 mV. Extracellular buffer was loaded into the PPC plate wells (11 μL per well). Cell suspension was then pipetted into the wells (9 μL per well) of the PPC planar electrode. Whole-cell recording configuration was established via patch perforation with membrane currents recorded by on-board patch clamp amplifiers. Two recordings (scans) were performed: first, during pre-application of test articles and, second, co-application test article with agonist (EC50 L-glutamate) and to detect inhibition of NR1/NR2B receptors by the test article. The application consisted of two additions of 20 μL test solution containing antagonists at 10 μL/s (2 second total application time). First addition of 2× concentrated articles were preapplied for 5 minutes before the second addition of 1× concentrated articles. Data acquisition was performed via the IonWorks® Barracuda™ software, and data was analyzed using Microsoft Excel (Microsoft Corp., Redmond, WA). Concentration-response data was fitted to a Hill equation of the following form:

$$\text{RESPONSE} = \text{Base} + [(\text{Max}-\text{Base})/(1+(x_{half}/x)^{rate})]$$

where Base is the response at low concentrations of test article, Max is the maximum response at high concentrations, $x_{half}$ is the $EC_{50}$, or $IC_{50}$, the concentration of test article producing either half-maximal activation or inhibition, and rate is the Hill coefficient. Nonlinear least squares fits were made assuming a simple binding model. Fits were weighted by the standard deviation. No assumptions about the fit parameters were made; the fit parameters were determined by the algorithm.

As shown in Table 1, all test compounds inhibited NR1/NR2B glutamate receptors. Varying degrees of inhibition were shown for the various compounds. Memantine, control antagonist, produced inhibition of the receptors similar to the inhibition previously observed. Glutamate, control agonist, stimulated the receptors.

TABLE 1

IC50 values for test compounds

| Compound ID | Peak current IC50 (μM) | Steady state current IC50 (μM) |
|---|---|---|
| Memantine-HCl | 2.96 | 1.14 |
| NM-004 | 25.94 | 20.96 |
| YQW-036 | 10.11 | 6.80 |
| Cmpd 1 | 4.59 | 2.62 |
| Cmpd 2 | 73.22 | 47.36 |
| Cmpd 3 | 8.01 | 5.08 |
| Cmpd 4 | 35.24 | 34.24 |
| Cmpd 5 | 11.22 | 7.18 |

TABLE 1-continued

IC50 values for test compounds

| Compound ID | Peak current IC50 (μM) | Steady state current IC50 (μM) |
|---|---|---|
| Glutamate CRC* | 2.7** | 1.44** |
| Memantine CRC* | 3.51 | 1.68 |

*reference controls
**EC50 is shown

Memantine:

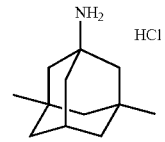

NM-004:

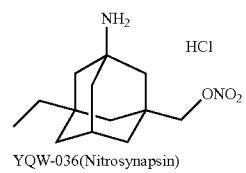

YQW-036(Nitrosynapsin)

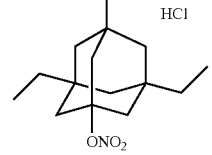

Cmpd 1:

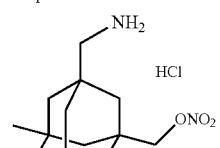

Cmpd 2:

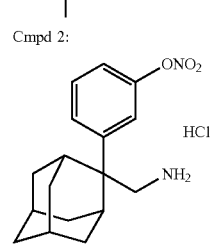

Cmpd 3:

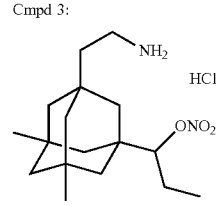

Cmpd 4:

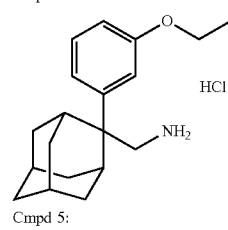

Cmpd 5:

TABLE 1-continued

IC50 values for test compounds

| Compound ID | Peak current IC50 (μM) | Steady state current IC50 (μM) |
|---|---|---|
|  | | |

Compounds 1-5 all showed activity for inhibiting the NR1/NR2B glutamate receptor. These compounds can be useful for improving memory, awareness, and ability to perform daily functions. These compounds can be used to treat diabetes, cerebral ischemia, traumatic brain injury, stroke, epilepsy, autism spectrum disorder, a broad range of neurodegenerative and other CNS disorders, dementia (e.g., Alzheimer's disease, vascular dementia, dementia with Lewy bodies, frontotemporal dementia and HIV-associated dementia), Huntington's disease, Parkinson's disease, multiple system atrophy (Shy-Drager syndrome), cerebellar degeneration, ataxia (e.g., cerebellar ataxia, spinocerebellar ataxia, Friedreich's ataxia and ataxia-telangiectasia [Louis-Bar syndrome]), motor neuron diseases (e.g., amyotrophic lateral sclerosis [ALS], primary lateral sclerosis [PLS], progressive muscular atrophy [PMA] and spinal muscular atrophy [SMA]), multiple sclerosis, vision impairment or loss caused by neurodegeneration of the visual pathway (e.g., optic neuropathy/atrophy, glaucoma and age-related macular degeneration), and sensorineural hearing loss. dementia (e.g., Alzheimer's disease, vascular dementia, dementia with Lewy bodies, frontotemporal dementia and HIV-associated dementia), Huntington's disease (which often leads to dementia), Parkinson's disease (which often leads to dementia), multiple system atrophy (Shy-Drager syndrome), cerebellar degeneration, ataxia (e.g., cerebellar ataxia, spinocerebellar ataxia, Friedreich's ataxia and ataxia-telangiectasia [Louis-Bar syndrome]), motor neuron diseases (e.g., amyotrophic lateral sclerosis [ALS], primary lateral sclerosis [PLS], progressive muscular atrophy [PMA] and spinal muscular atrophy [SMA]), multiple sclerosis, vision impairment or loss caused by neurodegeneration of the visual pathway (e.g., optic neuropathy/atrophy, glaucoma and age-related macular degeneration [AMD]), and sensorineural hearing loss.

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that all aspects of the disclosure are not limited to the specific depictions, configurations or relative proportions set forth herein, which may depend upon a variety of conditions and variables. Various modifications and variations in form and detail of the embodiments and examples of the disclosure will be apparent to a person skilled in the art. It is therefore contemplated that the disclosure also covers any and all such modifications, variations and equivalents.

What is claimed is:

1. A method of treating a central nervous system (CNS) disorder, comprising administering a therapeutically effective amount of a compound of Formula I, wherein Formula I is:

(I)

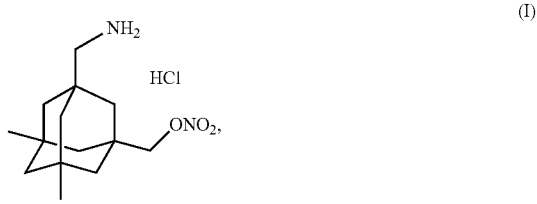

or a pharmaceutically acceptable salt thereof; and
wherein the CNS disorder is associated with excitotoxicity due to excessive extrasynaptic glutamate.

2. The method of claim 1, wherein the CNS disorder is a neurodegenerative disorder.

3. The method of claim 2, wherein the neurodegenerative disorder is dementia with Lewy bodies or Alzheimer's disease.

4. The method of claim 1, wherein the CNS disorder is brain ischemia, traumatic brain injury, epilepsy, pain or autism spectrum disorder.

5. The method of claim 4, wherein the CNS disorder is an autism spectrum disorder.

6. The method of claim 5, wherein the autism spectrum disorder is autism.

7. The method of claim 4, wherein the CNS disorder is epilepsy.

8. The method of claim 4, wherein the CNS disorder is traumatic brain injury.

9. The method of claim 4, wherein the CNS disorder is brain ischemia.

10. The method of claim 1, wherein the CNS disorder is a neurodevelopmental disorder.

11. The method of claim 10, wherein the neurodevelopmental disorder is MEF2C haploinsufficiency syndrome.

12. The method of claim 1, wherein the therapeutically effective amount is a dose of less than 100 mg/kg per day.

13. The method of claim 12, wherein the therapeutically effective amount is a dose of 10 to 30 mg/kg per day.

14. The method of claim 13, wherein the therapeutically effective amount is a dose of 20 mg/kg per day.

15. The method of claim 1, wherein the compound of Formula I is administered orally.

16. The method of claim 1, wherein the compound of Formula I is administered parenterally.

17. The method of claim 1, further comprising administering an additional therapeutic agent.

* * * * *